United States Patent
Steinarsson et al.

(10) Patent No.: US 12,414,701 B2
(45) Date of Patent: Sep. 16, 2025

(54) METHOD AND SYSTEM FOR DETERMINING EXERCISE PARAMETERS INCLUDING AEROBIC ENDURANCE BASED ON HEART RATE CURVE ANALYSIS

(71) Applicant: DRIFTLINE EHF., Kopavogur (IS)

(72) Inventors: Agnar Steinarsson, Kopavogur (IS); Steinar Sindri Agnarsson, Grindavik (IS)

(73) Assignee: DRIFTLINE EHF., Kopavogur (IS)

( * ) Notice: Subject to any disclaimer, the term of this patent is extended or adjusted under 35 U.S.C. 154(b) by 207 days.

(21) Appl. No.: 17/904,327

(22) PCT Filed: Dec. 21, 2020

(86) PCT No.: PCT/IS2020/050023
§ 371 (c)(1),
(2) Date: Aug. 16, 2022

(87) PCT Pub. No.: WO2021/166000
PCT Pub. Date: Aug. 26, 2021

(65) Prior Publication Data
US 2023/0138921 A1   May 4, 2023

(30) Foreign Application Priority Data
Feb. 17, 2020   (IS) .......................................... 050291

(51) Int. Cl.
*A61B 5/0255* (2006.01)
*A61B 5/00* (2006.01)

(52) U.S. Cl.
CPC .......... *A61B 5/0255* (2013.01); *A61B 5/4866* (2013.01); *A61B 5/7235* (2013.01)

(58) Field of Classification Search
CPC ..... A61B 5/024; A61B 5/222; A61B 2503/10; A61B 5/1118; A63B 2024/0065
See application file for complete search history.

(56) References Cited

U.S. PATENT DOCUMENTS

| | | |
|---|---|---|
| 2006/0063980 A1 | 3/2006 | Hwang et al. |
| 2007/0249949 A1 | 10/2007 | Hadley |
| 2012/0029370 A1* | 2/2012 | Rocker ................. A61B 5/024 600/508 |
| 2015/0297133 A1 | 10/2015 | Jouanique-Dubuis et al. |

(Continued)

OTHER PUBLICATIONS

International Search Report and Written Opinion in International Application No. PCT/IS2020/050023, 16 pages, Mar. 23, 2021.

*Primary Examiner* — Tse W Chen
*Assistant Examiner* — Michael A Catina
(74) *Attorney, Agent, or Firm* — HESLIN ROTHENBERG FARLEY & MESITI P.C.

(57) ABSTRACT

Provided is a computer-implemented method of determining exercise parameters, such as heart rate thresholds, endurance, maximum heart rate and lactate threshold. The method comprises fitting a continuous curve to heart rate data obtained over time from the onset of exercise, the curve comprising a plurality of components that meet at transition points that join the components. The exercise parameters are obtained from the curve fitting of the heart rate data. Also provided is a system for determining exercise parameters, in particular a computer-implemented system that determines exercise parameters using the disclosed method.

13 Claims, 38 Drawing Sheets

(56) References Cited

U.S. PATENT DOCUMENTS

| | | | |
|---|---|---|---|
| 2017/0027507 A1* | 2/2017 | Yeh | A61B 5/024 |
| 2017/0238875 A1* | 8/2017 | Olivier | A61B 5/02438 |
| 2019/0209049 A1 | 7/2019 | Granlund et al. | |

\* cited by examiner

METHOD AND SYSTEM FOR DETERMINING EXERCISE PARAMETERS INCLUDING AEROBIC ENDURANCE BASED ON HEART RATE CURVE ANALYSIS

CROSS REFERENCE TO RELATED APPLICATIONS

This application is a U.S. National Phase filing under 35 U.S.C. § 371 of International Application PCT/IS2020/050023, filed Dec. 21, 2020, and published as WO2021/166000A1 on Aug. 26, 2021. PCT/IS2020/050023 claims priority from Iceland application number 050291, filed Feb. 17, 2020. The entire contents of each of these prior applications are hereby incorporated herein by reference.

FIELD

The invention is related to the computer-implemented methods of determining fitness parameters. The invention is further related to systems useful for determining fitness parameters.

INTRODUCTION

The Growing Use of Wearable Fitness Trackers

Running is the world's most popular form of fitness activity and most active runners now use wearable sensors (fitness trackers) that can monitor heart rate and track speed, distance, cadence and elevation through automatic GPS positioning. Some of the applications now also offer some physiological assessment of the user, such as automatic estimation of VO2max or lactate threshold. Wrist-based heart rate monitoring is performed with optical detection of blood flow through the skin (photoplethysmography, PPG) and recent studies have shown that this method is generally accurate for heart rate measurement.

The Biological Energy Systems

Human exercise physiology assumes two major metabolic pathways to produce energy for locomotion, i.e. aerobic (with oxygen) and anaerobic (without oxygen) pathways. Glucose and fats from digested food are metabolized in three energy systems to provide and replenish ATP for energy production. Those three systems are the Phosphagen system (anaerobic), the Glycolytic system (anaerobic and aerobic) and the Oxidative system (aerobic). Energy thresholds, such as the lactate threshold and the VO2max threshold (vVO2max) have been defined where the runner switches between energy systems (McArdle, Katch and Katch 2001. Exercise physiology: Energy, nutrition and human performance. $5^{th}$ edition, 161-162).

The Cardiorespiratory Response to Exercise

Any sustained activity or exercise evokes cardiorespiratory responses, i.e. a cardiovascular effect involving the circulatory system (heart and blood) and a respiratory effect involving the respiratory system (lungs and respiratory tract). Some of those responses are summarized in FIG. 1. The first graph in FIG. 1 shows how heart rate (HR) and cardiac output (CO) increase linearly with increased exercise intensity, while stroke volume (SV) peaks at around 50-60% of HRmax. The second graph shows that respiratory rate (RR) has a segmented linear relationship with exercise intensity, with clear breaks at the ventilatory thresholds (VT1 and VT2). Tidal volume (TV) increases curvilinearly and peaks at around 70-80% of HRmax. The third graph shows how the respiratory exchange changes with exercise intensity. The anaerobic threshold (AT) is indicated where the lines intersect, reflecting a respiratory exchange ratio (RER) of 1.

Under prolonged exercise at constant intensity, the heart rate rises very rapidly at first but then levels off, preceding a steady and slow rise towards the end of the exercise. This phenomenon is called cardiovascular drift and is generally attributed to a decline in stroke volume and the activation of less energy-efficient muscle fibres as the activity progresses. The cardiovascular drift reflects endurance and is central to the theory underlying the present invention.

The Key Indicators of Endurance Performance

Maximum oxygen consumption (VO2max) VO2max is defined as the maximum rate of oxygen consumption measured during an incremental exercise test. VO2max has been found to decline with age by about 10% per decade, irrespective of training status, but it is always much higher in the trained population. VO2max has generally been considered the primary determinant of endurance performance, largely based on the notion that the endurance performance is limited by the availability of oxygen. However, during the last several decades countless scientific studies have revealed that VO2max in fact is a poor predictor of endurance performance.

The Lactate Threshold (LT)

The lactate threshold is commonly split into two parts, LT1 and LT2. The former (LT1) is recognized as the exercise intensity corresponding to a sustained increase in blood lactate concentration above resting levels (typically below 2 mmol/L). The latter (LT2) is the intensity corresponding to a rapid rise in blood lactate at the upper limit of sustainable exercise (typically around 4 mmol/L). This threshold has previously been given many different names, such as OBLA (onset of blood lactate accumulation) or MLSS (maximum lactate steady state). Studies have shown that the lactate threshold (LT) has a high predictive power for performance in endurance races. The downside is that measurements are traditionally done in all-out laboratory tests, involving blood samples for measuring lactate, subject to considerable error.

Maximum Heart Rate (HRmax)

The maximum heart rate is usually measured directly with a graded exercise test, such as an incremental running or cycling test to exhaustion. There are currently no existing submaximal methods available for measuring the maximum heart rate (HRmax). Comparative studies have shown that endurance athletes reach a 6-7% higher HRmax during training and competition, compared to laboratory tests. Maximum heart rate (HRmax) has been found to decrease linearly with increasing age, by about 7-8 beats per decade on average, and then much faster after seventy. The great individual variability seen in such demographic studies means that it is not possible to use a general linear equation to accurately predict human HRmax.

Recovery after Exercise (EPOC)

The recovery after exercise is characterized by a non-linear decrease in heart rate and oxygen consumption. The restoration of homeostasis post-exercise requires work from the oxidative system and causes excess post-exercise oxygen consumption (EPOC), when compared to the pre-exercise resting values. The magnitude of EPOC reflects the oxygen deficit accumulated due to anaerobic processes during the exercise, which is restored through the oxidative system post-exercise.

Relevant Research in Sports Exercise Physiology

Heart Rate Kinetics

In recent years, new computer models have been introduced that can simulate the heart rate response under a variable intensity (nonlinear dynamical system models). Such models require input or assumptions such as HRmin, HRmax, vVO2max and running speed in an 800 m run. These heart rate kinetic models are now able to closely simulate the heart rate response, but they do not understand the physiological factors behind it, e.g. thresholds and their interaction (Zakynthinaki 2016. Simulating heart rate kinetics during incremental and interval training, Biomedical Human Kinetics, 8(1), 144-152).

VO2 Kinetics

New research on oxygen uptake during constant exercise divides the VO2 curve into three different parts i.e. phase I (cardiodynamic phase), phase II (primary/rapid component) and phase III (slow component). The first phase only takes about 20 seconds and is characterized by a sudden rise in VO2. The next phase begins after about 20 seconds and is usually a few minutes in length, characterized by a rapid increase in VO2 (hence the "rapid component"). In the third phase, a slow and steady increase in VO2 occurs (slow component), but a steady state is not achieved. If the intensity is greater than the lactate threshold, VO2 rises completely to VO2max at exhaustion (Burnley and Jones 2018. Power—duration relationship: Physiology, fatigue, and the limits of human performance, European Journal of Sport Science, 18:1, 1-12).

Fitness Testing and Performance Analysis

Fitness Tests and Trackers

In recent years, performance analysis has been attaining increasing interest from a range of stakeholders within sport, such as coaches, performance analysts and players. Measurements are traditionally performed on a treadmill or a cycle ergometer in specialized laboratories. However, laboratory tests are very demanding for the athletes and therefore, many simple maximum effort endurance tests are used by team sports coaches to evaluate running capacity. Most often, these tests indirectly estimate VO2max, such as the Cooper test (12-minute run) or the Shuttle run (beep test). There is a growing need for applications that can determine exercise related parameters accurately based on submaximal exercise.

All the major fitness hardware brands on the market now produce advanced wearable fitness trackers that offer a range of automatic physiological measurements. These include VO2max, lactate threshold, race time prediction, fitness tests, heart rate variability (HRV), performance condition, training effect, training status, training load, recovery time, stress tests and a range of running dynamics. Below is a discussion about some of these measurements, as they relate directly to the present invention.

VO2max Estimation

VO2max has recently been presented as a direct marker of cardiorespiratory fitness (CRF) by many of the major fitness hardware brands on the market. All these brands estimate VO2max from the heart rate vs speed relationship of their users during running. This method, commonly used in fitness monitors such as those marketed by Garmin, Suunto, Jabra, Huawei and PulseOn, is based on the documented linear relationship between heart rate, oxygen uptake and running speed (see FIG. 1(a)).

In this method, the wearable sensor measures speed using GPS and then the heart rate at different speed values is used to map the relationship between speed and heart rate. The device then forecasts a straight line up towards an estimated HRmax, and this speed estimate is then translated into VO2max, based on anthropometric data, such as BMI, gender and age. The VO2max estimate is then used as a proxy for endurance performance, despite overwhelming scientific evidence showing a weak correlation of this metric to endurance performance (Firstbeat Technologies 2014. "Automated Fitness Level (VO2max) Estimation with Heart Rate and Speed Data". www.firstbeat.com).

Lactate Threshold Estimation

Another common fitness feature offered in some trackers and software is a sub-maximal estimation of the lactate threshold (LT), which is generally viewed as a good marker of endurance performance. The LT pace of most runners is close to their 10-20 km race pace. Many fitness trackers use the Firstbeat method (US2011/0040193) to detect LT. By gathering heart rate data across a range of paces, the device estimates LT both in terms of a running pace and a heart rate level. The LT is detected from minor changes in heart rate variability (HRV) at the ventilatory threshold (breakpoint increase in respiratory rate). However, the test is quite demanding and requires a chest-strap monitor to measure the heart rate variability (HRV). Independent studies have revealed that the detection of HRV with wearable sensors can be very inaccurate, especially at higher exercise intensities. The Polar fitness test is based on the analysis of HRV at rest but laboratory studies and large user studies (by HRV4 Training) have revealed that HRV is not a valid marker of aerobic fitness.

EPOC Estimation

Some of the more advanced fitness trackers offer analysis of the recovery phase after exercise. Firstbeat Technologies have developed an indirect method for prediction of EPOC (excess post-exercise oxygen consumption) based on heart rate measurement (US2006/0032315). The EPOC prediction is used for the assessment of training load and training effect in athletes. The company developed an estimation model that uses input parameters, such as HRmax, % VO2max and respiration rate to estimate EPOC accumulated during exercise. Respiration rate is estimated from HRV and as such, the method is limited to the use of chest strap HR-monitors. Laboratory studies showed a decent correlation between predicted and measured EPOC, but the individual error is extremely large. Clearly, this prediction method does not provide a realistic estimation of exercise induced EPOC.

SUMMARY

The present invention introduces a new methodology to analyse and extract health- and fitness information from human heart rate data collected by personal fitness monitors. The invention addresses the foregoing drawbacks and limitations by providing a method and system for determining exercise and endurance parameters based on the analysis of heart rate over time. The application analyses heart rate data from submaximal running and provides a unique analysis of the user's running ability.

The method and system in accordance with the invention can be implemented as a smartphone application, for use by athletes (such as runners, bikers, walkers, etc.), coaches, trainers and others who wish to analyse their exercise capacity in a new and revolutionary way. The method and system analyses data from a submaximal exercise test and can be adapted to work with all major exercise watches on the market, such as Apple Watch, Polar, Garmin and Fitbit. The method and system thus allow users to use their own fitness monitors to analyse their exercise capacity. The invention offers an array of personal fitness metrics for the user, such as Endurance (based on the alignment of speed thresholds), Maximum speed, HRmax and Lactate threshold (all measured sub-maximally), as well as many other fitness metrics. One such metric is the Runscore, a universal fitness metric independent of age, gender and distance, based on the IAAF scoring tables. The method can furthermore predict potential race performance over all distances.

The method can be provided as an application that can be implemented on any computer-implemented system or device capable of receiving and analysing heart-rate data, i.e. a device such as smartphones, smart watch or computers. The application may run on the same device as the data collection device (e.g. smart watch), or the application may be executed on e.g. a computer or smartphone that is adapted to receive data from a data collection device (e.g. a GPS watch and heart rate monitor).

To summarize, the present invention has both technical and conceptual aspects. The technical aspect involves a new methodology to analyse heart rate data and extract information on health- and fitness parameters. Among the novelties of the methodology is the measurement of maximum heart rate and maximum running speed from submaximal tests. Also, the identification of five speed thresholds, reflecting shifts between the body's energy systems.

The conceptual aspect involves the presentation of new concepts within sports exercise physiology. The most important of these is the first physiologically sound measure of aerobic endurance, the Endurance parameter (E). While endurance is undoubtedly a major aspect of human physiology, still today there exists no direct measure of endurance. The E-parameter presented herein, reflects the alignment of speed thresholds and gives a meaningful score, ranging from 0-100%.

The method utilises heart rate data that are a measure of the workload intensity of the cardiovascular system of a human. Heart rate data can preferably be associated with a time stamp, to generate data that contains information on heart rate as a function of time. The heart rate data can be measured continuously, and the resulting values recorded on the system, each heart rate value thus resulting in a data point that can be analysed by the system.

The invention thus relates to a computer-implemented method of determining exercise parameters, based on heart-rate data for the individual, i.e. data describing heart rate over time during exercise. The invention also relates to a system for determining exercise parameters, in particular a system that is adapted to carry out the method as disclosed herein.

In a general sense, the method involves fitting a curve to heart rate data during exercise, where the parameters describing the curve are descriptive of the exercise capabilities (i.e. exercise parameters) of the human, or the parameters can be used to calculate such exercise parameters. Underlying the method is a novel concept of human exercise that has been developed by the present inventor. Based on this concept, heart rate following onset of human exercise follows a trajectory that can be described by a curve that comprises multiple components, wherein each component describes the heart rate during the exercise over a specific time period of the exercise. Each component is immediately followed by an additional component, until the end of the exercise, the components meeting at points on the heart rate vs. time trajectory that are herein called transition points.

Accordingly, in a first aspect the invention relates to a computer-implemented method of determining at least one exercise parameter for a human individual, comprising consecutive steps of (i) providing data describing heart rate as a function of time during exercise of at least one human individual; (ii) fitting a continuous curve to the heart rate data, the curve comprising a combination of a plurality of consecutive components that follow each other in order over time, wherein the components meet at transition points; and (iii) determining at least one exercise parameter value based on the curve fitting.

The curve fitting can be performed in an iterative fashion, i.e. by determining or estimating an initial set of parameters, calculating a continuous curve estimate based on those initial parameters, and calculating the deviation of the continuous curve estimate from the actual heart rate data. The initial set of parameters is then changed, and the process of calculating the continuous curve and the deviation of the curve from the actual heart rate data repeated until a best fit to the heart rate data is obtained.

For example, the method can first estimate the position of the transition points on the curve, based on an initial set of parameters describing the transition points. This is followed by the calculation of a continuous curve that goes through and connects the transition points, and the determination of the deviation of the curve from the actual heart rate data. The process of determining the position of the transition points and the continuous curve can then be repeated until a best fit (minimized deviation from the data) is obtained.

The method can optionally further include analysis of heart rate data that immediately follows the end of an exercise. In this method, heart rate data is collected during the exercise, and continuously following the end of the exercise, when the individual is in a resting state following the end of exercise (i.e., the individual is not exercising during this time).

Accordingly, the invention also relates to a computer-implemented method of determining at least one exercise parameter of a human individual, the method comprising consecutive steps of (i) providing data describing heart rate in a first time period from the start of an exercise for the human individual until the end of the exercise, followed by a second time period that follows the first time period, and wherein during the second time period, the individual is in a resting state; (ii) fitting a continuous curve to the heart rate data, the curve comprising a first section, describing heart rate in the first time period, and a second section, describing the heart rate in the second time period; and (iii) determining at least one exercise parameter value based on the curve fitting.

The method of the invention can be implemented on a computer system of choice. It follows that further aspects of the invention relate to a system, or a computer-implemented system, that is adapted to carry out the method.

In an aspect, a system for determining at least one exercise parameter is also provided, the system comprising (a) at least one computer-readable memory; (b) at least one processing unit, adapted to (i) receive data describing heart rate for a human exercise over time during exercise, (ii) storing the data to computer-readable memory, (iii) fitting a continuous curve comprising a plurality of consecutive components to the heart rate data, and (iv) determining at least one exercise parameter value from the curve fitting or its individual components. The system can optionally also include at least one display unit, for displaying at least one exercise parameter.

A further aspect relates to a computer-implemented system for determining at least one exercise parameter for a human individual, comprising (a) at least one storage unit, for receiving and storing data representing heart rate over time for at least one human individual; (b) at least one central processing unit, for processing the heart rate data, the processing comprising fitting a curve to the heart rate data, the curve comprising a combination of a plurality of consecutive components that follow each other in order over time, wherein the components meet at transition points, and wherein the central processing unit is adapted to determine at least one exercise parameter value from the curve fitting or its individual components.

The computer-implemented system can be adapted to carry out the method to determine exercise parameters, as described generally in the following description and specifically in the listed embodiments.

The invention can be described by the following numbered embodiments, with further features and examples of embodiments disclosed in the following description:

1. A computer-implemented method of determining at least one exercise parameter for a human individual, comprising steps of:
   providing data describing heart rate as a function of time during exercise of at least one human individual;
   fitting a continuous curve to the heart rate data, the curve comprising a combination of a plurality of consecutive components that follow each other in order over time, wherein the components meet at transition points; and
   determining at least one exercise parameter value based on the curve fitting.
2. The method of embodiment 1, wherein the data describes heart rate from the onset of the exercise.
3. The method of embodiment 1 or embodiment 2, wherein the curve comprises at least four consecutive components that meet at transition points, and wherein the difference in heart rate between at least the transition points connecting the first three components that follow the onset of the exercise is equal.
4. The method of any one of the preceding embodiments, wherein the fitting comprises first estimating the position of the transition points, followed by fitting a continuous curve in between the transition points.
5. The method of any one of the preceding embodiments, wherein the fitting comprises a stepwise process that comprises steps of:
   a. estimating the position of transition points;
   b. fitting a continuous curve to the heart rate data, wherein the curve components meet at the estimated transition points;
   c. determine the deviation of the continuous curve from the heart rate data;
   d. repeating the process in steps a-d until the deviation has been minimized.
6. The method of any one of the previous embodiments, wherein at least the last component is linear over time.
7. The method of any one of the previous embodiments, wherein the continuous curve comprises at least two consecutive non-linear components that are followed by at least one linear component.
8. The method of any one of the previous embodiments, wherein the continuous curve comprises at least five consecutive components, wherein at least the last two components are linear over time.
9. The method of any one of the previous embodiments, wherein the continuous curve comprises six consecutive components, wherein at least the second, third and fourth components are non-linear, and at least the fifth and sixth components are linear over time.
10. The method of any one previous embodiment, wherein the differences in heart rate between at least the first four transition points on the curve are equal.
11. The method of any one of the previous embodiments, wherein the data describes heart rate from the onset of an exercise and wherein the starting point of the continuous curve corresponds to the start of the exercise of the individual.
12. The method of any one of the previous embodiments, further comprising displaying at least one exercise parameter value.
13. The method of any one of the previous embodiments, wherein the non-linear components are represented by exponential decay functions.
14. The method of any one of the previous embodiments, comprising six consecutive components, wherein the first and second components meet at a first transition point (T1), the second and third components meet at a second transition point (T2), the third and fourth components meet at a third transition point (T3), the fourth and fifth components meet at a fourth transition point (T4), and the fifth and sixth components meet at a fifth transition point (T5), wherein when the exercise is performed at an intensity that is equal to or below the lactate threshold for the individual, the heart rate difference between successive transition points is equal, i.e. Ti=HR(T5)−HR(T4)=HR(T4)−HR(T3)=HR(T3)−HR(T2)=HR(T2)−HR(T1), and when the exercise is performed at an intensity that is above the lactate threshold for the individual, the heart rate difference between successive transition points T1 to T4 is equal, i.e. Ti=HR(T4)−HR(T3)=HR(T3)−HR(T2)=HR(T2)−HR(T1), while the heart rate difference between transition points T4 and T5 (HR(T5)−HR(T4)) is smaller than Ti.
15. The method of any one of the previous embodiments, wherein the difference in time between adjacent transition points is independent of endurance level of an individual, while the time at the transition point between the last two components for the individual is a measure of the endurance level of the individual.
16. The method of any one of the previous embodiments, wherein the heart rate curve consists of six consecutive components, wherein the time at the first four transition points separating consecutive components is in a fixed relationship, independent of the endurance or exercise intensity of the individual, while the position of the fifth transition point is a measure of the endurance of the individual.
17. The method of any one of the previous embodiments, wherein the curve comprises six components, and wherein the time at transition point T4, t(T4), the time at transition point T3, t(T3), the time at transition point T2, t(T2), and the time at transition point Ti, t(T1) are, when the exercise is performed at an intensity that is below the lactate threshold of the individual, related as described by:

$$t(T4)=32t(T1), t(T3)=6\times t(T1) \text{ and } t(T2)=2\times t(T1),$$

and when the exercise is performed at an intensity that is at or above the super-lactic threshold for the individual (the intensity that elicits a maximized depletion rate of the phosphagen system at the beginning of exercise), the time at the transition points is related as described by $$t(T4)=4t(T1), t(T3)=3\times t(T1) \text{ and } t(T2)=2\times t(T1)$$

18. The method of any one of the previous embodiments, wherein the curve fitting of the heart rate curve for the human individual provides a measure of: the endurance level (E), the heart rate level (P) and the relative exercise intensity (V) of the individual.

19. The method of the previous embodiment, wherein the parameter values for E, P and V reflect the position of the transition points on the heart rate curve.

20. The method of any one of the previous embodiments wherein, for any given individual, the heart rate during exercise can range from a resting heart rate (P0=P) to a maximal heart rate (HRmax=P3=p3).

21. The method of the previous embodiment, wherein the maximum heart rate (HRmax=P3=p3) of the human individual equals 4(P).

22. The method of any one of the previous two embodiments, wherein for each individual, the heart rate curve is characterized by an aerobic threshold (p1) and an anaerobic threshold (p2).

23. The method of any one of the previous two embodiments, wherein the aerobic threshold (p1), the anaerobic threshold (p2) and the maximum heart rate (HR=p3) of the individual are respectively correlated with corresponding exercise intensity thresholds V1, V2 and V3.

24. The method of the previous embodiment, wherein the heart rate for a given individual at the aerobic threshold is a measure of the endurance of the individual, and wherein the aerobic threshold can range from P0 to P2, wherein $P2=3(P0)=3(P)=\frac{3}{4}HR_{max}$.

25. The method of any one of the previous embodiments 22-24, wherein the aerobic heart rate threshold (p1) for the individual can be described by the relationship:

$$p1=HR_{max}*(E/(E+1)).$$

26. The method of the previous embodiment, wherein the aerobic heart rate threshold p1 for the individual can take on values in the range of $HR_{max}*\frac{1}{4}$ to $HRmax*\frac{3}{4}$.

27. The method of the previous embodiment, wherein a p1 value for of $HRmax*\frac{1}{4}$ corresponds to an endurance value (E) of 0%, and wherein a p1 value of $HRmax*\frac{3}{4}$ corresponds to an endurance value (E) of 100%.

28. The method of any one of the previous embodiments 22-27, wherein the aerobic heart rate threshold (p1) is related to HRmax by the relationship:

$$p1=P+p1\%*(HRmax)$$

29. The method of any one of the previous embodiments 18-28, wherein the endurance (E) of the individual is obtained from a linear extrapolation of the linear component (E-line) connecting transition points T4 and T5.

30. The method of the previous embodiment, wherein E is obtained from the relationship:

$$E=\log(X/36),$$

wherein X is the absolute value of the intersect (in negative time) of the linear component joining transition points T4 and T5 with a line representing the aerobic heart rate threshold (p1).

31. The method of any one of the previous embodiments 18-30, wherein the lactic running speed threshold (VL) for the individual is obtainable from the relationship $$VL = Vmax\left(\frac{E+1/3}{E+1}\right)$$

wherein Vmax is the maximum running speed of the individual.

32. The method of any one of the previous embodiments, wherein the linear components and non-linear components of the heart rate curve are described by equations of the form $$N_t(\text{linear})=N_a+N_b(t)$$

$$N_t(\text{non-linear})=Na+N_b(Ln(t))$$

where $N_t$ equals heart rate at any given time t, $N_a$ equals the y-axis intercept, $N_b$ equals the exponent of the equation and t equals time.

33. The method of any one of the previous embodiments, wherein the heart rate curve comprises a first linear component A that meets a first non-linear component at transition point T1, three consecutive non-linear components B, C, D that follow the first component and that meet at transition points T2 and T3, and a fifth linear component E that follows the three non-linear components and meets the D component at transition point T4, wherein the non-linear components are described by the equations:

$$B_t=B_a+B_b(Ln(t))$$

$$C_t=C_a+C_b(Ln(t))$$

$$D_t=D_a+D_b(Ln(t))$$

wherein $B_t$, $C_t$ and $D_t$ equal the heart rate at any given time t during the respective components (B, C and D), $B_a$, $C_a$ and $D_a$ equal the y-axis intercepts, $B_b$, $C_b$ and $D_b$ equal the exponents of the component logarithmic equations, and t equals time;

and wherein the linear A and F components are described by the equations:

$$A_t=A_a+A_b(t)$$

$$F_t=F_a+F_b(t)$$

where $A_t$ and $F_t$ equal heart rate at any given time t, $A_a$ and $F_a$ equal the y-axis intercepts, $A_b$ and $F_b$ equal the slopes of the lines and t equals time.

34. The method of the preceding embodiment, wherein the linear E component is, at sub-lactic speeds (<VL) and lactic speeds (>VL), respectively, wherein VL equals the lactate threshold speed (V2.333 in V units), described by the following equations:

$$E_t(\text{sub-lactic})=E_a+E_b(t)$$

$$E_t(\text{lactic})=T4+(PS-T4)(t-t4)/(t6-t4)$$

where $E_t$ equals heart rate at any given time t, $E_a$ equals the y-axis intercept, $E_b$ equals the slope of the line, t equals time, T4 equals heart rate at the T4 transition point, PS equals the supramaximal heart rate, and t4 and t6 equal times at T4 and T6 transition points, respectively.

35. The method of any one of the previous embodiments, wherein the heart rate data starts from the onset of exercise from a resting state of the individual.

36. The method of any one of the preceding embodiments, wherein the data describing heart rate as a function of time during exercise is obtained at constant or near-constant levels of physical exertion.

37. The method of any one of the previous embodiments, wherein the physical exercise is selected from running, swimming, biking, walking and cross-country skiing.

38. The method of any one of the previous embodiments, wherein the physical exercise is running.

39. The method of any one of the preceding embodiments, wherein the at least one exercise parameter is selected from: maximum heart rate, heart rate thresholds, maximum exercise intensity, maximum exercise speed, running thresholds, aerobic heart rate threshold, lactate heart rate threshold (LT), endurance, optimal exercise speed, time to exhaustion, maximal distance at give exercise intensity, predicted maximum exertion time (race time).

40. The method of any one of the previous embodiments, wherein the data describing heart rate for the human individual further includes heart rate data following the end of the exercise, wherein the heart rate of the individual approaches a resting heart rate following the end of the exercise by a heart rate recovery curve comprising at least two components that are separated by recovery transition points, and wherein the at least one exercise parameter is obtained by analysis of the heart rate curve during the exercise and the heart rate curve following the end of the exercise.

41. The method of the previous embodiment, wherein the heart rate recovery curve comprises at least four components that meet at recovery transition points (R-points).

42. The method of any one of the previous two embodiments, wherein the difference in heart rate ($R_i$) between at least the first three adjacent recovery transition points (R1, R2, R3) on the heart rate recovery curve is equal.

43. The method of any one of the previous three embodiments, wherein the difference in heart rate between adjacent recovery transition points ($R_i$) is equal to the difference in heart rate between transition points (T0 on the curve describing heart rate during the exercise.

44. The method of any one of the previous embodiments 41-43, wherein at least the last of the at least four components is linear over time.

45. The method of any one of the previous embodiments 40-44, wherein the heart rate recovery curve comprises at least six components that are separated by recovery transition points (R1-R5), and wherein at least the last component is linear in heart rate over time.

46. The method of the previous embodiment, wherein the heart rate interval ($R_i$) between any successive recovery transition points R1-R5 is equal in magnitude, and equal to the heart rate interval (T0 between transition points T1–T5 for the individual.

47. The method of the preceding embodiment, wherein the last two components are linear in heart rate over time.

48. A system for determining at least one exercise parameter for a human individual, the system comprising
    a. at least one computer-readable memory
    b. at least on processing unit, the processing unit being adapted to:
        receive data describing heart rate as a function of time during exercise of at least one human individual;
        storing the heart rate data to computer-readable memory;
        fitting a continuous curve to the heart rate data; and
        determining at least one exercise parameter value from the curve fitting or its individual components, and
    c. at least one display unit, for displaying the at least one exercise parameter value
    wherein the continuous curve comprises a combination of a plurality of consecutive components that follow each other in order over time, wherein the components meet at transition points.

49. The system of the previous embodiment, wherein the system is adapted to fitting a first continuous curve of the heart rate during exercise, followed by a second continuous curve that describes the decay in heart rate for the individual following the end of the exercise.

50. The system of the previous embodiment, wherein the system is adapted to calculate at least one exercise parameter as set forth by the method set forth in any one of the embodiments 1-46.

51. A computer-implemented system for determining at least one exercise parameter for a human individual, comprising:
    at least one storage unit, for receiving and storing data representing heart rate over time for at least one human individual;
    at least one central processing unit, for processing the heart rate data, the processing comprising fitting a curve to the heart rate data, the curve comprising a combination of a plurality of consecutive components that follow each other in order over time, wherein the components meet at transition points, and;
    wherein the central processing unit is adapted to determine at least one exercise parameter value from the curve fitting or its individual components.

52. The computer-implemented system of the previous embodiment, further comprising at least one display unit, for displaying at least one exercise parameter value.

53. The computer-implemented system of the previous embodiment, wherein the system is adapted to calculate at least one exercise parameter as set forth by the method set forth in any one of the embodiments 1-47.

54. A computer-implemented method of determining at least one exercise parameter for a human individual, comprising steps of:
    providing data describing heart rate in a first time period from the start of an exercise for the human individual until the end of the exercise, followed by a second time period that follows the first time period, and wherein during the second time period, the individual is in a resting state;
    fitting a continuous curve to the heart rate data, the curve comprising a first section, describing heart rate in the first time period, and a second section, describing the heart rate in the second time period; and
    determining at least one exercise parameter value based on the curve fitting.

55. The method of the previous embodiment, wherein each of the first and second section comprise a combination of at least four consecutive components that follow each other in order over time, wherein the components meet at transition points.

56. The method of the previous embodiment, wherein the difference in heart rate between at least the first three adjacent transition points in the first section is equal.

57. The method of the previous embodiment, wherein the difference in heart rate between at least the first three transition points in the second section is equal.

58. The method of any one of the previous three embodiments, wherein the difference in heart rate (T0 between at least the first three adjacent transition points in the first section is equal to the difference in heart rate ($R_i$) between at least the first three transition points in the second section.

59. The method of any one of the previous five embodiments, wherein the second section is preceded by a lag phase that immediately follows the end of the first phase.

60. The method of any one of the previous five embodiments, wherein the exercise is selected from running, cycling, walking, cross-country skiing, alpine skiing, swimming, soccer, basketball, handball.

In the present context, the term "exercise" is intended to refer to any human physical activity or workload that increases the heart rate of the individual to a significant degree. Usually, an exercise is intensity driven, i.e. a more rigorous and/or rapid physical activity results in increased intensity, which in turn results in increased heart rate.

By contrast, the term "resting state" is intended to refer to the state of a human individual where the individual does not undertake any exercise. Usually a resting state means that the individual does not move at all, or only moves minimally. Examples of resting states are those of an individual lying down without moving arms or legs, or individual in a sitting position, with minimal or no movement of arms or legs. The term can also refer to individuals in a standing position, with minimal or no movement of legs, i.e. the individual is standing still or walking very slowly.

The term "lactic threshold", in the present context, refers to the effort or intensity that an individual can maintain over a prolonged period of time without appreciable increase in lactic acid in the blood.

The term "super-lactic threshold", in the present context, is a new scientific term presented here by the inventors, as part of the physiological basis of the invention. The term refers to the effort or intensity that elicits a maximized depletion rate of the phosphagen system at the beginning of exercise. The term relates to the lactic threshold as the super-lactic threshold lies by definition exactly one threshold speed level above the lactic threshold.

The term "threshold speed" in the present context, is a new scientific term presented here by the inventors, and refers to relative effort or speed, with reference to the individual's speed thresholds. Threshold speed is the key to relating the actual speed to the heart rate curve.

The indicated 1:2:6:32 time ratio of transition points (T1:T2:T3:T4) only applies to speeds below the lactate threshold speed (VL).

Figure 4:
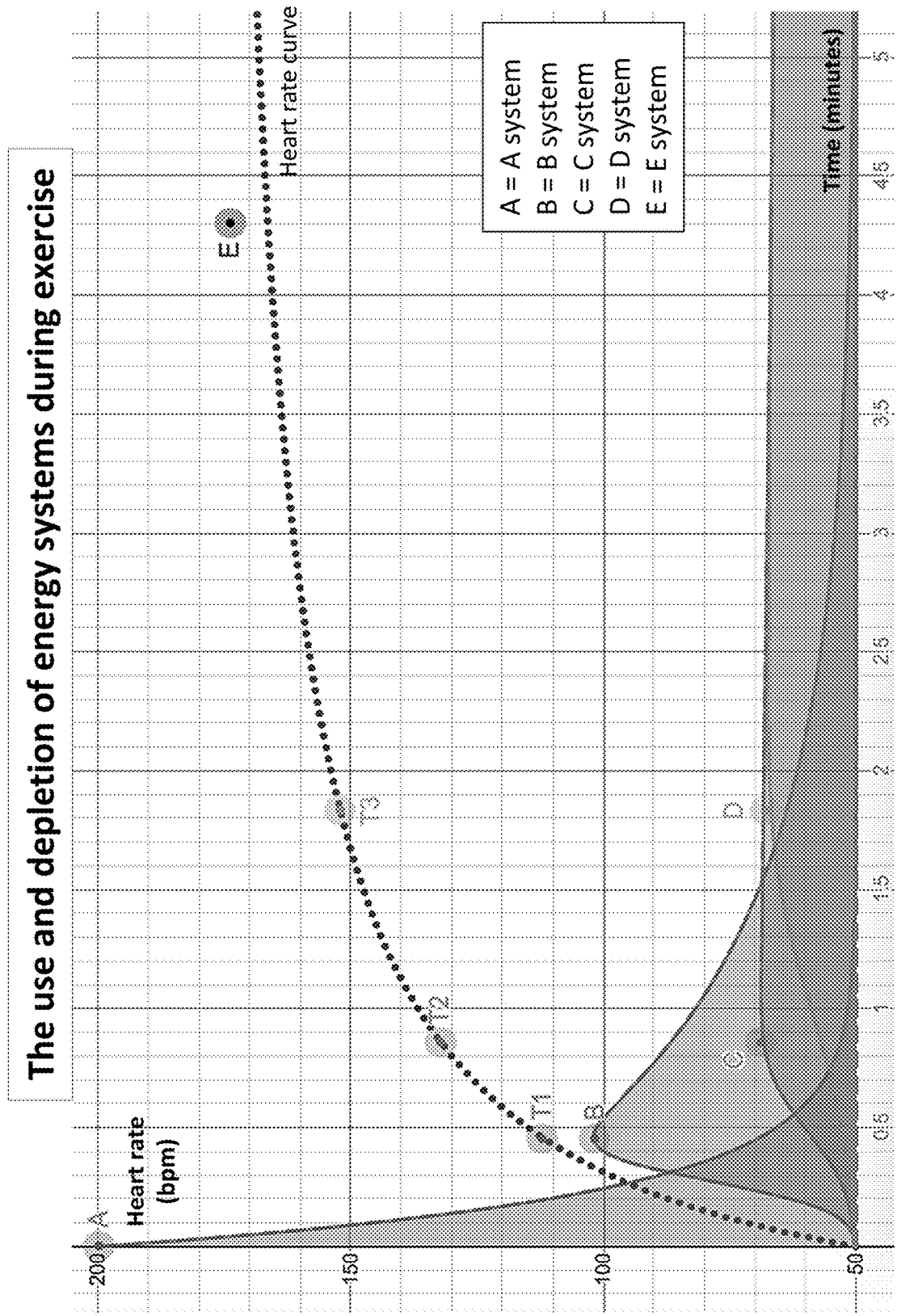

FIG. 4 shows the sequential, but overlapping, recruitment of different energy systems during a session of continuous exercise. The A, B, C, D and E systems (see text for details) are shown as shaded curves, while the heart rate curve is shown as a dotted line with transition points indicated (T1–T3).

Figure 5:
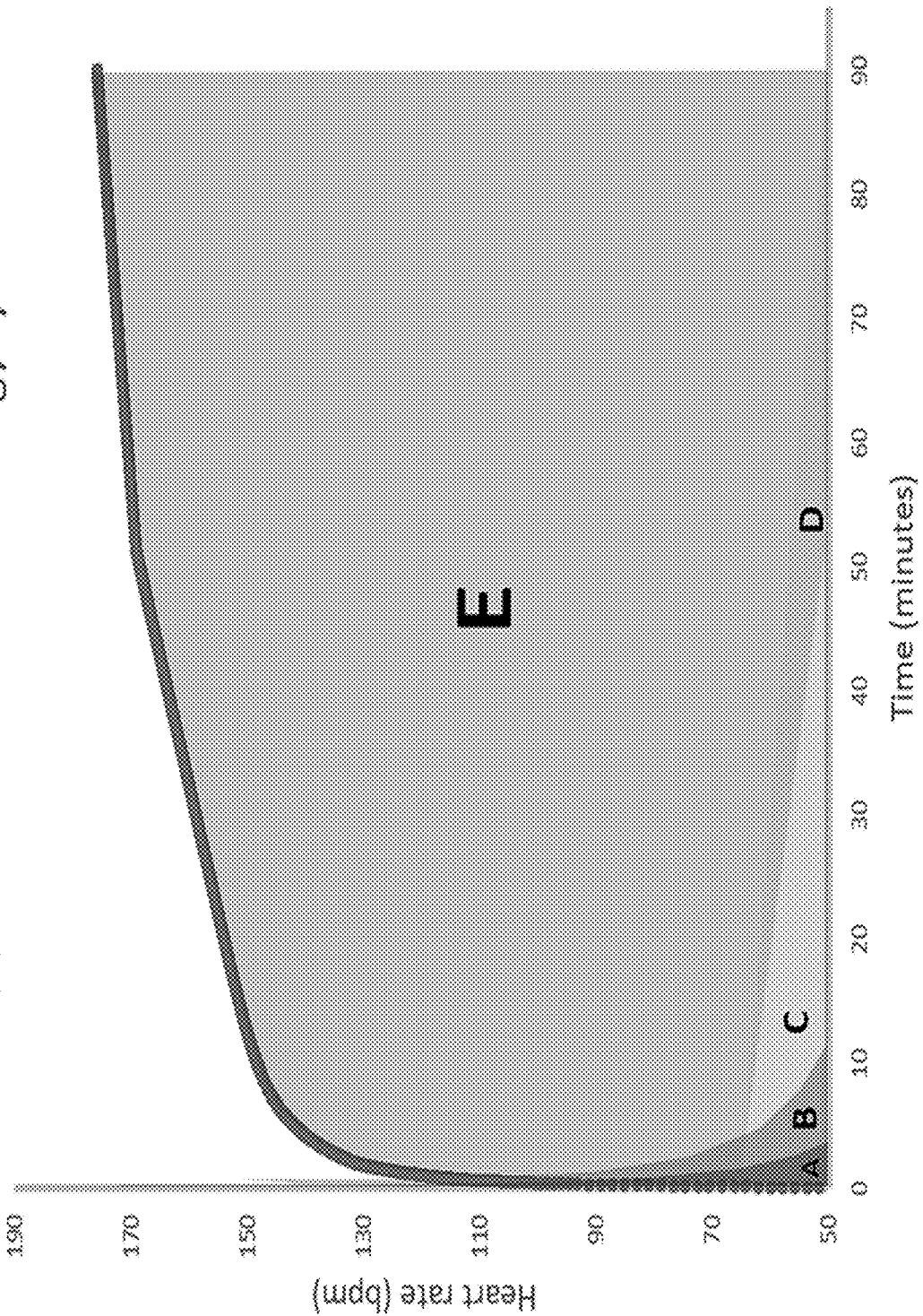

FIG. 5 shows the example from FIG. 4 on a longer time scale, from start to exhaustion. The marked, shaded areas show the contribution of the energy systems. The A, B, C and D-systems are depleted at the times of T3, T4, T5 and T6, respectively (not shown). The C and D systems are depleted linearly, while the A and B systems are depleted exponentially.

Figure 6:
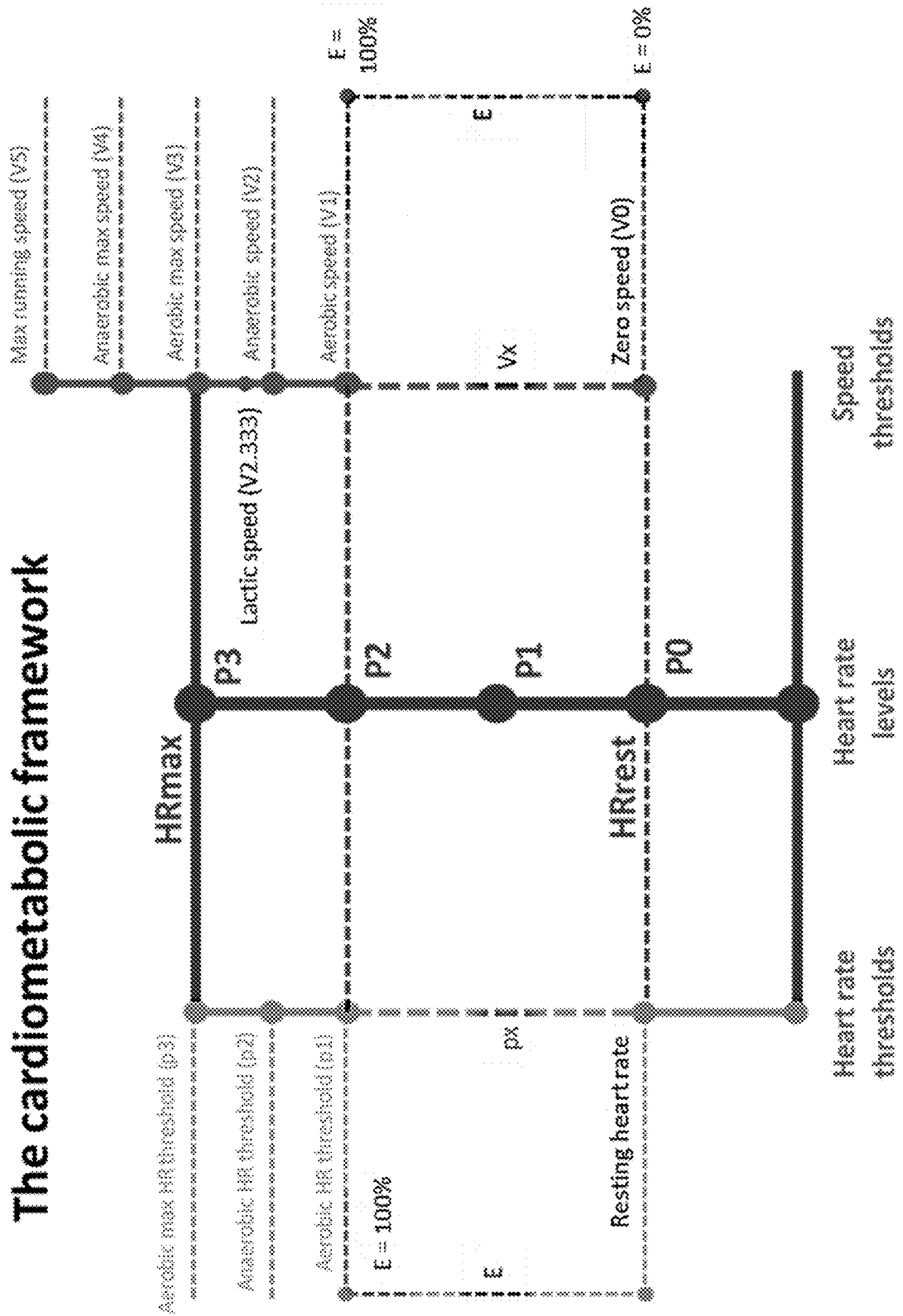

FIG. 6 shows a schematic illustration explaining the cardio-metabolic framework. The heart rate levels in the middle (P0-P3) are fixed on a central axis in quarterly alignment (i.e., evenly spaced), irrespective of endurance (E). The heart rate thresholds (p1-p3) and the speed thresholds (V1-V5) are connected to the main axis through p3 and V3, but the other speed and heart rate thresholds move up and down and are directly affected by the endurance. At E=0%, the p1 and V1 thresholds are minimized and aligned with the P0 heart rate level. At E=100%, the p1 and V1 thresholds are maximized and aligned with the P2 heart rate level.

Figure 7:
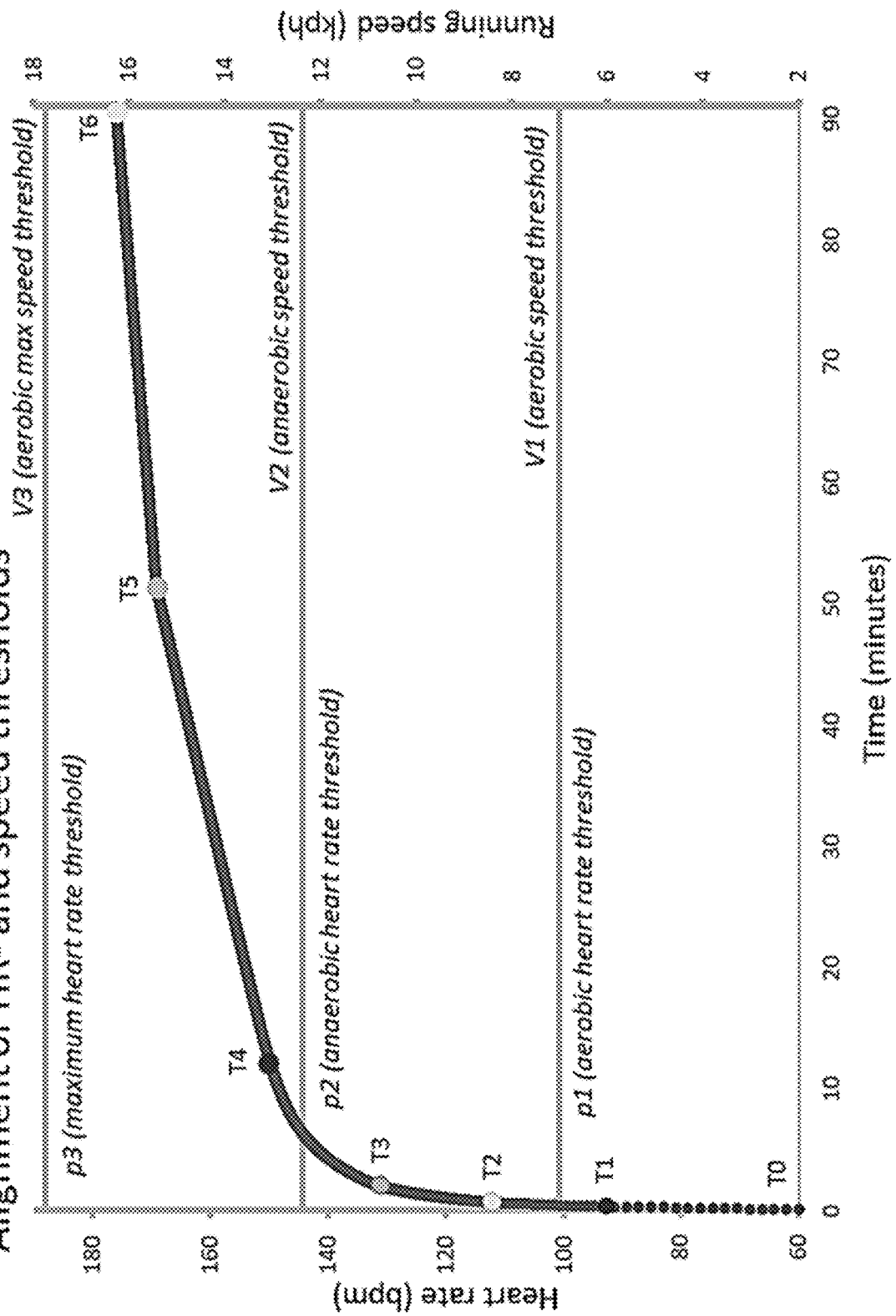

FIG. 7 shows the heart rate curve in the context of the cardio-metabolic framework. Solid horizontal lines show the vertical alignment of heart rate thresholds (p1-p3) on the primary vertical axis and speed thresholds (V1-V3) on the secondary vertical axis.

Figure 8:
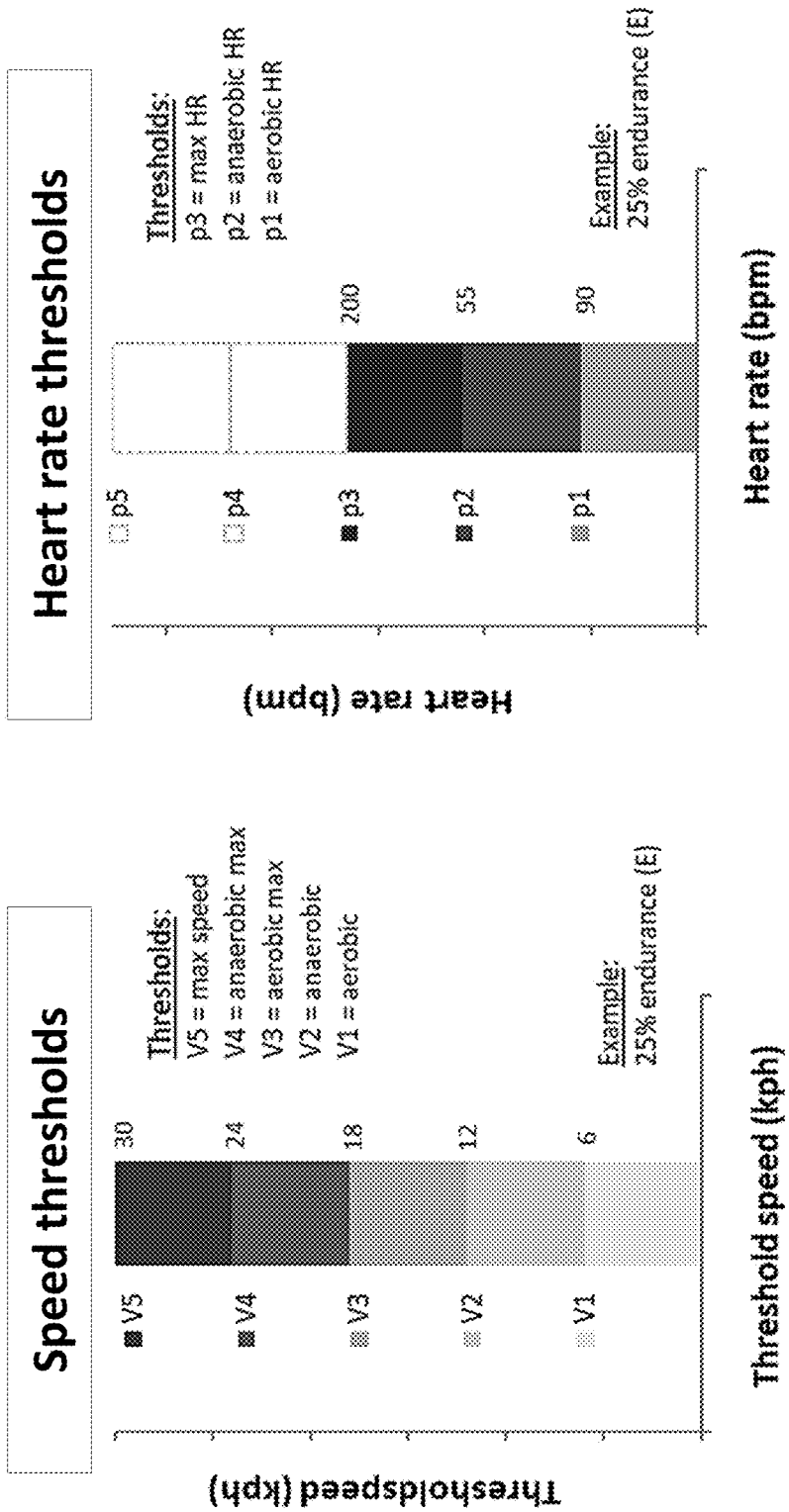

FIG. 8 presents an illustrative example showing speed thresholds and heart rate thresholds for an individual with a maximum running speed of 30 kph and an HRmax of 200 bpm. The non-physiological p4 and p5 heart rate thresholds are extrapolated for reference with the corresponding speed thresholds.

Figure 9:
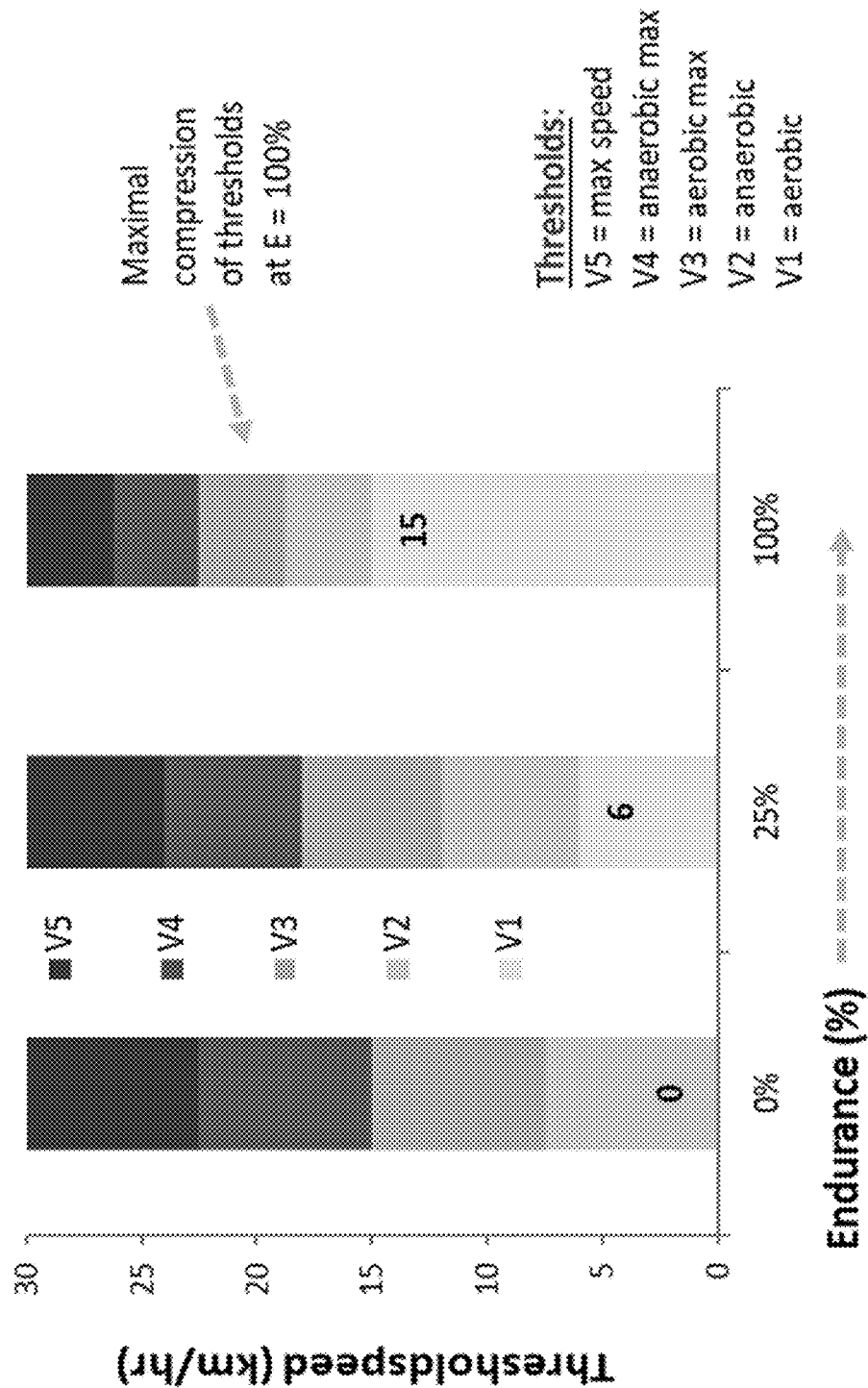

FIG. 9 shows illustrative examples of how aerobic endurance reflects the relative compression of speed thresholds. The three stacked columns represent speed thresholds at three different endurance levels (0%, 25% and 100%) but identical maximum running speed (30 kph).

Figure 10:
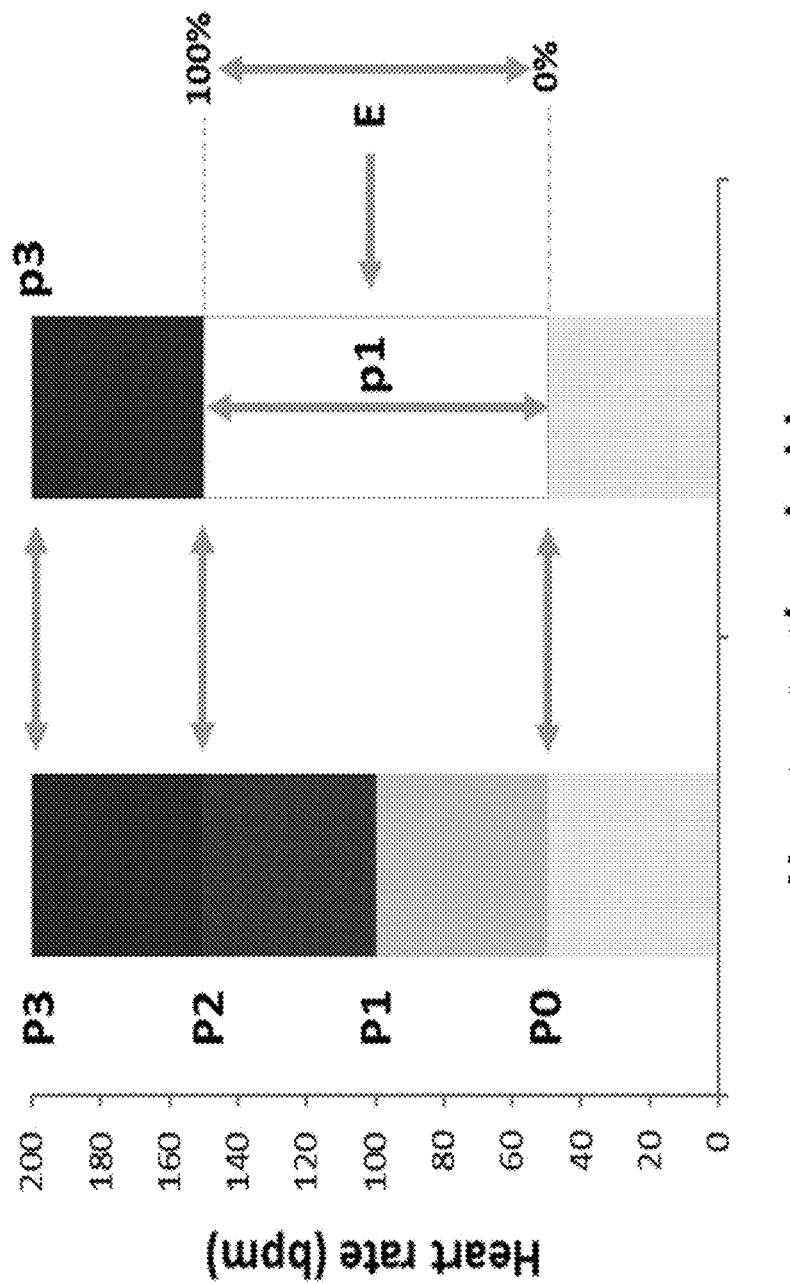

FIG. 10 shows an example of how aerobic endurance affects the relative compression of heart rate thresholds. The stacked column on the left represents the four fixed heart rate levels (P0-P3) in quarterly alignment with the maximum heart rate (P3). The stacked column on the right shows the effect of endurance (E) on the alignment of the heart rate thresholds (p1-3).

Figure 11:
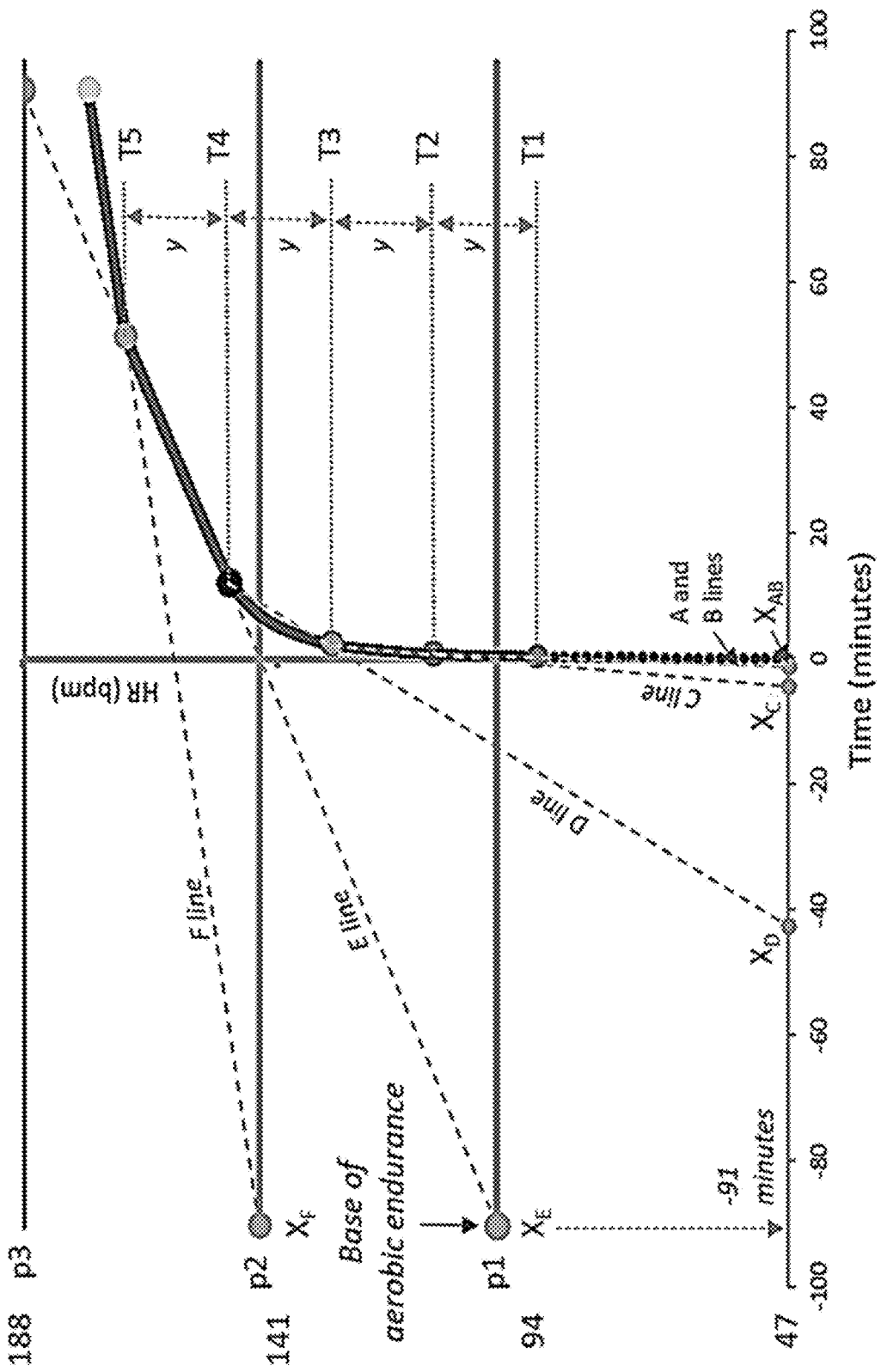

FIG. 11 shows an illustrative heart rate curve for an athlete exercising at constant speed from start to exhaustion. The graph shows how the base of each energy system can be identified through the linear tracing (A-F lines) of the transition points on the exercise-induced heart rate curve. The base of aerobic endurance can be read from the E line intercept ($X_E=X$) with the p1 threshold in negative time.

Figure 12:
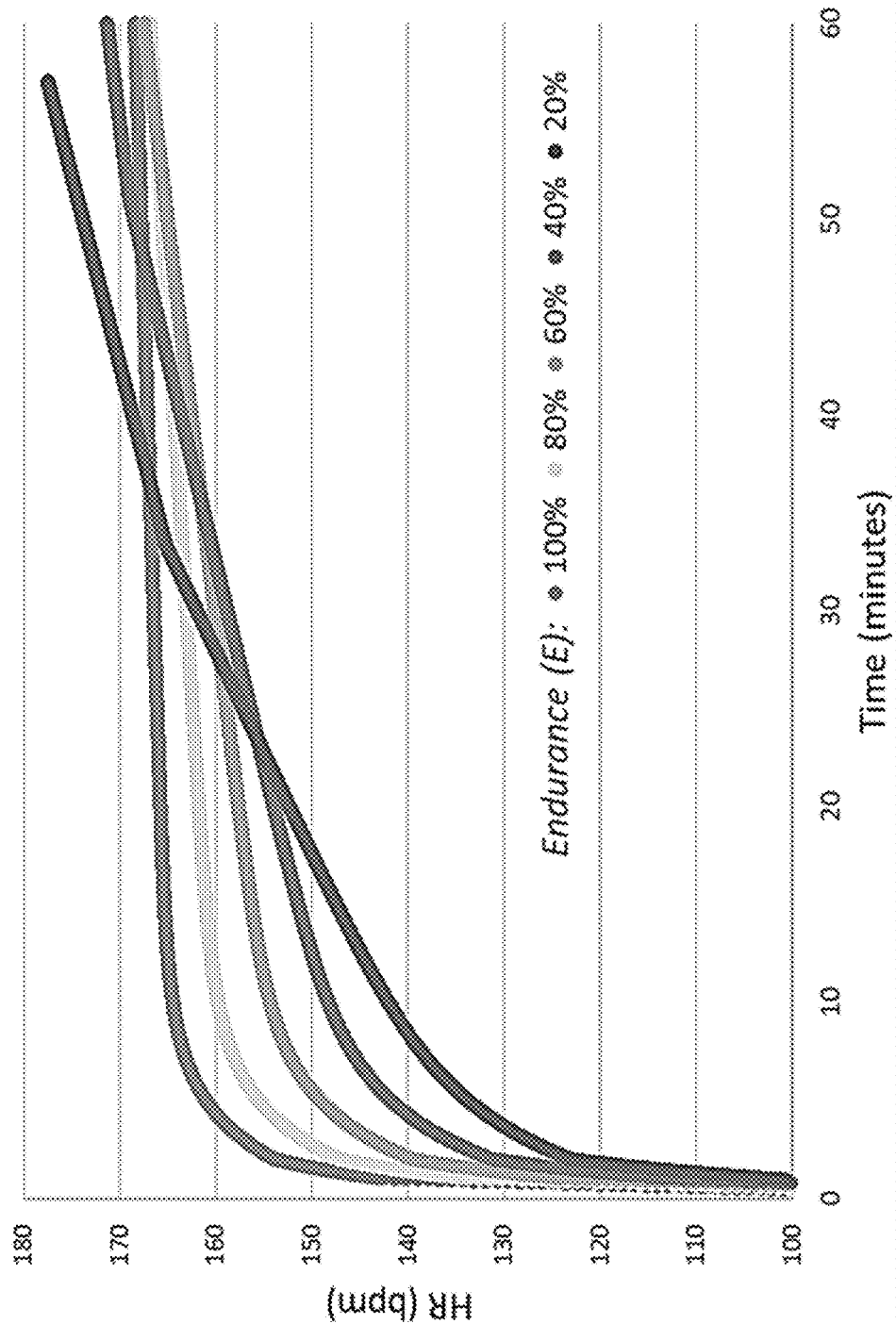

FIG. 12 shows the effect of endurance on the heart rate curve, showing heart rate curves generated at the same exercise intensity for different endurance levels but equal HRmax and maximum speed.

Figure 13:
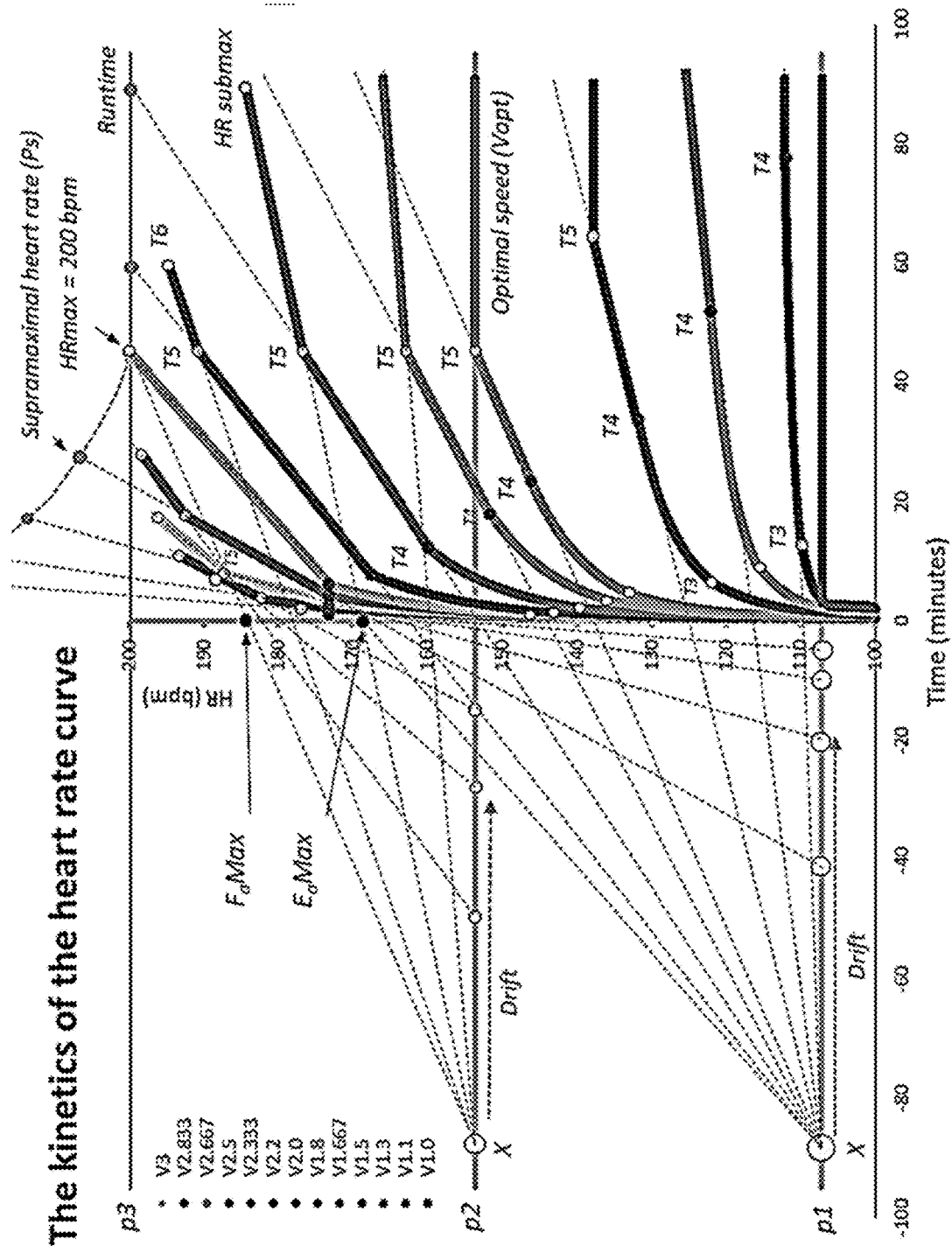

FIG. 13 explains how the kinetics of the heart rate activity curve are affected by relative exercise intensity (running speed). The graph shows heart rate curves for 13 different threshold speed (V) levels, from start to predicted voluntary exhaustion (shown for the seven highest speed levels).

Dashed lines show the forecast linear regression to the respective linear parts of each curve (E-lines and F-lines) and intercepts with the p1, p2 and p3 (HRmax) heart rate thresholds. X represents the base of aerobic endurance. The location of transition points T2–T6 is indicated. The supra-maximal heart rate is indicated above HRmax for two of the curves. The two solid circles on the y-axis indicate the maximum intercept positions of the E-lines and F-lines ($E_a$Max and $F_a$Max), at threshold speed levels V2.333 and 2.666, respectively.

Figure 14:
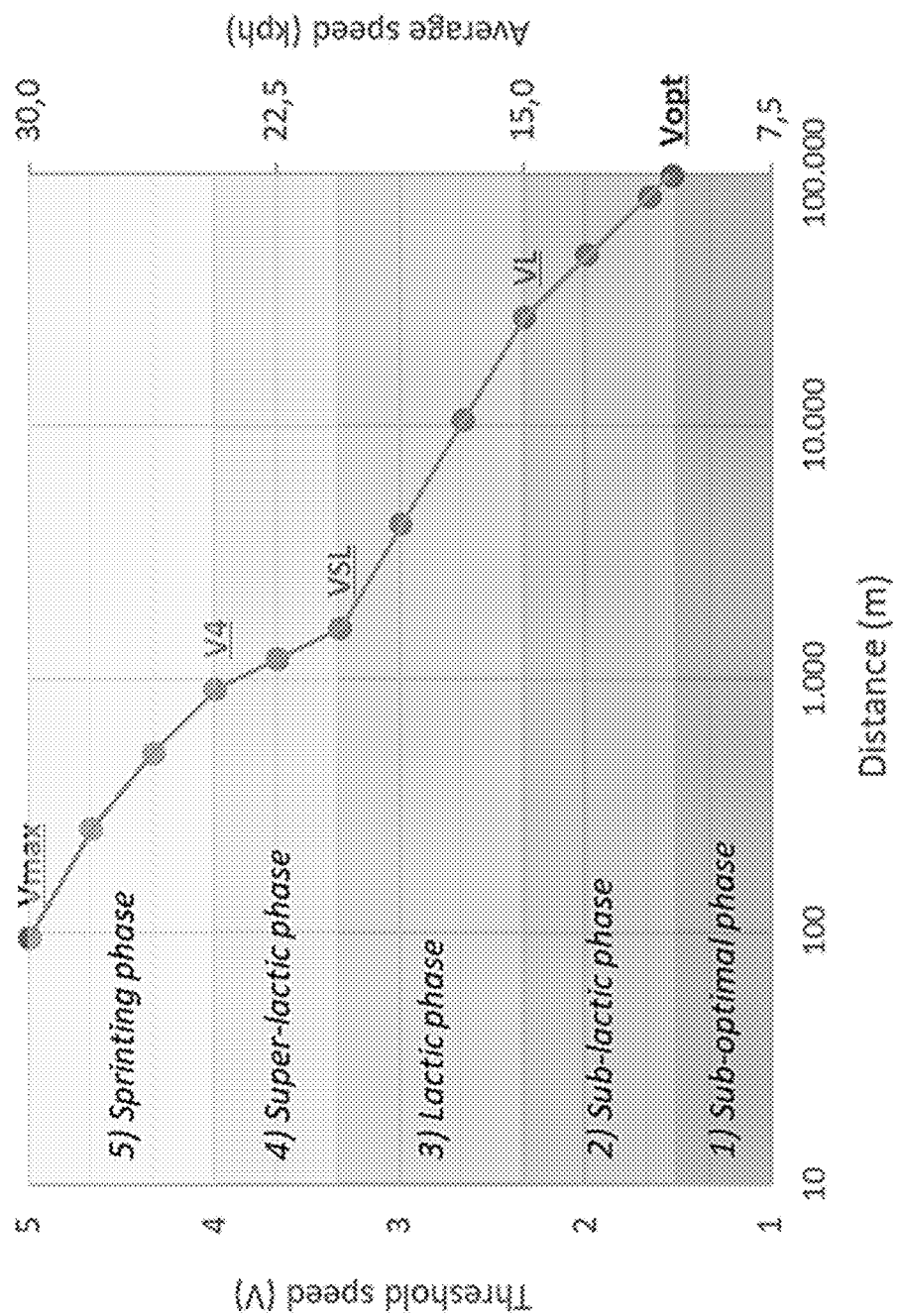

FIG. 14 shows an example relationship between running speed and maximum distance for that speed (the speed-distance relationship). The horizontal axis (log scale) shows the distance in meters, the primary vertical axis shows the threshold speed (V) and the secondary vertical axis shows the actual running speed. The points show the actual speed and distance at evenly spaced threshold speed levels. The five speed-distance phases are shown as shaded areas, separated at key speed thresholds (see text for details).

Figure 15:
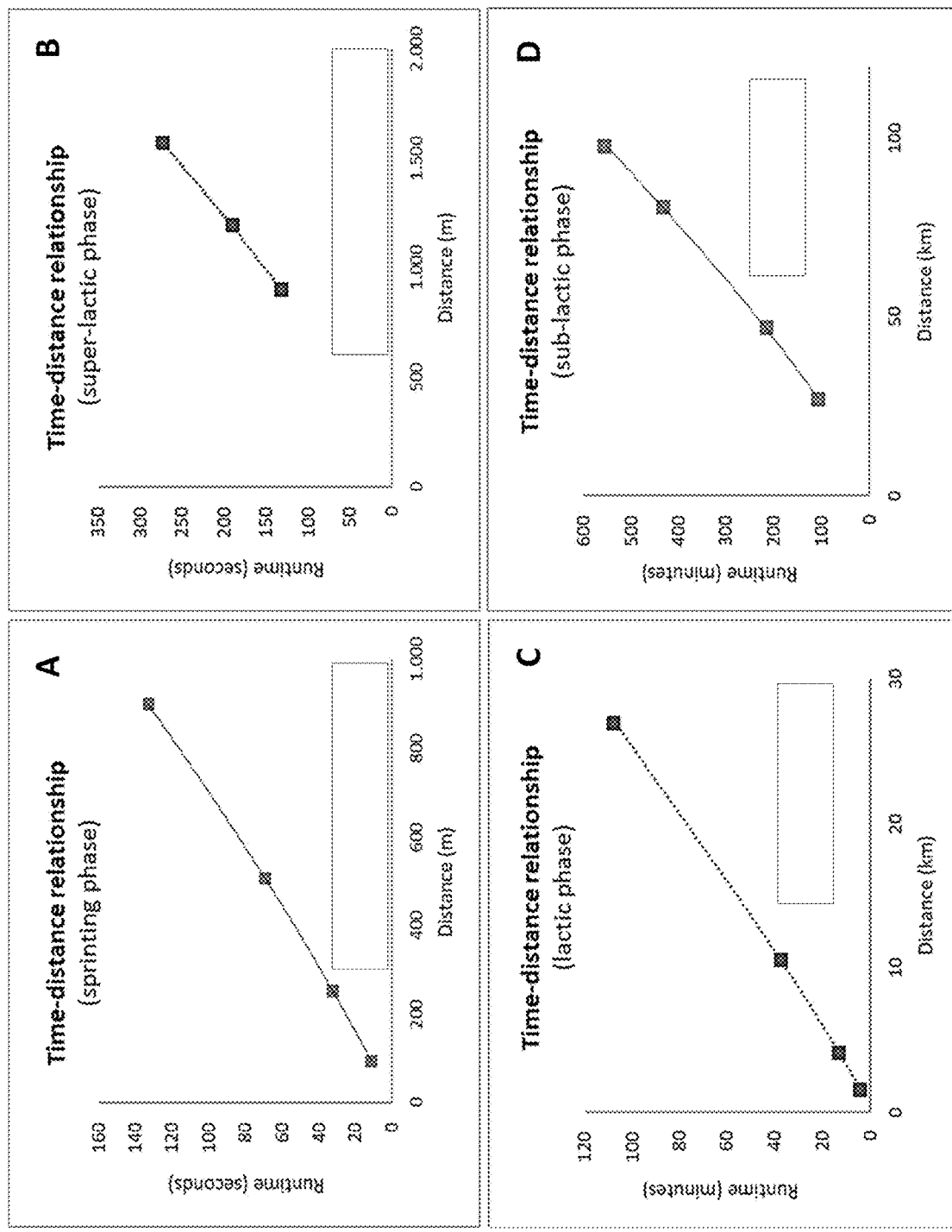

FIG. 15 shows the time-distance relationship during the four different distance phases, i.e. a) sprinting phase, b) super-lactic phase, c) lactic phase and d) sub-lactic phase. Exponential equations are indicated for phases b-d and a polynomial equation for phase a.

Figure 16:
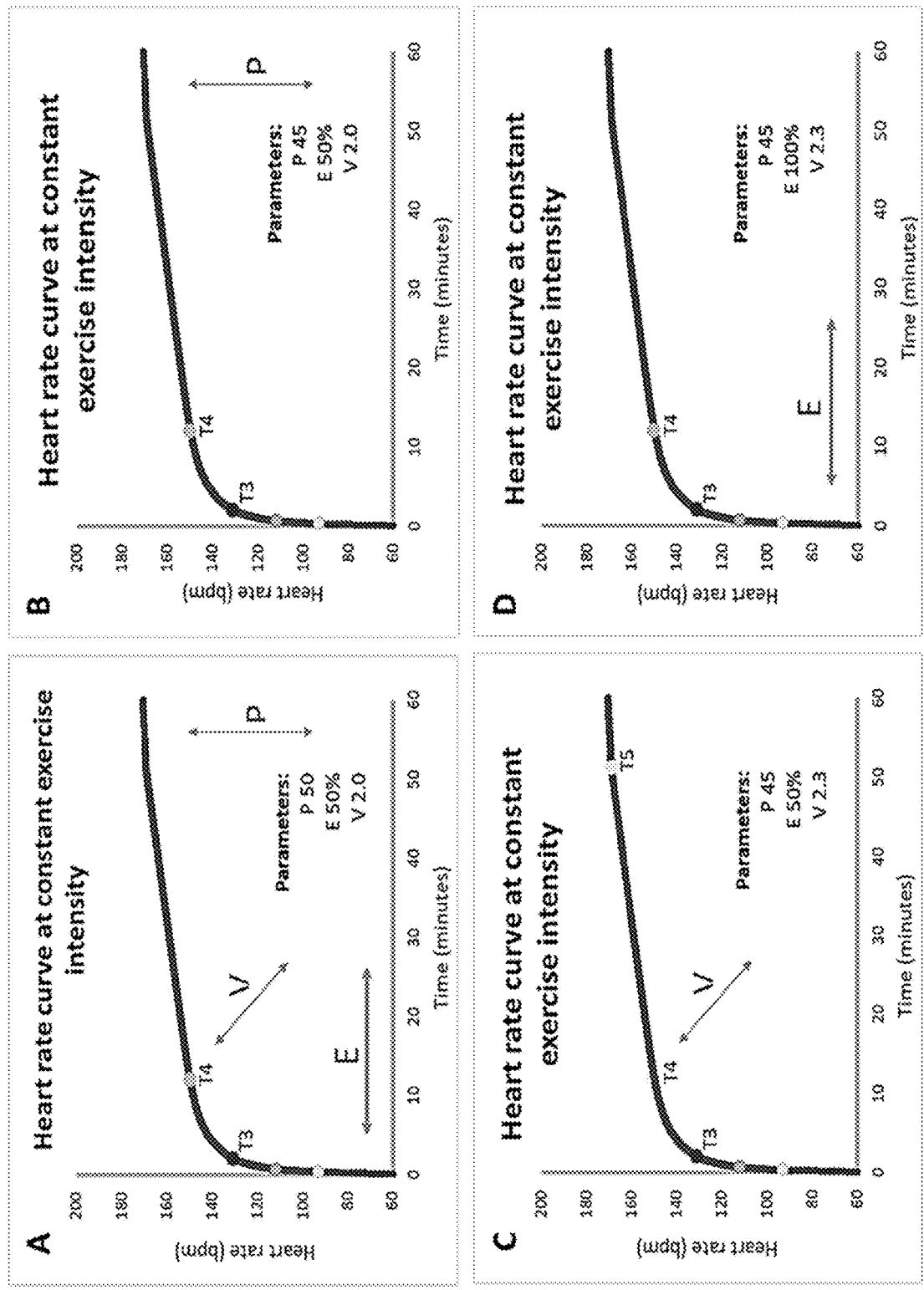

FIG. 16 presents an illustrative example showing the controlling effects of the three cardio-metabolic parameters, E, P and V, on the human heart rate curve produced during exercise of constant intensity (power output). The first graph (A) shows an illustrative heart rate curve and the three directional forces acting upon it. The other three graphs (B, C, D) show the vertical, diagonal and horizontal effects of the three parameters, E, P and V, respectively.

Figure 17:
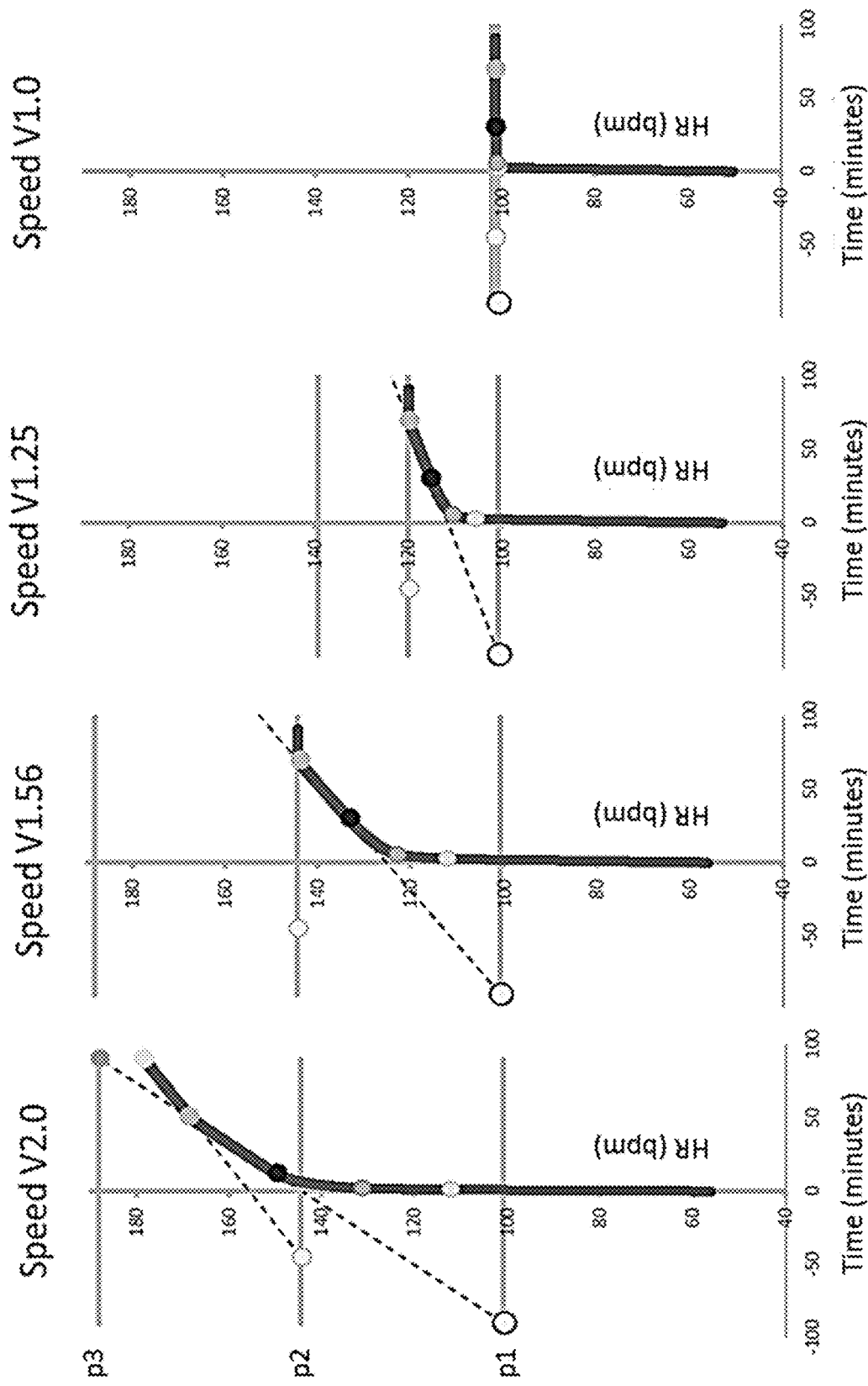

FIG. 17 shows the speed-related collapse of the heart rate framework. The four graphs (from left to right) show heart rate curves at descending speeds. The second graph shows the heart rate framework at the optimal speed (Vopt=V1.67), while the last two graphs show a collapsing framework at sub-optimal speeds. The last graph shows a flatline framework at V1.

Figure 18:
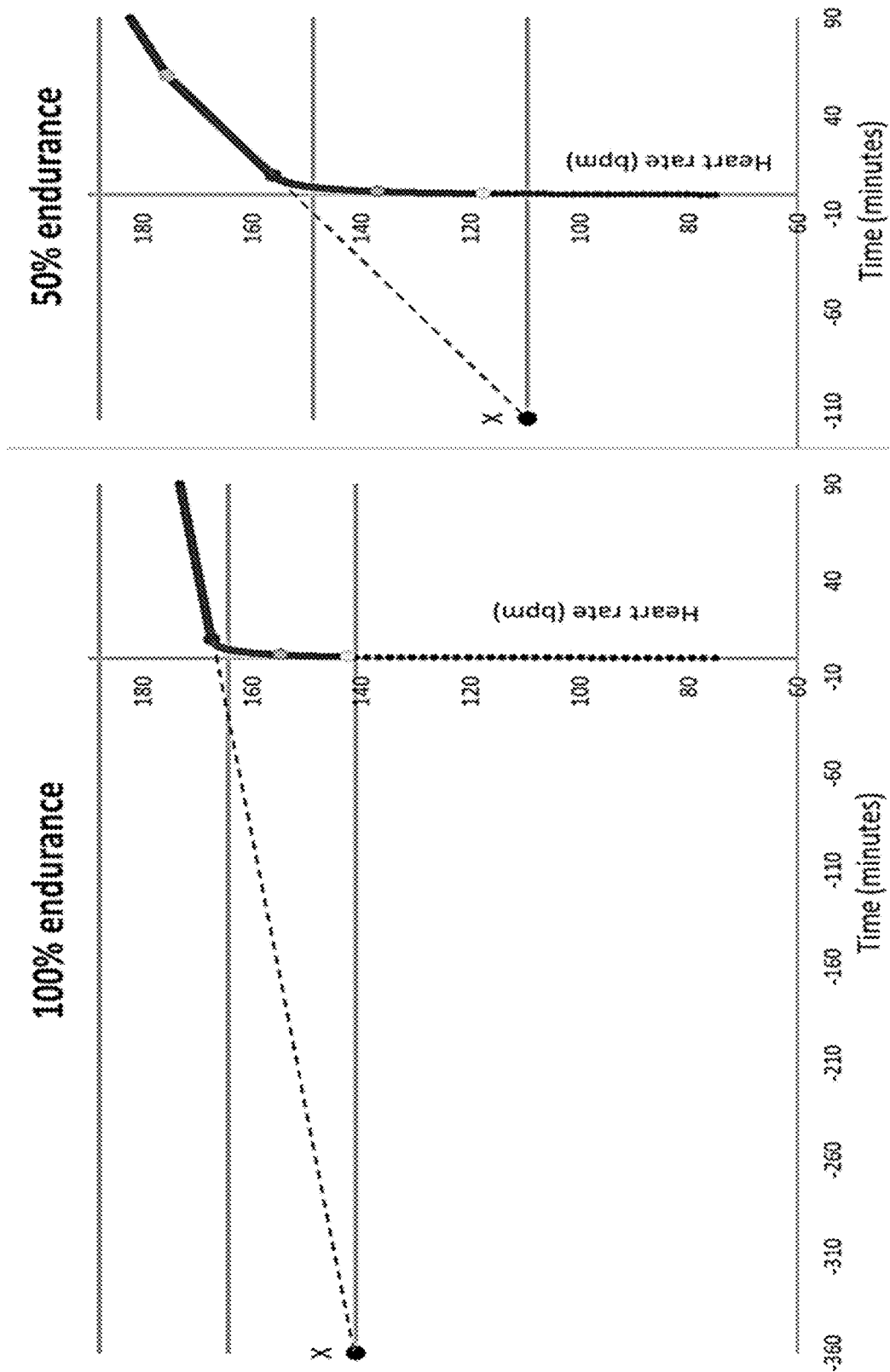

FIG. 18 shows the endurance-related compression of the heart rate framework. The five graphs show heart rate curves for five different endurance levels. The graphs show how the framework becomes wider (flatter curve) and more compressed with increasing endurance levels.

Figure 19:
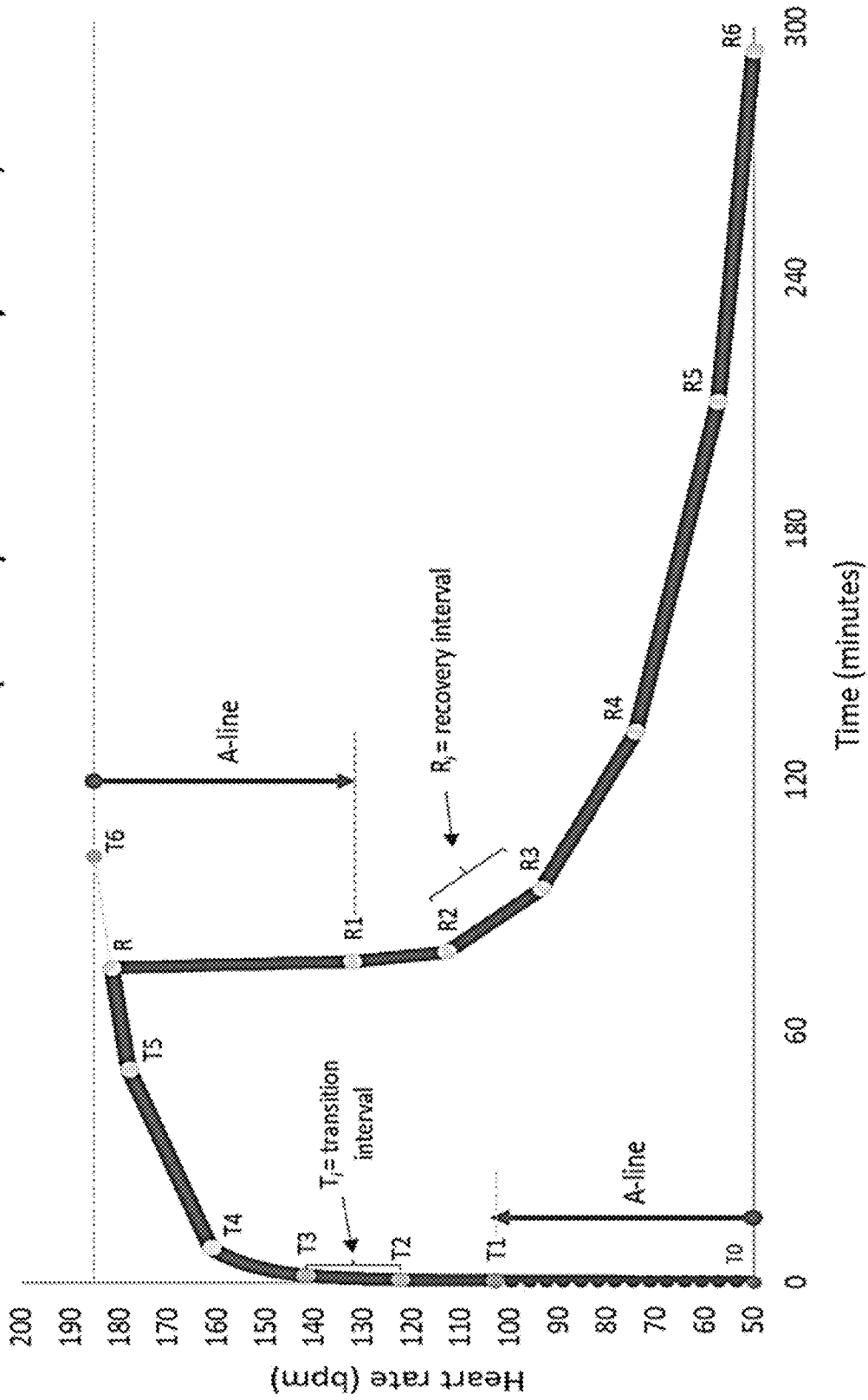

FIG. 19 shows an activity-induced heart rate curve and the associated passive recovery curve post-exercise, according to the invention. The indicated points on the curves represent the transition- and recovery points (T1–T5 and R1-R5; see text for details).

Figure 20:
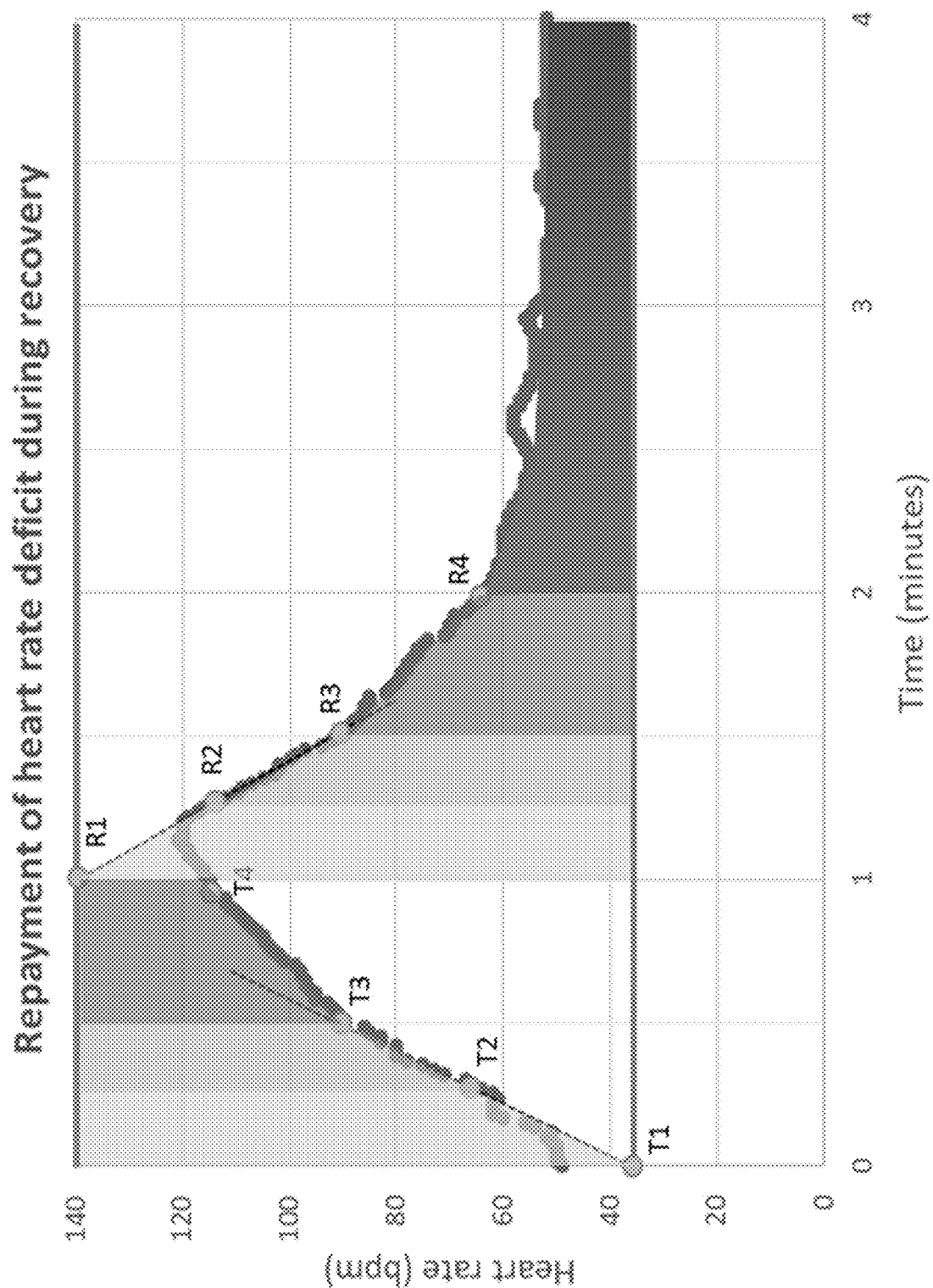

FIG. 20 explains the energy systems behind the heart rate recovery kinetics. The graph shows a connected activity- and recovery heart rate curve. The oxygen deficit and repayment are divided into the respective energy systems, as indicated by the shaded areas. For illustrative purposes, the shaded areas are not drawn entirely to scale (see text for details).

Figure 21:
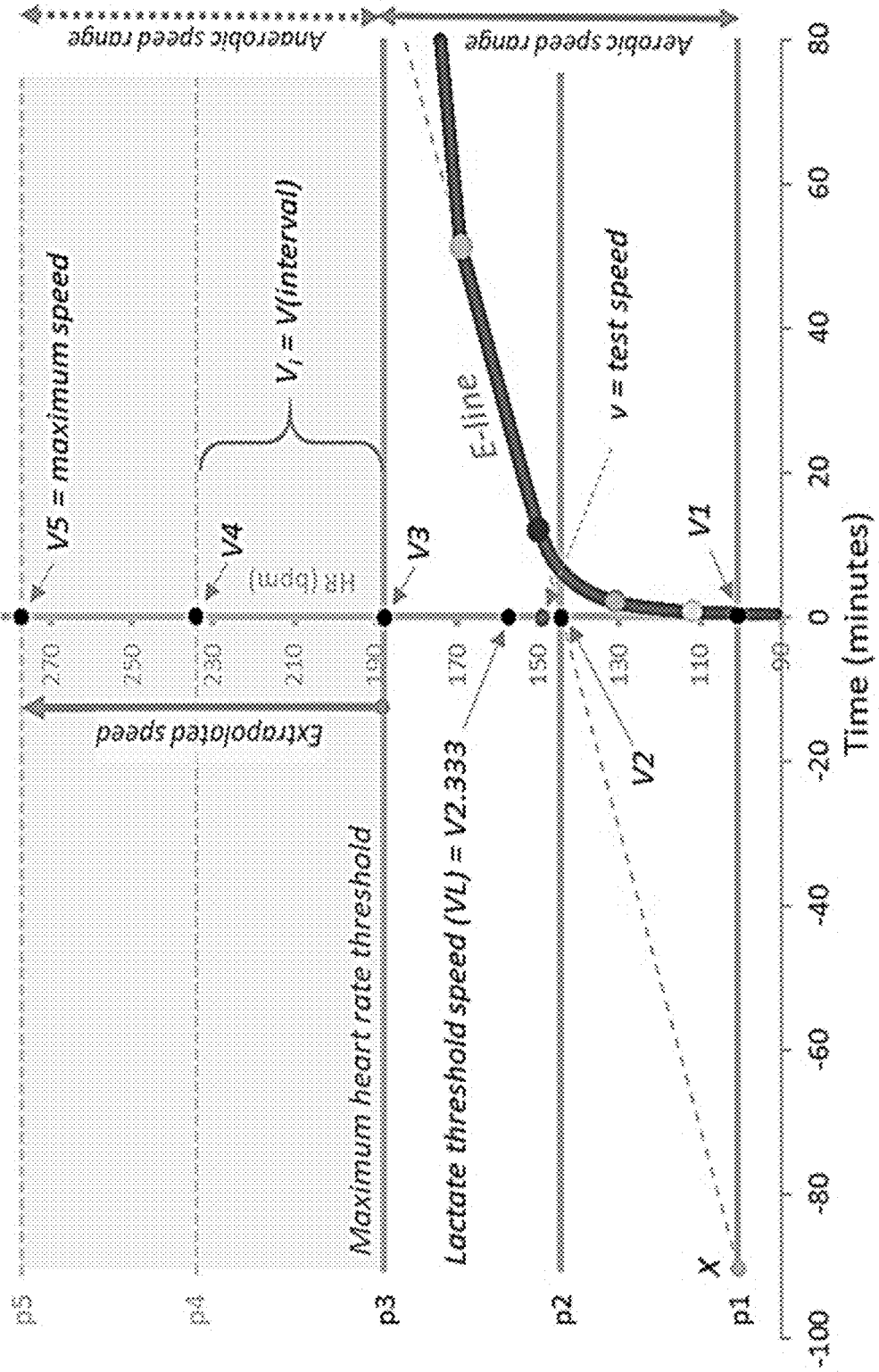

FIG. 21 shows the process of speed calibration, based on the alignment of actual test speed (v) against the calculated threshold speed in V-units. The V1-V3 speed thresholds (black dots) are aligned with the p1-p3 heart rate thresholds (grey lines), while the V4-V5 speed thresholds are calculated via extrapolation.

Figure 22:
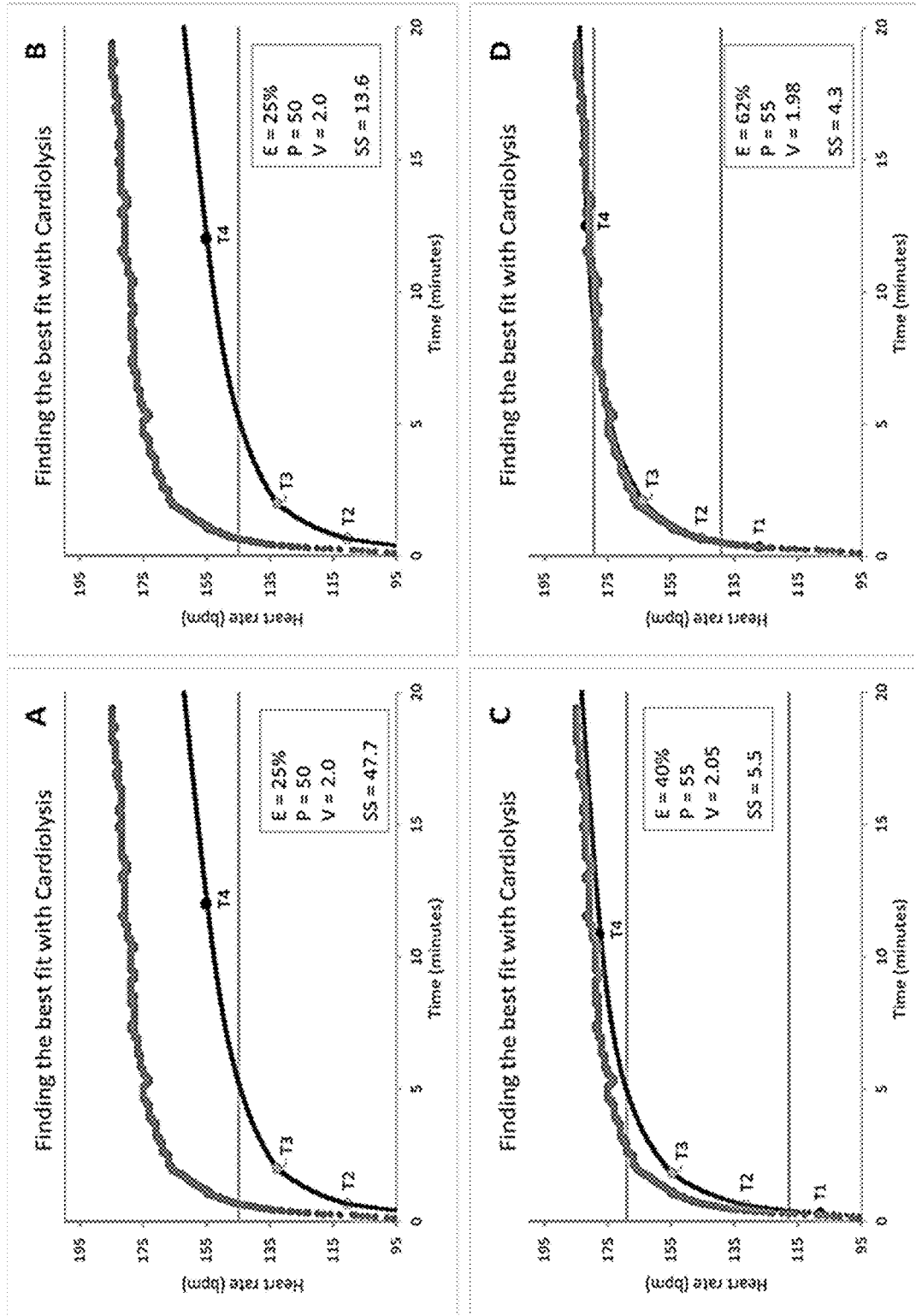

FIG. 22 provides an illustrative example explaining the iterative process of Cardiolysis. The four graphs (A-D) show four random stages of iteration towards minimizing the deviation (SS, sum of squared error) between the heart rate data and the model fit. The model finds the best fit to the data by adjusting the E, P and V parameters. The last graph (D) shows the fit producing the smallest error.

Figure 23:
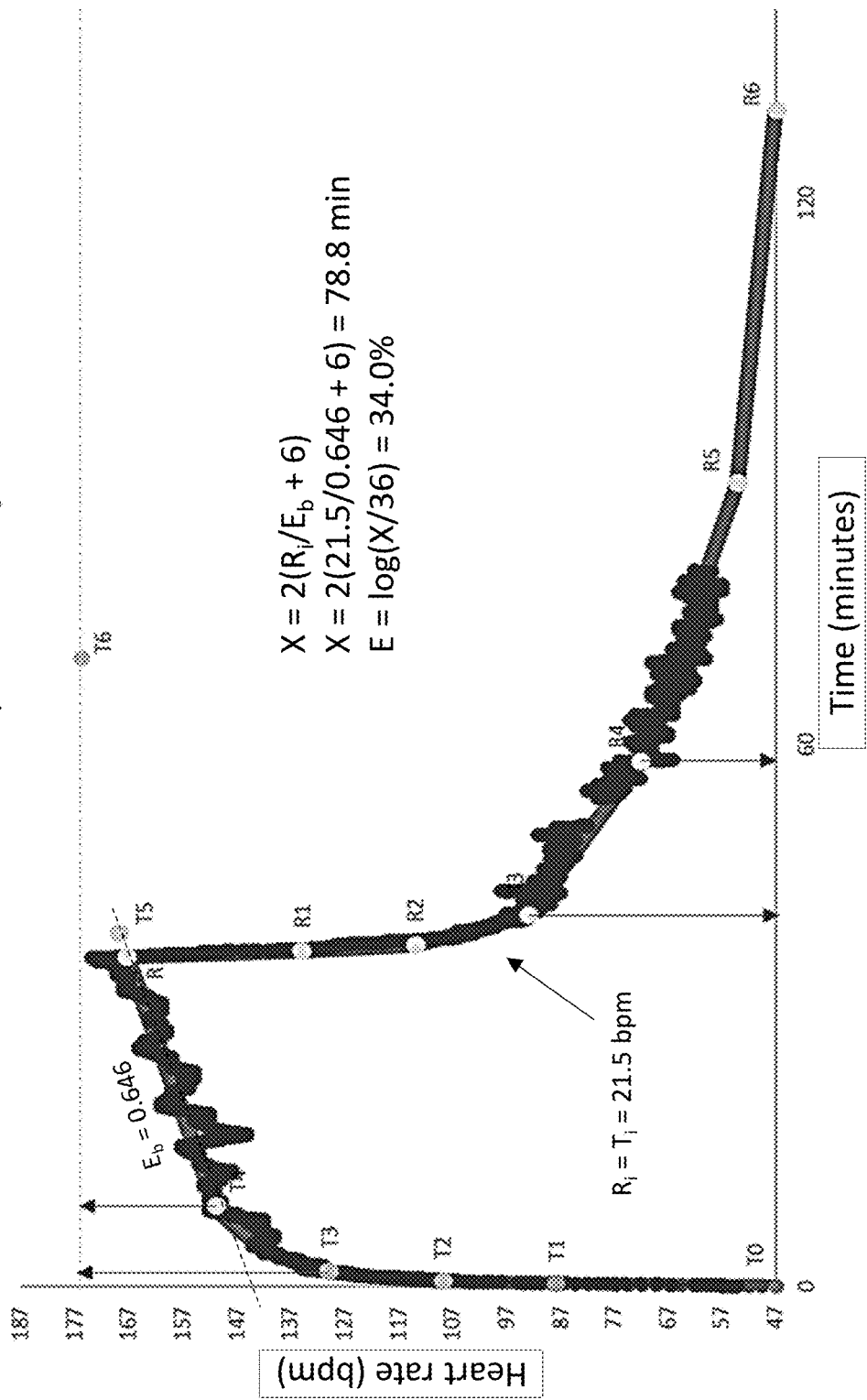

FIG. 23 shows the fitting and analysis of a sub-lactic exercise- and recovery test by the heart rate model (see text for details).

Figure 24:
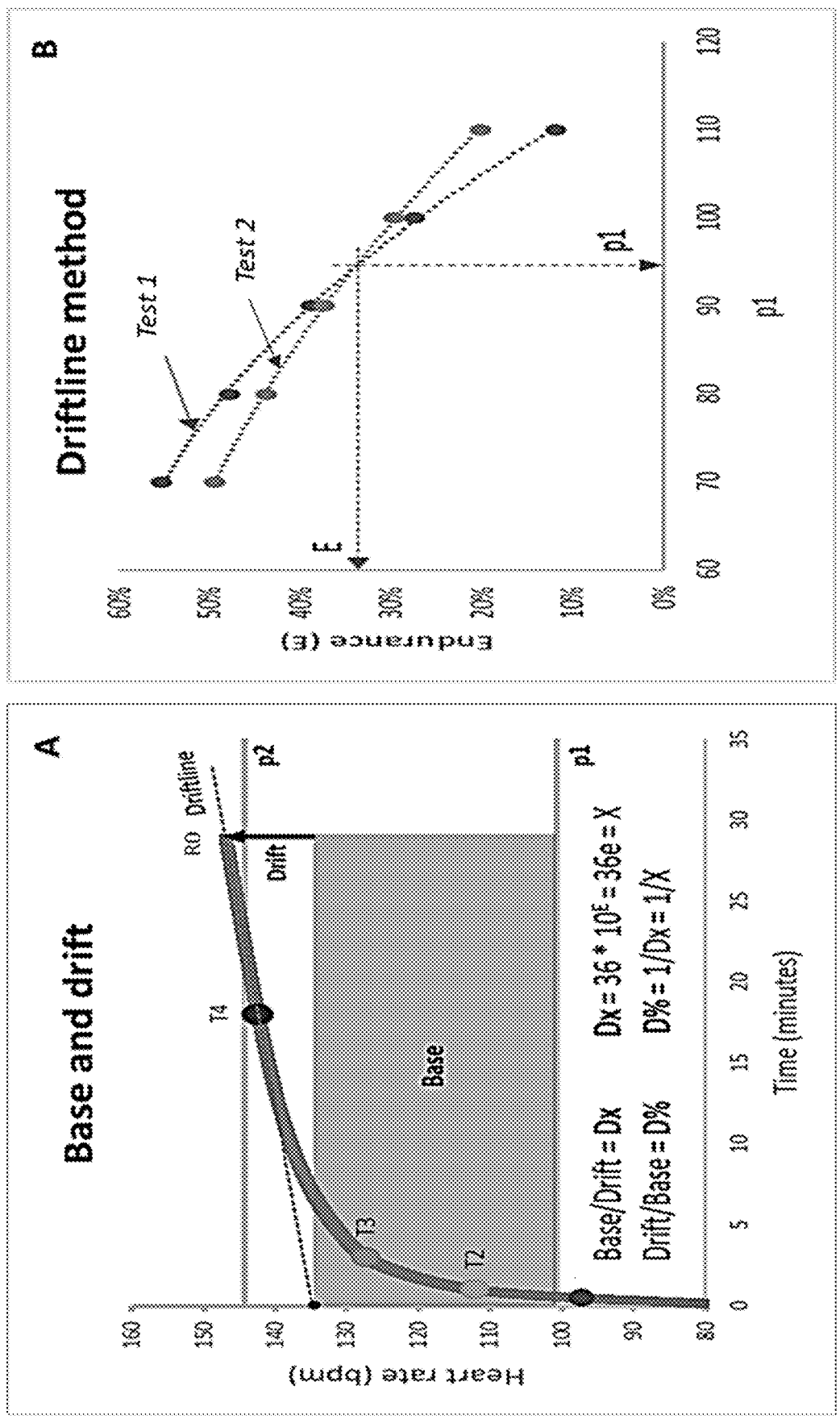

FIG. 24 shows the basis of the Driftline method. The first graph (A) shows the definition of the drift-ratio (Dx) and how the ratio equals the base time of aerobic endurance (X). The second graph (B) shows how E and p1 are identified from the analysis of two different tests (see text for details).

Figure 25:
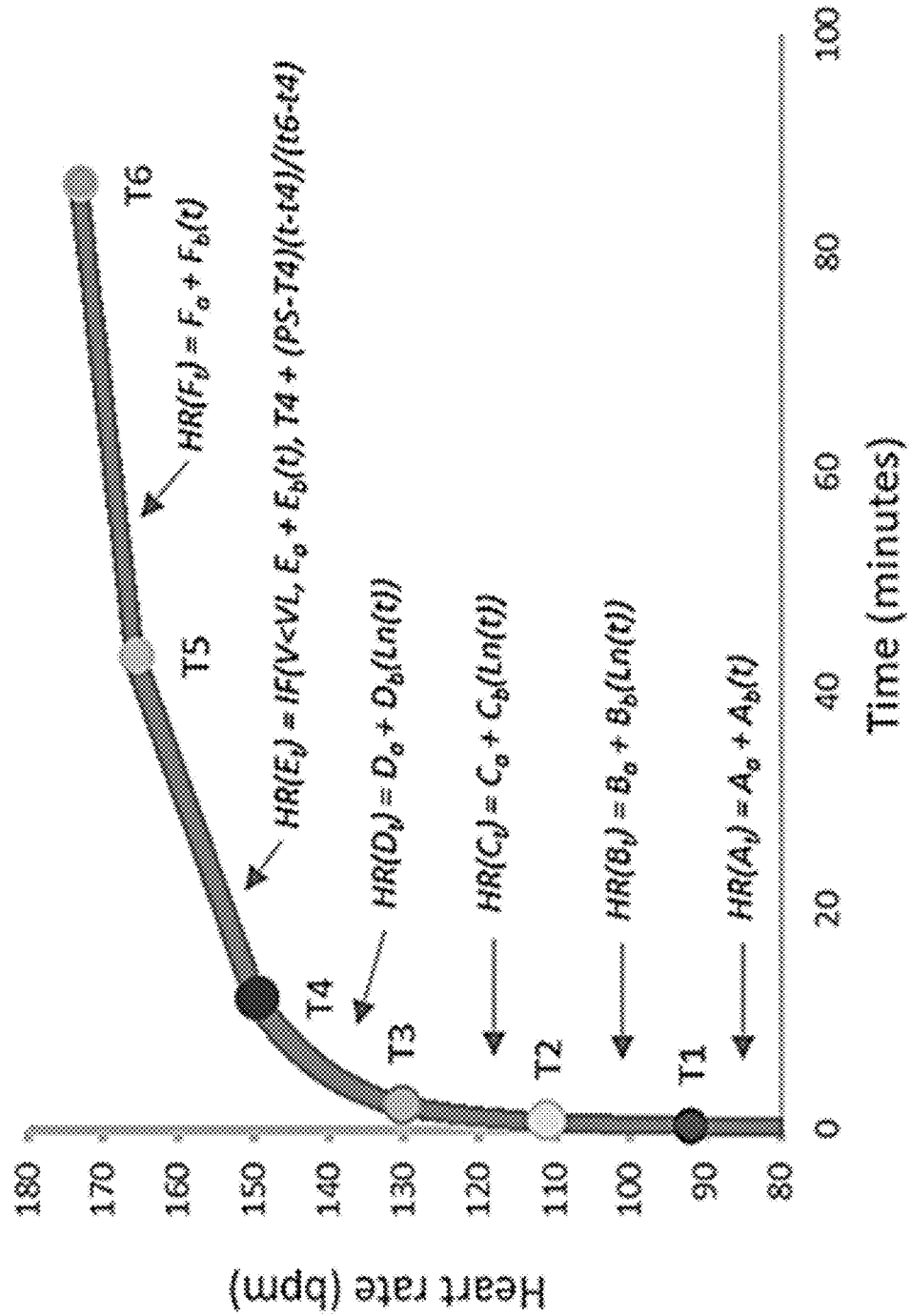

FIG. 25 shows an illustrative heart rate curve generated by the heart rate model. The heart rate curve is simulated through specific heart rate vs time functions for each of the six different components of the heart rate curve. The functions for the A-F components are presented as $HR(A_t)$, $HR(B_t)$, $HR(C_t)$, $HR(D_t)$, $HR(E_t)$ and $HR(F_t)$, respectively.

Figure 26:
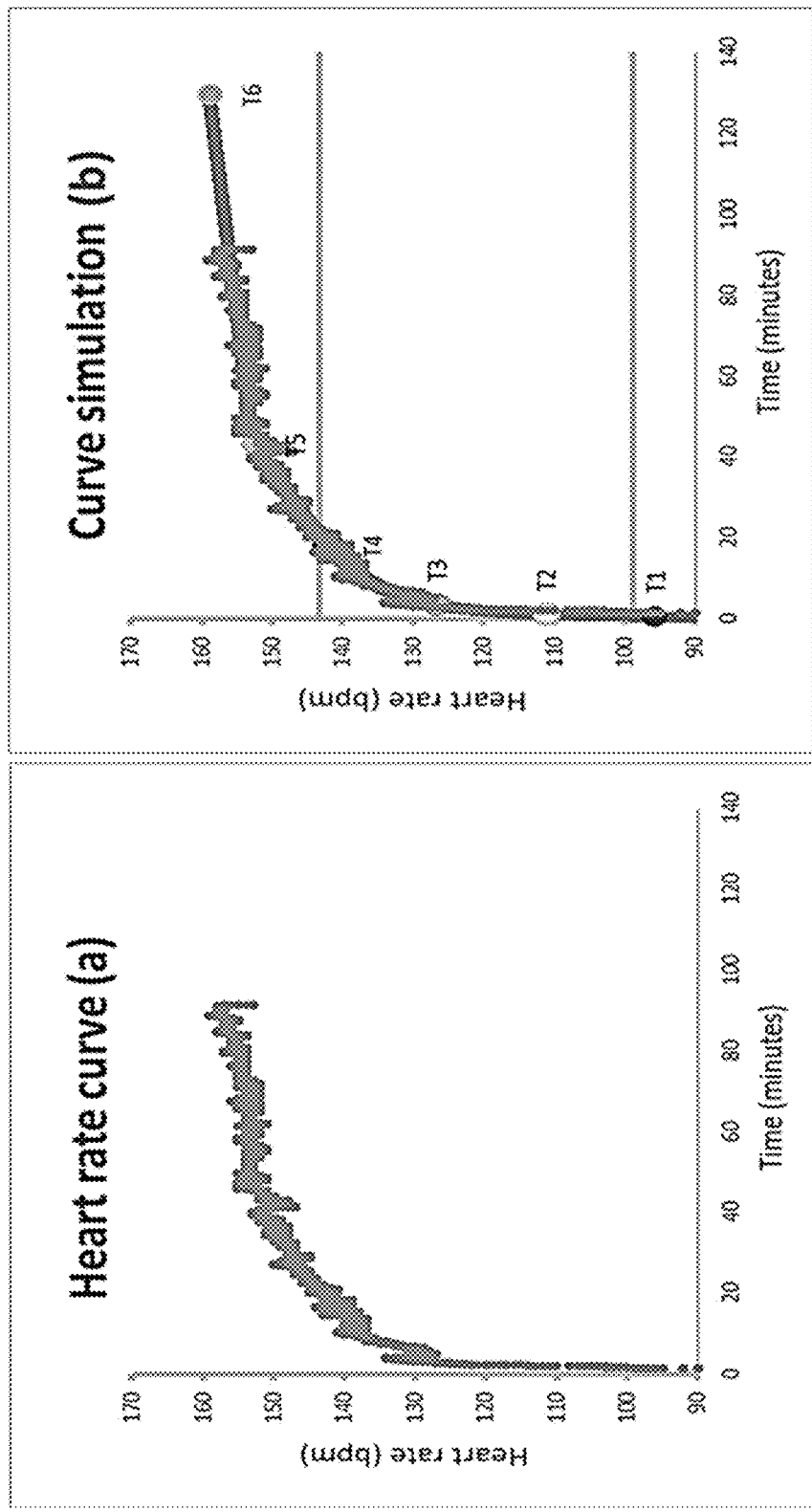

FIG. 26 shows the heart rate curve simulation to a set of actual heart rate data. The first graph (a) shows the heart rate data and the second graph (b) shows the simulated heart rate curve.

Figure 27:
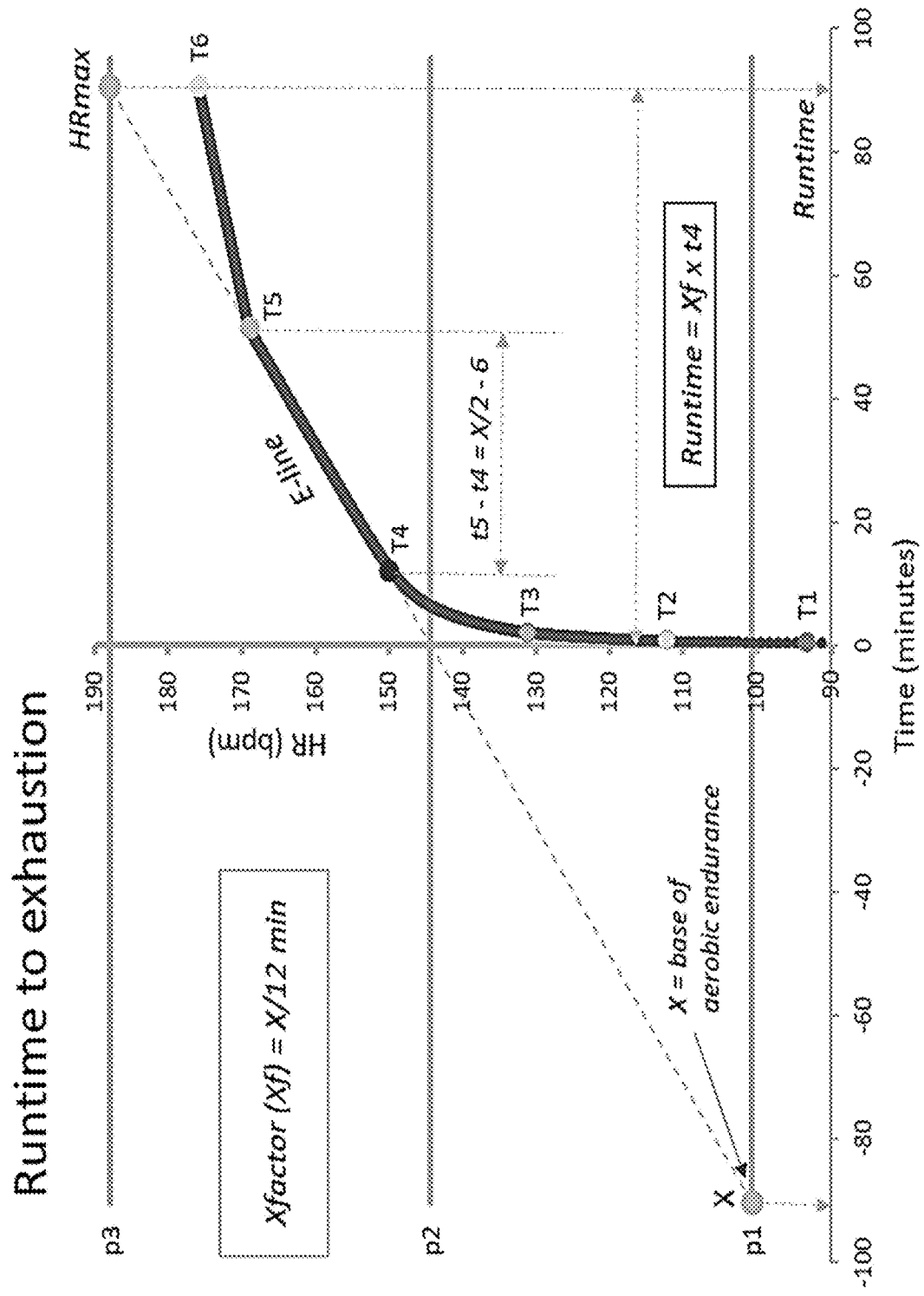

FIG. 27 provides an example showing the calculations of Runtime, i.e. the maximum running time to voluntary exhaustion at specific aerobic running speeds.

Figure 28:
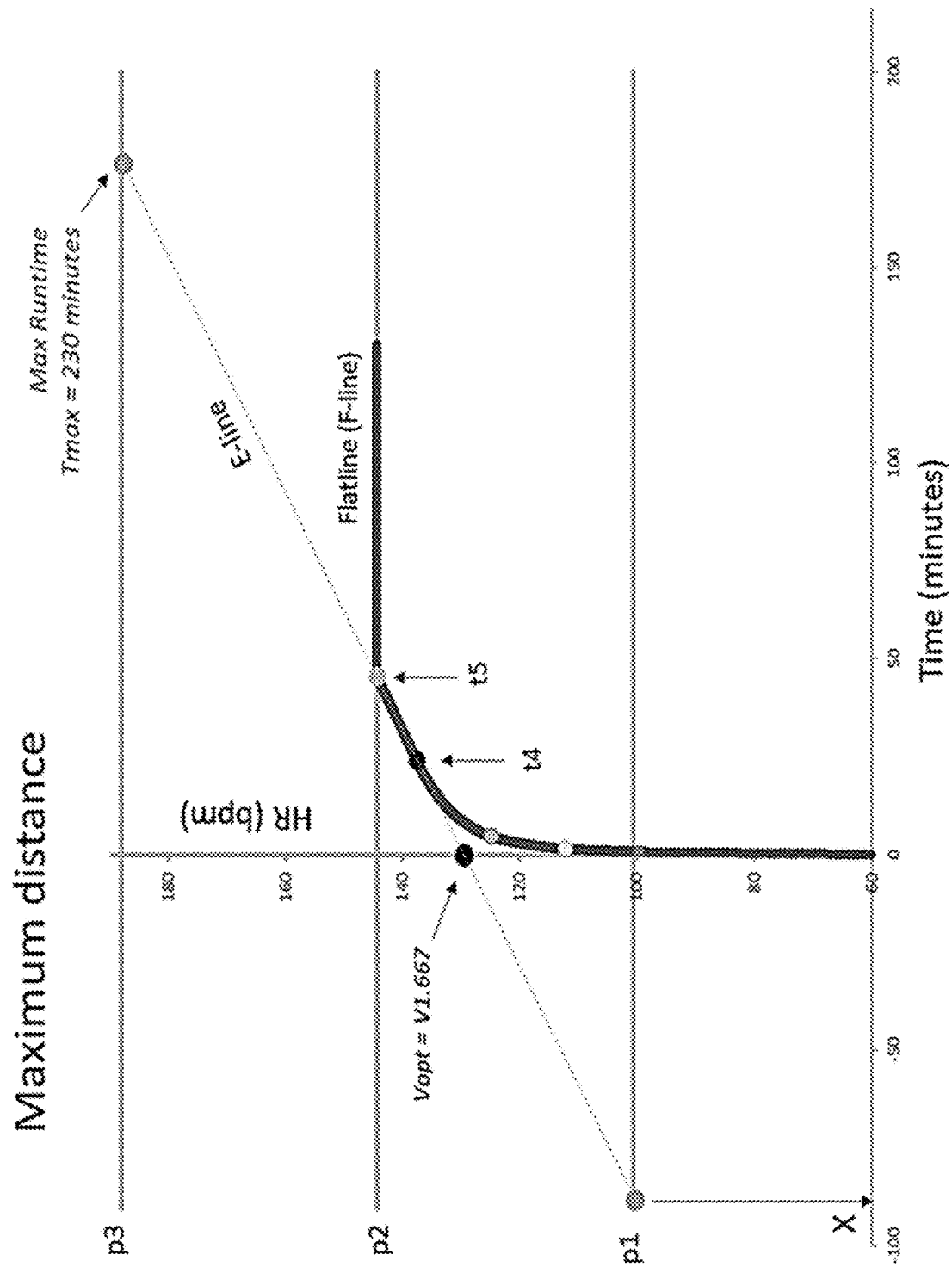

FIG. 28 shows an example of the calculation of max running distance (Dmax) for a runner with E=40%, Vmax=30 kph and HRmax=188 bpm. A maximum distance of 36.5 km can be reached when running at optimal speed (Vopt=V1.667), which equals 12.1 kph in this case.

Figure 29:
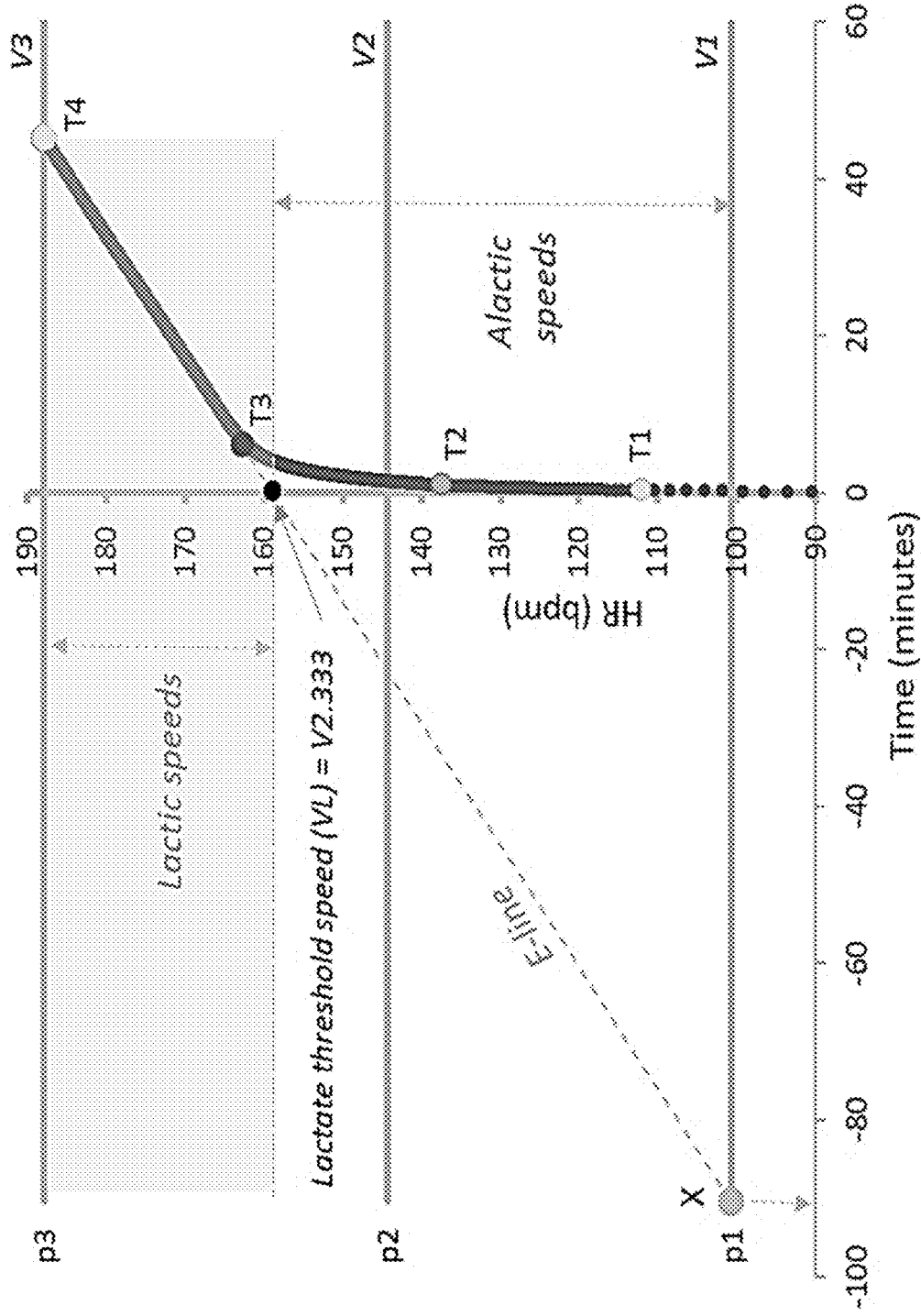

FIG. 29 shows an example of the calculation of the lactate threshold speed (VL) for a runner with E=40%, Vmax=30 kph and HRmax=188 bpm. When running to exhaustion at VL speed, the heart rate peaks as T5 at the p3 heart rate threshold. The lactate threshold speed equals the threshold speed V2.333 and occurs at the threshold heart rate p2.333.

Figure 30:
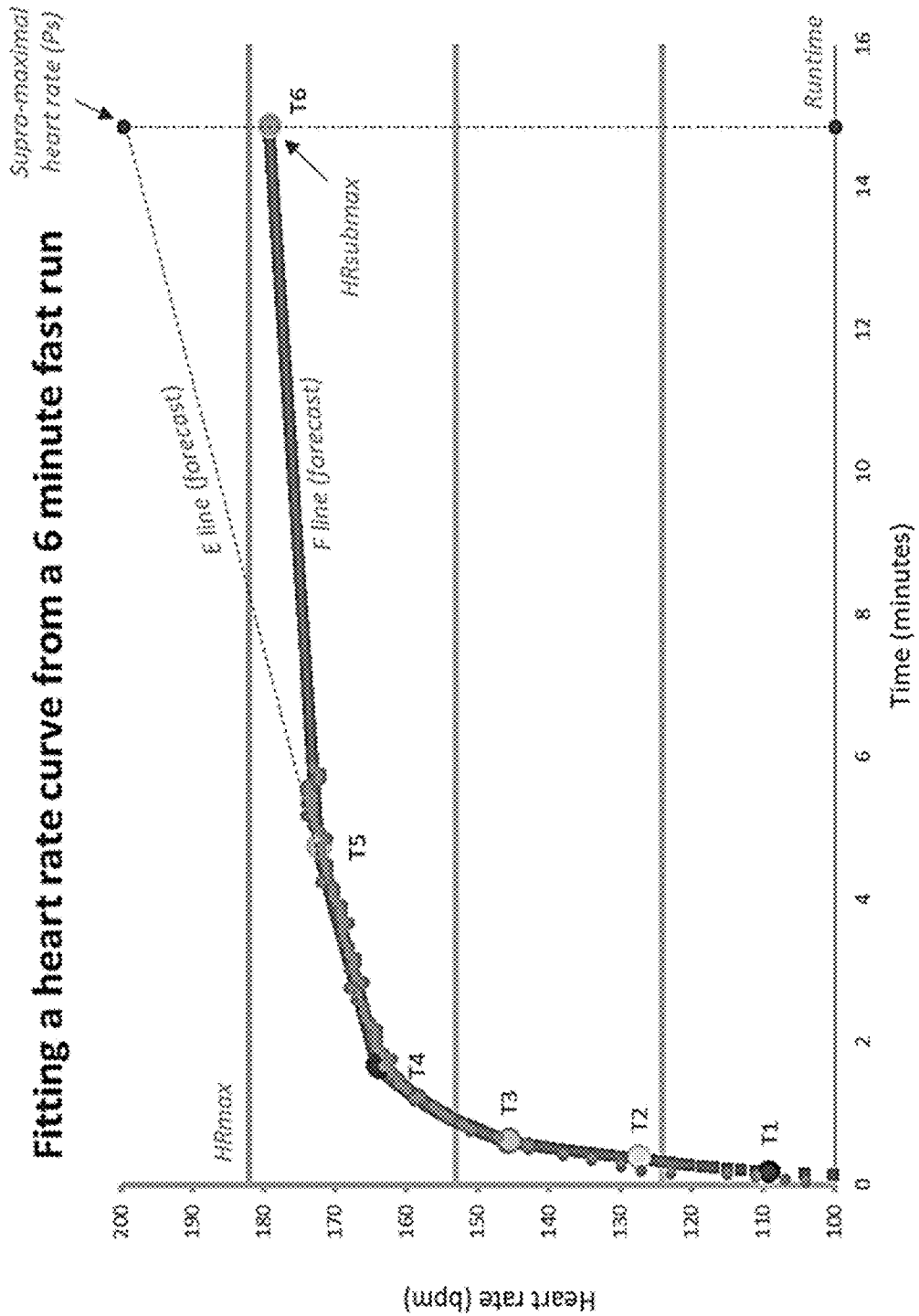

FIG. 30 shows the fitting of a heart rate curve produced by an endurance runner, running on a treadmill at a constant lactic speed (16.5 kph) for 6 minutes. Transition points (T1–T6) are indicated and the E-line is extrapolated (dashed line) to the supra-maximal heart rate endpoint PS at the maximum running time (Runtime). The F-line is extrapolated to the T6 endpoint, which equals a HRsubmax, about 3 bpm lower than the actual HRmax.

Figure 31:
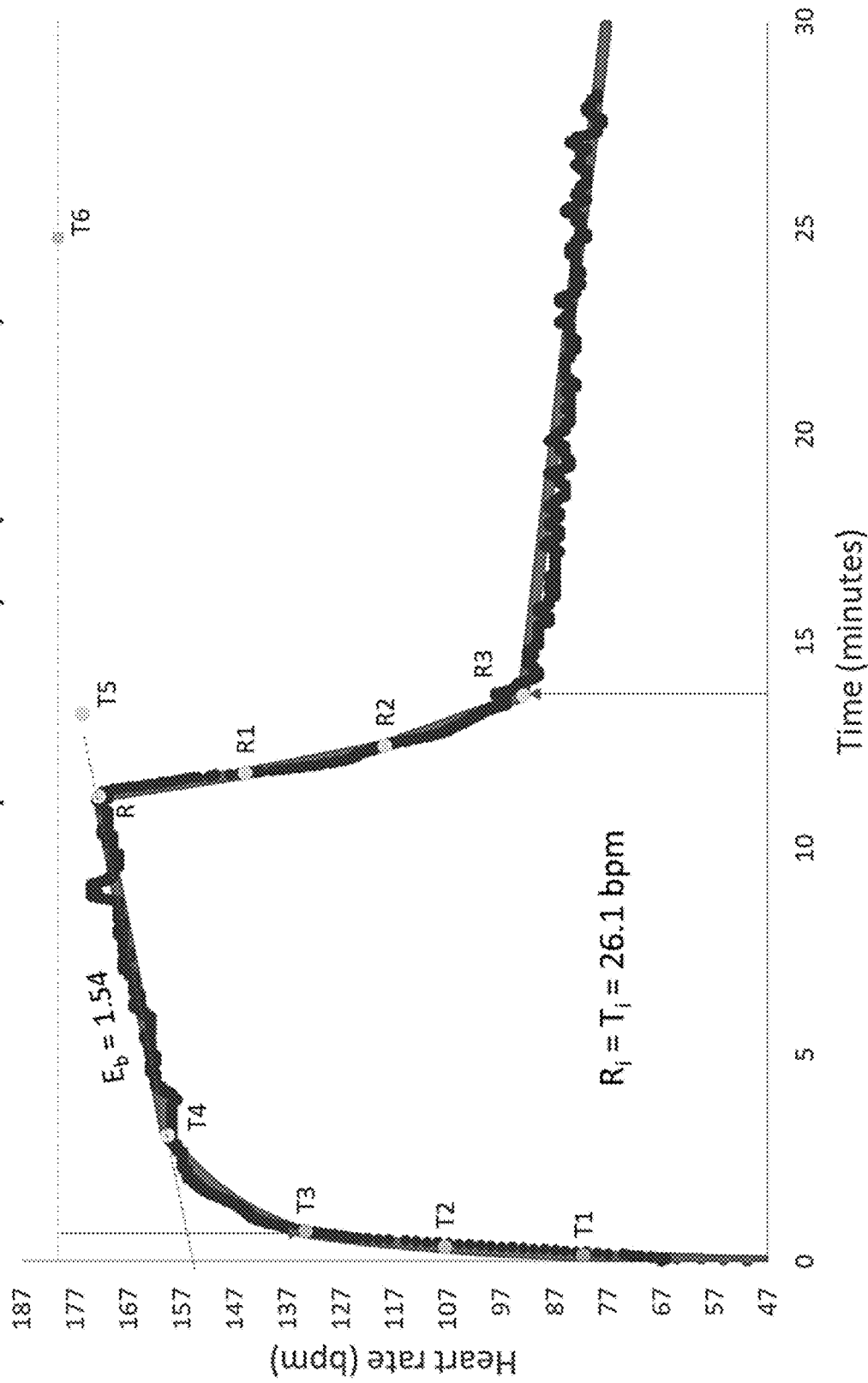

FIG. 31 shows the heart rate model applied to a series of actual heart rate data from a bout of exercise and passive recovery post-exercise. Shaded areas show the oxygen deficit and—repayment divided between the respective energy systems (A-D). Repayment points (r0-r6) are indicated along the y-axis (see text for details).

Figure 32:
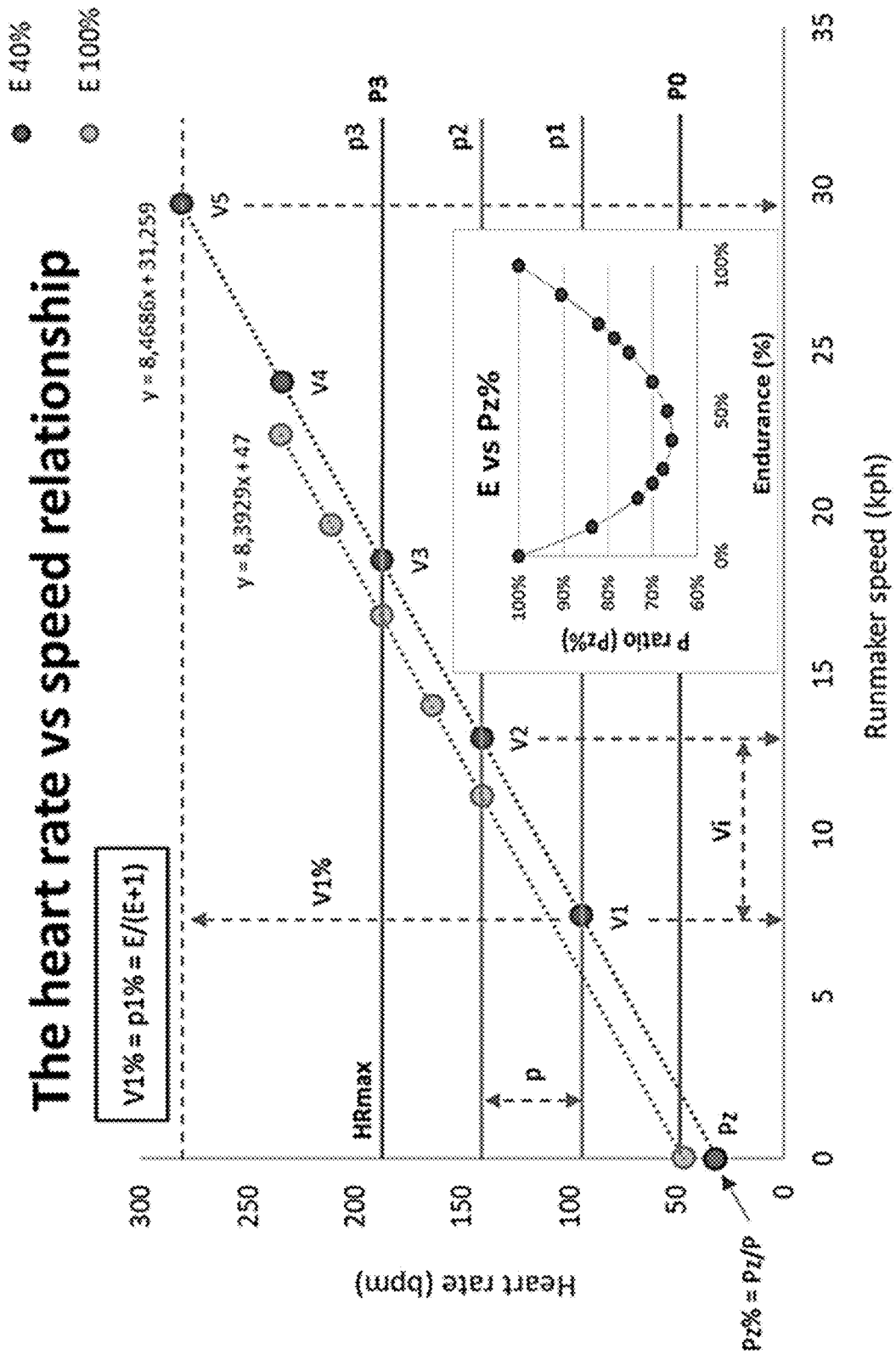

FIG. 32 shows the heart rate vs running speed relationship in the context of the HRK theory. Heart rate thresholds (p1-p3) and speed thresholds (V1-V5) are shown (points) for two runners with widely different endurance levels (E=40% and 100%, respectively). The graph insert shows the polynomial relationship between endurance (E) and the y-axis intercept relative to P (Pz %) (see text for details).

Figure 33:
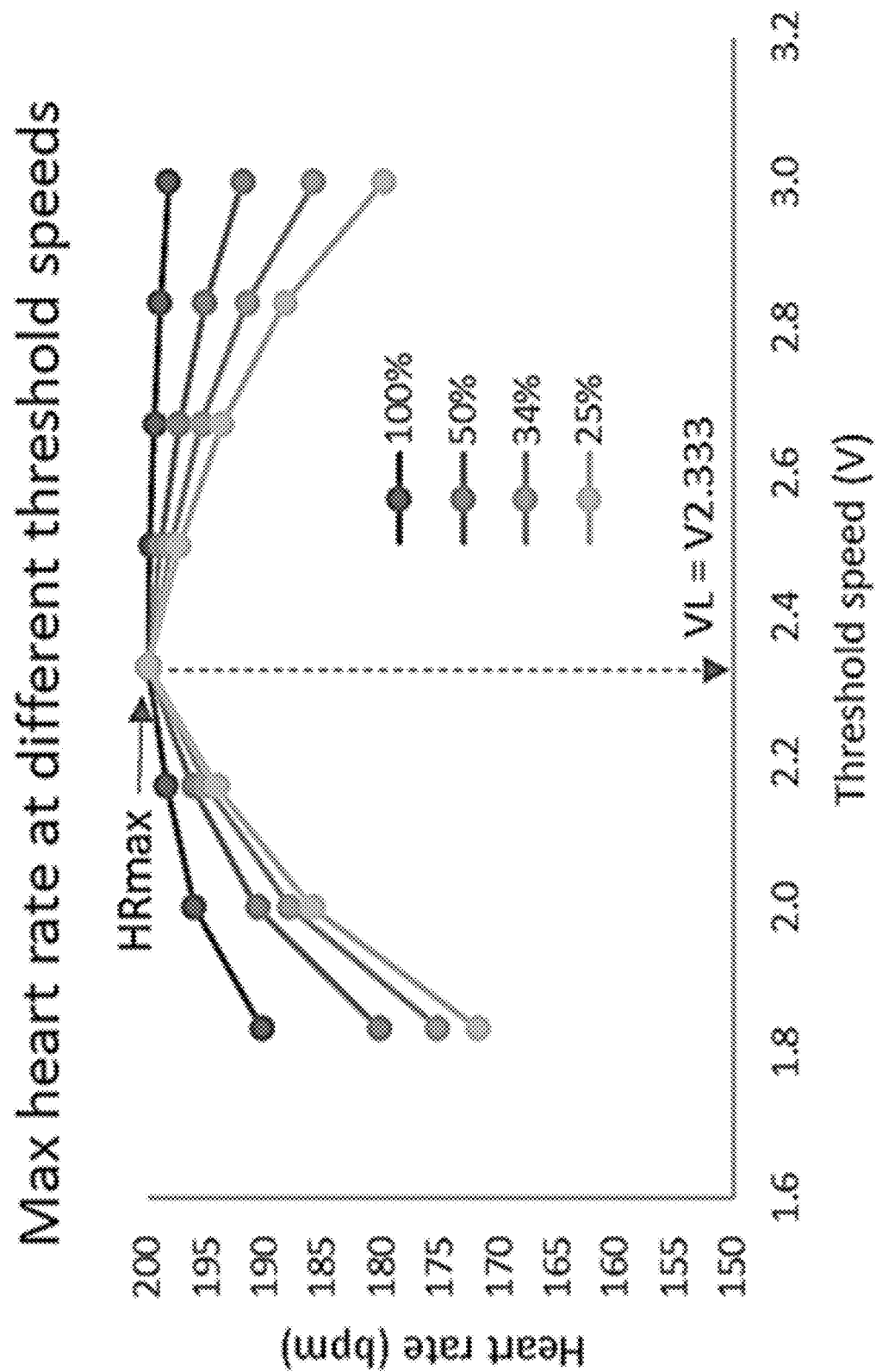

FIG. 33 shows the calculated maximum heart rate at 8 different intensity levels, for 4 runners with different endurance levels and a fixed P of 50 bpm (HRmax=4P=200 bpm). The graph shows that the true HRmax (=188 bpm) is only reached at the VL speed for all the different runners, regardless of the endurance level.

Figure 34:
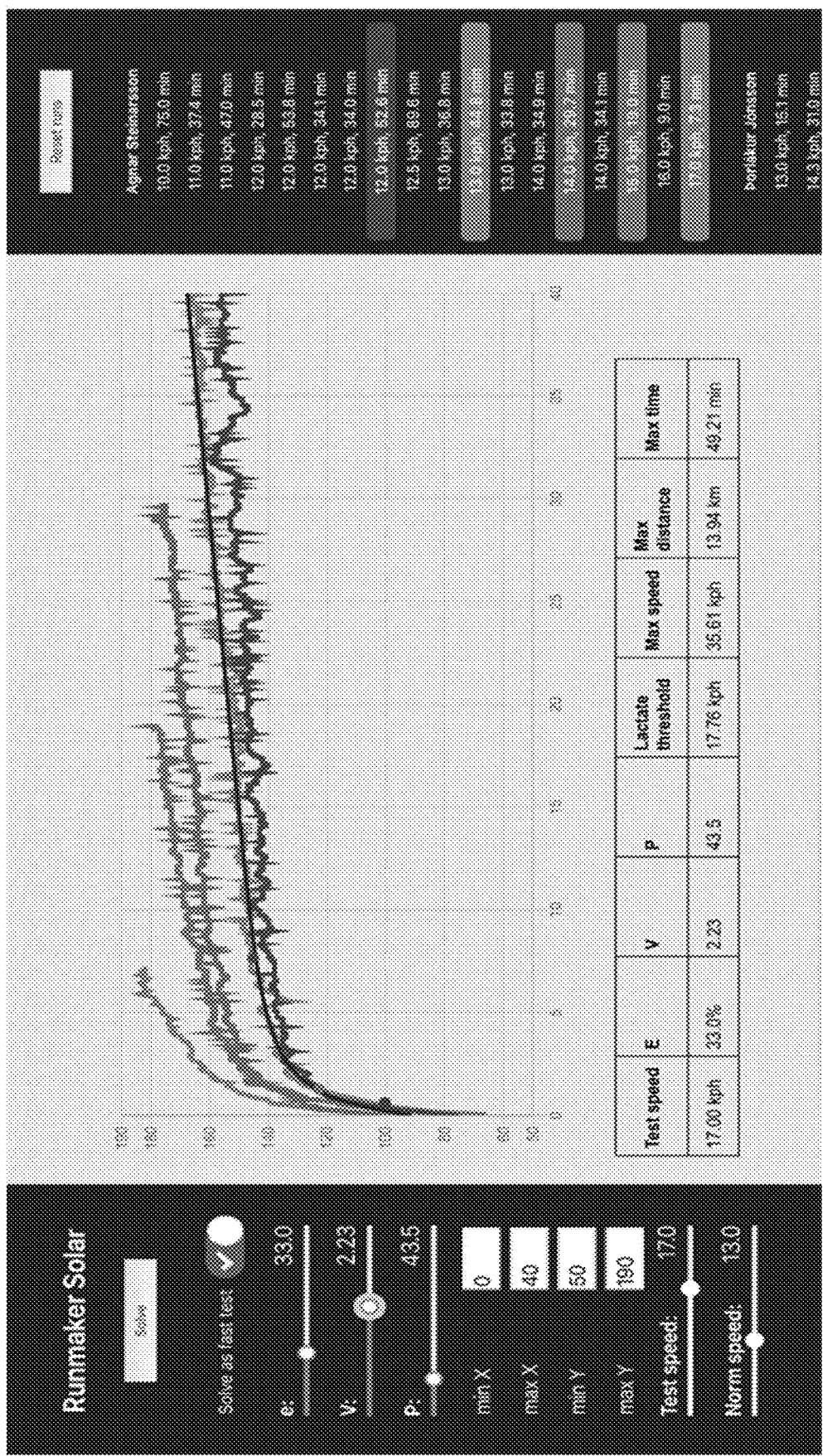

FIG. 34 shows a screenshot from the Runmaker Solar heart rate model.

Figure 35:
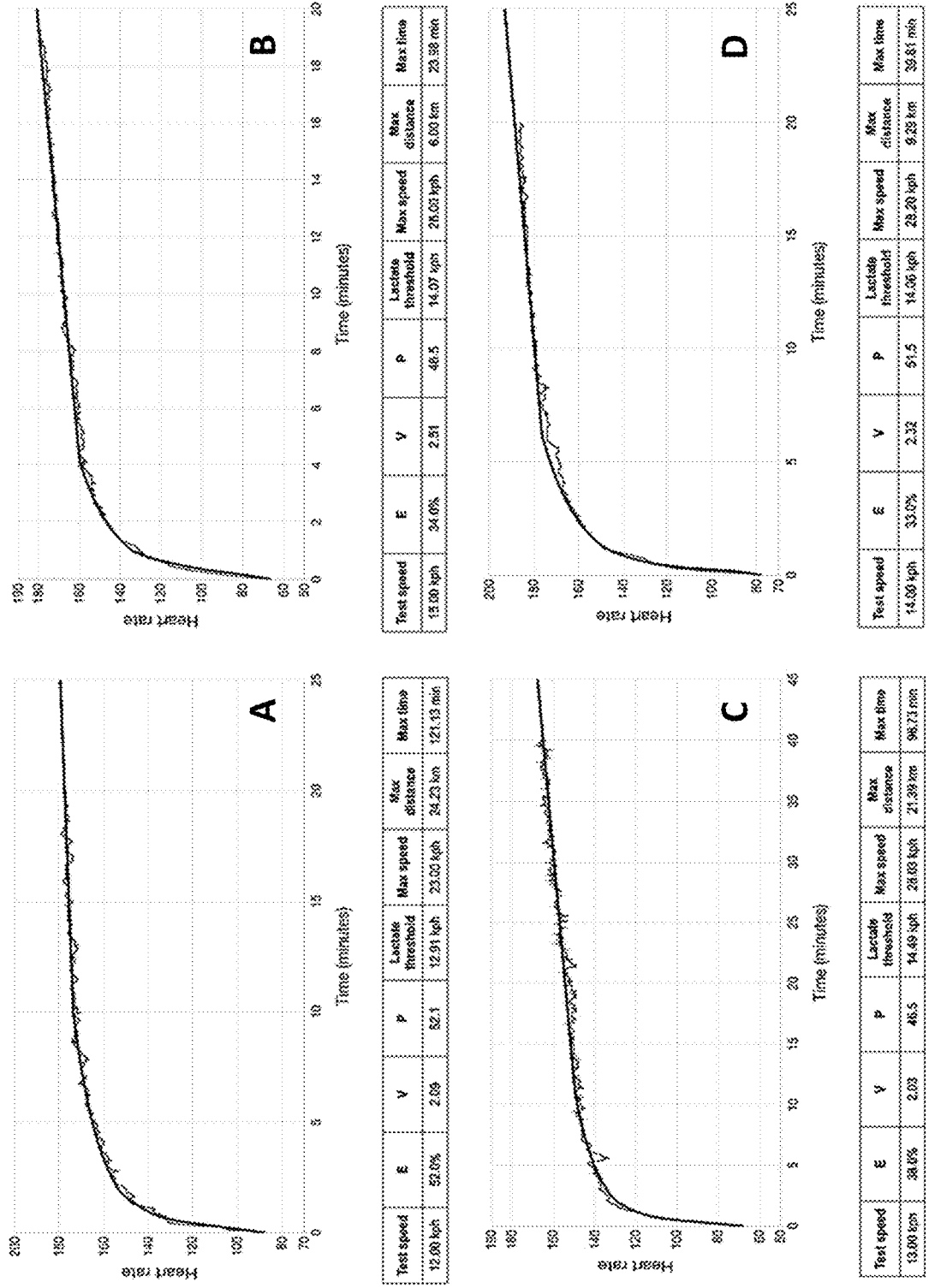
Figure 36:
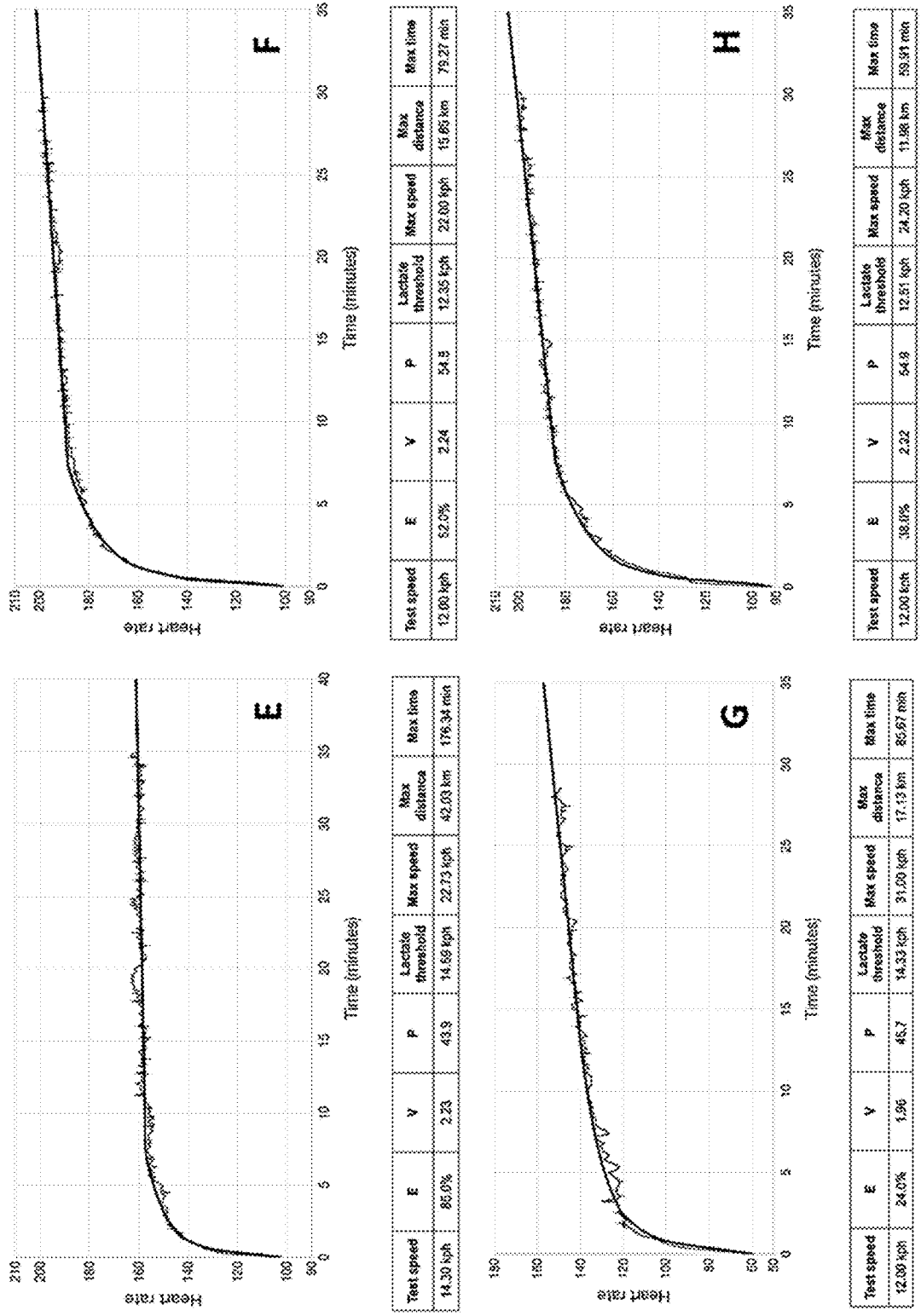

FIG. 35-36 show case examples from four different users, illustrating the analysis by the heart rate model. Every two adjacent graphs (A-B, C-D, E-F, G-H) are produced by the same runner. In each case, the whole line shows the best fit to the data set, with the main results shown underneath each graph.

Figure 37:
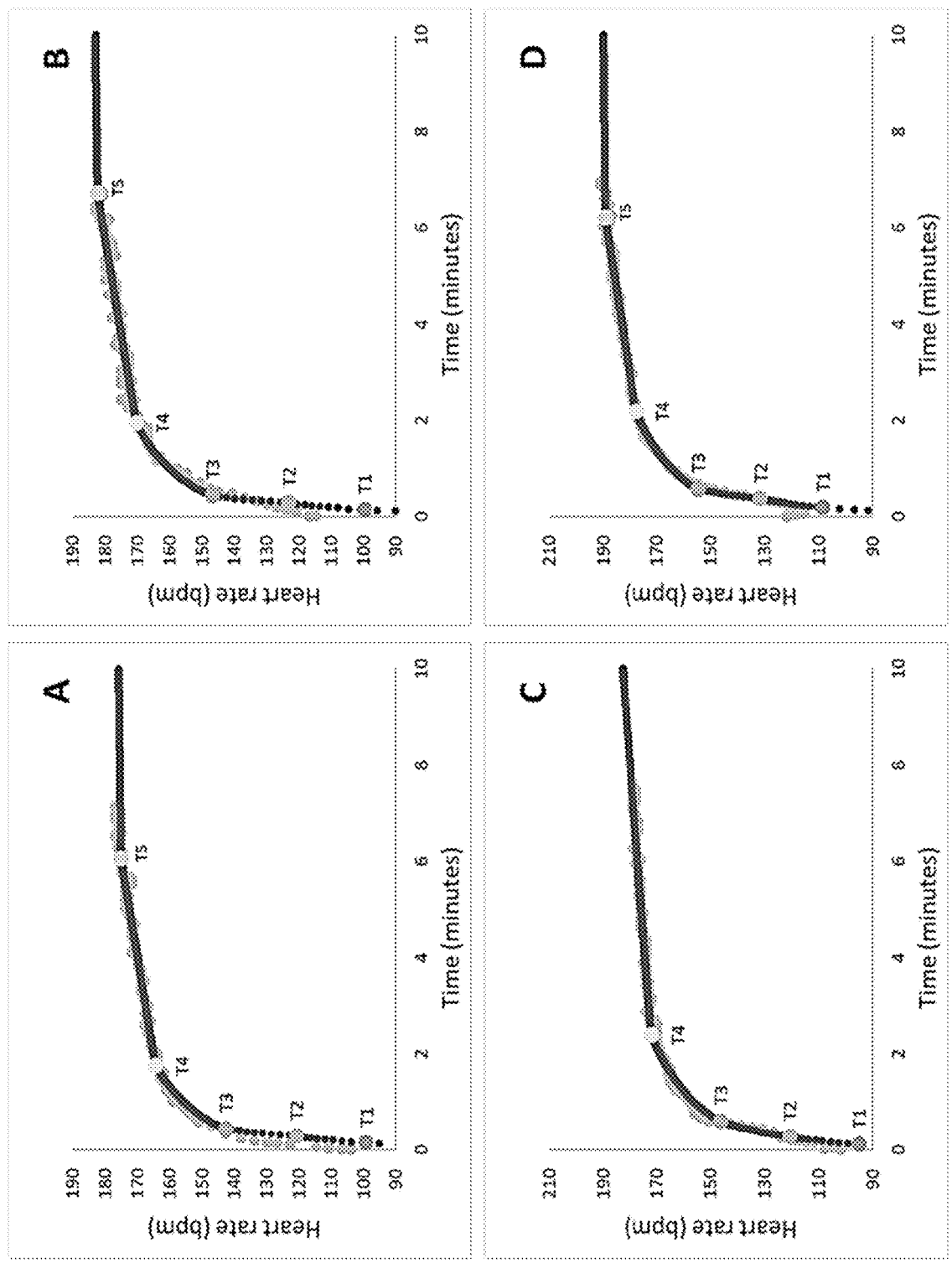

FIG. 37 shows the fitting of heart rate curves produced by four different marathon runners in lactic treadmill running tests (see FIG. 30 for details).

Figure 38:
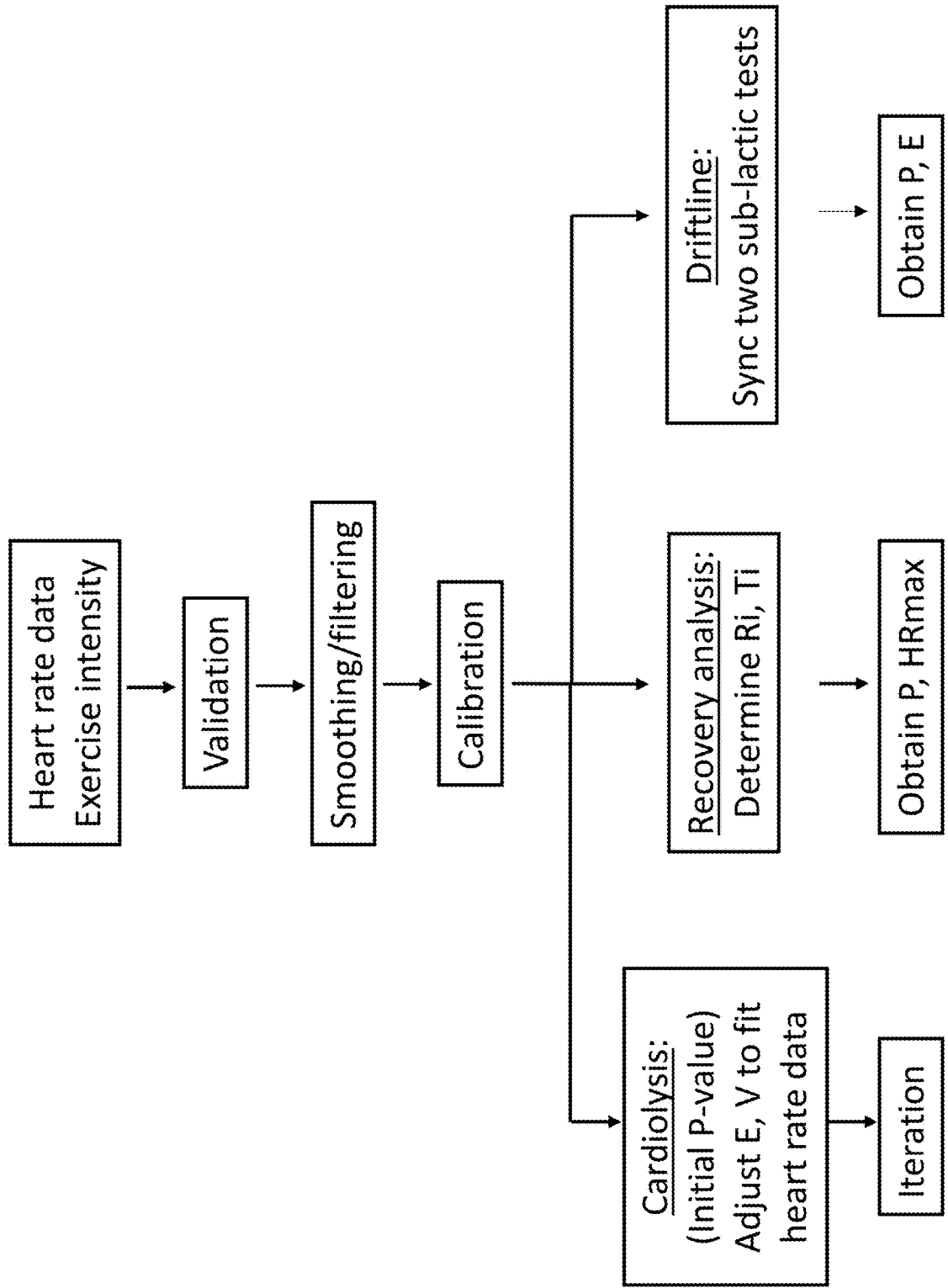

FIG. 38 shows a schematic flow-chart, illustrating the sequential steps carried out in an embodiment of the present invention.

DESCRIPTION OF VARIOUS EMBODIMENTS

The invention is based on a theory developed by the inventors on the cardiorespiratory kinetics of exercise. The invention includes a method of analysis of exercise-induced heart rate to reveal the underlying systematic cardiorespiratory kinetics. Calculated physiological variables include for example aerobic endurance, heart rate thresholds and speed thresholds. In the case of the exercise being running, the method furthermore provides potential running times (i.e. minimal running times) over any given distance. The method merely requires the collection and analysis of heart rate data from a submaximal exercise test, such as from walking, cycling or running and is compatible with a variety of commercially available heart rate monitors.

The invention is based on a unique systematic model of energy and exercise metabolism that effectively structures exercise data in the chaotic field of exercise physiology. For example, in the case of analysis of running, the method syncs five evenly spaced running speed thresholds (energy thresholds) with corresponding heart rate thresholds, creating a perfect match in a coordinate system. The method describes the kinetics of the exercise-induced heart rate curve and detects a system of transition points on the curve, reflecting the successive, but overlapping, recruitment and depletion of energy systems. The method similarly describes the kinetics of post-exercise heart rate recovery curve and detects a system of recovery points on the curve, reflecting the successive restoration of energy systems. The invention provides the first test method to correctly identify all energy thresholds and the first physiologically sound definition of aerobic endurance on a scale of 0-100%, reflecting the alignment of energy thresholds.

The method and system in accordance with the invention can be used in the sports and fitness sector as well as the personal health sector. It can be used to evaluate aerobic- and anaerobic capacity and aid the training of recreational and advanced athletes. It can be used in various endurance related sports, like running, cycling, skiing or swimming, as well as in group sports like soccer, basketball and handball. It can be used for submaximal health and fitness evaluation of non-athletic people in the population, including the elderly. The method can also provide the necessary personalized energy coefficients for direct heart rate-based monitoring of energy consumption and energy expenditure.

The method and system can be implemented on any suitable computational device, such as regular benchtop or laptop computers, on handheld computer devices, smartphones or smartwatches. Recorded data can thus be analysed by a central processing unit (CPU) of the computational device, to generate exercise related parameters as described herein.

The heart rate data can be analysed on the user device, i.e., computer, smartphone, etc. and the resulting exercise parameters displayed to the user on the device. The heart rate data can also, or alternatively, be communicated to a central server that processes the data and returns the results to the user device. For example, when the method is used via a smartphone App, the App can communicate the data to a central server. After processing, the server can return processed data to the App, which displays the results to the user.

A user can perform a cardiovascular exercise, for example, by walking, running, skiing, biking, or training on a cardiovascular training equipment such as treadmill, stationary bike, rowing machine, stair machine (e.g., Stairmaster or the like), elliptical trainer. Heart rate can be measured using a heart rate transmitter and analysed on a CPU-unit that can be, for example, a normal sports watch, a wristop computer, smartphone or similar device as known to the skilled person. Alternatively, it may be possible to use ppg-signal processing so that both the measurement and analysis of data may be done using a wristop device, or the like. Measurement of speed can be done using a GPS signal. The GPS receiver may be embedded, for example, in the watch or wristop device, but an external GPS receiver can also or alternatively be used. During the exercise, data points may be continuously recorded, validated and calculated, with resulting output parameter shown to the user during the exercise, or after exercise, as desired.

The Heart Rate Kinetics Principle

In this application, the principles underlying the invention will be explained in the context of running. In the method according to the present invention, heart rate thresholds and related running speed thresholds of an individual can be determined. The methods are based on the inventor's novel heart rate kinetics theory (HRK theory, presented in this application) about the interrelationship between these thresholds. The HRK theory assumes that three major energy systems do supply locomotive energy for the runner, i.e. the phosphagen system, the glycolytic system and the oxidative system. The theory further divides the phosphagen system and the glycolytic system into two sub-components, for a combined total of five energy systems. In the context of the present invention, these five energy systems will be referred to as A-E systems, as summarized in the list below:

A-system: ATP system (anaerobic).
B-system: PC system (anaerobic).
C-system: Fast glycolytic system (anaerobic).
D-system: Slow glycolytic system (aerobic).
E-system: Oxidative system (aerobic).

Every single movement of the human body is powered by ATP (adenosine triphosphate). ATP is only stored in muscle cells in very small quantities and must be resynthesized very rapidly to sustain muscle contractions. Phosphocreatine (PC) is also stored in muscle cells and is the quickest way to resynthesize ATP. The phosphagen system, consisting of the ATP stores and the PC stores, is the immediate energy source. It powers intense muscle activity but also provides the power needed to bridge the gap during the first minute of medium intense activity, while the slower responding aerobic systems are kicking in. Regardless of the intensity or duration of the activity, the net phosphagen stores used in the early stages are not resynthesized later in the exercise. The system is, however, rapidly replenished during recovery. The A-system represents the ATP stores and the B-system represents the PC stores in the muscle cells.

Glycolysis is the major pathway of glucose metabolism and occurs in the cytosol of all cells. Anaerobic glycolysis is the transformation of glucose to lactate when limited amounts of oxygen are available. This pathway is very fast and powerful and produces ATP about 100 times faster than the oxidative system. On the other hand, it is also very inefficient and only harnesses about 6% of the energy contained in glucose (2 ATP molecules per glucose molecule). This system provides the power for prolonged intense activity but can also provide a significant part of the energy during sustained medium intensity activity. The C-system represents the anaerobic glycolytic system (the fast glycolytic system).

The aerobic energy system utilises fats, carbohydrate and sometimes proteins for re-synthesising ATP. The aerobic system is much more efficient than the anaerobic system, but the pathway involves many complex reactions and is therefore comparatively less powerful and slower to react. The system is traditionally divided into three major steps, i.e. 1) Slow glycolysis, 2) Citric acid cycle and 3) Electron transport chain. These processes produce 2, 2 and 34 ATP, respectively, for a total of 38 ATP from the complete breakdown of 1 molecule of glucose.

The D-system represents the slow glycolytic system and is therefore the first part of the aerobic system. Aerobic glycolysis involves the conversion of glucose to pyruvate, which is then shuttled into the mitochondria for aerobic energy production. Aerobic glycolysis has a slow rate of ATP production and is predominantly utilized during sustained, medium-intensity activity. This system can provide a significant part of the energy during sustained low-intensity activity.

The oxidative system occurs in the mitochondria and consists of the two later stages of the aerobic system, i.e. the Citric acid cycle and the Electron transport chain. In this system hydrogen ions from slow glycolysis and the citric acid cycle are carried to the electron transport chain, where they ultimately produce a total of 34 ATP per molecule of glucose. The E-system represents the oxidative system, providing the vast majority of ATP through oxidative phosphorylation.

All the energy systems always work together to provide ATP for combustion. The systems do not work independently of each other, but rather dominate at different times, depending on the duration and the intensity of the activity (Bowers and Fox. Sports Physiology. McGraw-Hill Higher Education, 2000).

The Heart Rate Curve

The method analyses an individual's heart rate response to exercise. The exercise-induced heart rate response is divided into two major phases, i.e. 1) the active exercise phase and 2) the passive recovery phase. Correspondingly, the heart rate response can be divided into an activity curve and a recovery curve. In this report, the activity curve is explained first and the recovery curve is explained in FIGS. 19 and 20.

Figure 2:
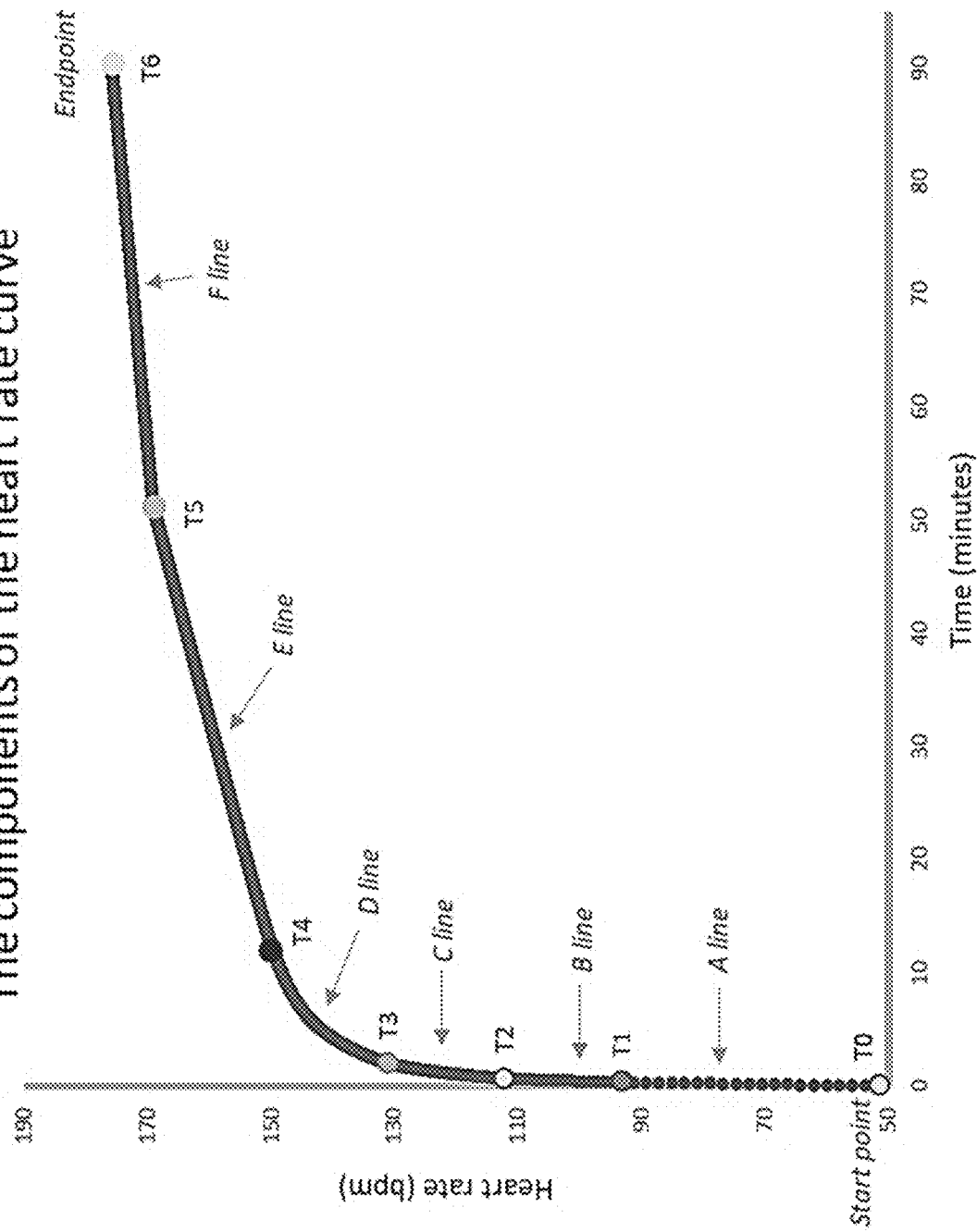
FIG. 2 shows individual components of the heart rate curve according to the invention. The curve starts at the starting point (T0) and ends at the end point (T6). The curve is divided into six segments (A, B, C, D, E and F-lines), separated by five transition points (T1-5). The transition points reflect the sequential recruitment and depletion of energy systems.

The activity heart rate curve is explained in FIG. 2. This figure shows a heart rate curve during a constant-speed treadmill run, at sub-lactic intensity, from a state of rest to voluntary exhaustion at maximum running time. The resulting curve is very steep initially as the heart rate elevates very quickly during the first couple of minutes but then gradually settles and assumes a slow linear elevation after about 15 minutes.

According to the method, the activity curve starts at a starting point (T0) and ends at an endpoint (T6). The curve can be further divided into multiple components, e.g. six different components (A, B, C, D, E and F-lines) separated by five transition points (T1-5). The transition points are both horizontally and vertically aligned, and their coordinates depend on the relative effort of the activity, as well as the endurance of the individual. According to the inventor's HRK theory, the transition points reflect the overlapping activation and/or depletion of energy systems, as explained in later sections.

Figure 3:
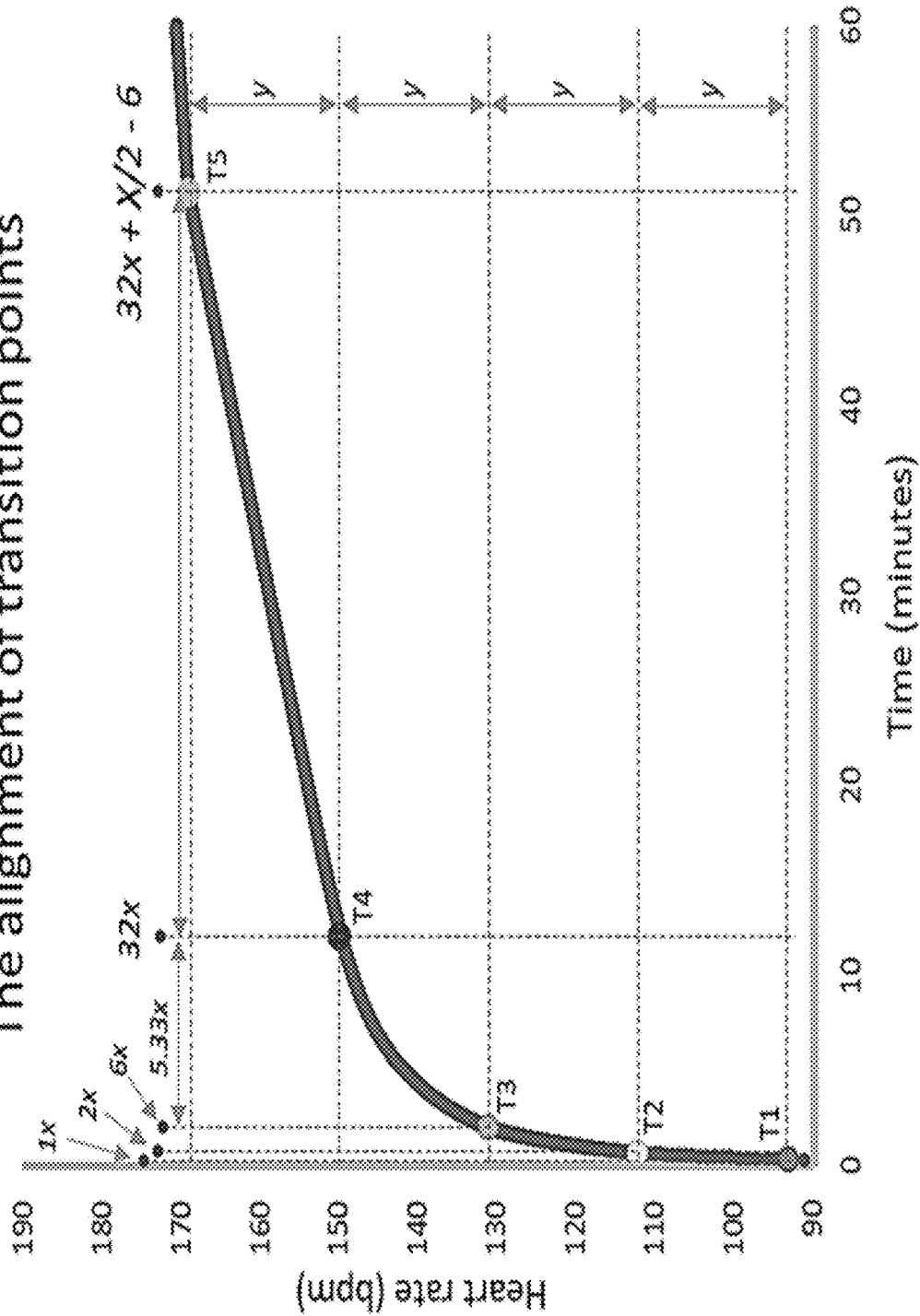
FIG. 3 shows the alignment of the transition points (T1–T5) on the heart rate curve. Dashed lines and arrows show the horizontal and vertical alignment of the transition points. Time-ratios are shown as x and HR-intervals as y.

The shape and elevation of the heart rate curve is determined by the alignment of the curve points. FIG. 3 explains the vertical (heart rate) and horizontal (time) alignment of transition points on the heart rate curve. The vertical alignment of transition points T1–T5 is always even, i.e. with an identical difference in heart rate at each successive transition (marked as y on the graph). The T6 endpoint, on the other hand, is not in an even vertical alignment with the lower points. The vertical alignment reflects the endurance level of the individual, as will be described in a later section.

The horizontal alignment (timing) of transition points, on the other hand, is not even. The T1-T4 points have been found to have a fixed but variable quaternary time alignment, dependent on the threshold speed level (V), irrespective of exercise intensity (e.g., running speed) or endurance of the individual. This means that the timing of T1–T4 can be defined by quaternary ratios, such as 4ths, 8ths, 16ths or 32nds. The exact timing and time ratios depend on the relative intensity of the activity, such as listed in Table 1. In the example in FIG. 3, the time of the T1–T3 points equals $1/32$, $2/32$ and $6/32$ of the T4 time, respectively. The timing of transition point T5, on the other hand, reflects the individual endurance level. With increased endurance, T5 is positioned further away from T4, producing a flatter curve—i.e. the heart rate after T4 increases slower over time for individuals with great endurance, than for individuals with less endurance.

The starting point of the exercise (T0) equals the heart rate at the start of the exercise and is not aligned vertically with (i.e., not in a fixed relationship with) the transition points. The endpoint of the exercise (T6, the point at which exhaustion is reached at the given intensity) is also not aligned with the transition points, neither vertically nor horizontally. For exercises of different intensity, the heart rate curve and the transition points move up and down but the T2 transition point stays fixed in place, unless the intensity is lower than the optimal speed (vOpt) or higher than the super-lactic threshold speed (VSL) of the individual, in which case T2 will descend along with the other transition points (see FIG. 13).

The Energy Systems Behind the Heart Rate Curve

The method assumes that three major energy systems and five different chemical pathways supply the ATP required for sustaining muscle contraction during exercise. The pathways include the ATP-stores (A), the Phosphocreatine pathway (B), fast lactic glycolysis (C), slow aerobic glycolysis (D) and oxidative phosphorylation (E). The method uses the predicted contribution from each energy system to create a heart rate curve, as explained graphically in FIGS. 4 and 5.

The use of transition points on the heart rate curve to predict the overlapping recruitment and contribution from each energy system over a fixed and foreseeable duration, is a novel aspect of the present invention. The HRK theory assumes that the systems are recruited at different times and that the A-D systems become exhausted at different transition point times, i.e. at T3, T4, T5 and T6, for systems A, B, C and D, respectively. During exercise to exhaustion, all the sub-ordinate energy systems (A-D) will thus become depleted sequentially (see FIG. 5).

The A, B and E-systems are assumed to be activated instantly at the initiation of the activity (start of exercise), while the glycolytic C- and D-systems are assumed to be activated at the times of T1 and T2, respectively. The A-system starts immediately at full power and provides the major part of the energy during the first 10-20 seconds, before fading fast and depleting at the time of T3. In the meantime, the E and B-systems are firing up fast to supplement the A-system. The B-system peaks at T2 and then declines gradually until depletion at T4. The C-system starts at T1, peaks at T3 and then declines gradually until complete depletion at T5 (see FIG. 5). The D-system starts at T2, peaks at T4 and then declines gradually until complete depletion at T6 (FIG. 5).

The contributions from the A, B, C and D-systems at any given time are directly additive and the E-system (curves on FIGS. 4 and 5) is assumed to provide the remaining part of the required energy for the activity. At the time of exhaustion, all the sub-ordinate energy systems have been exhausted and all the energy is being provided by the oxidative system. The contribution from the sub-ordinate systems is reflected by the area above the activity curve. At sub-lactic intensity (below the lactate threshold) the momentary heart rate relative to the maximum heart rate for the activity always reflects the relative contribution of the oxidative E-system, peaking as 100% at the time of T6.

The linear increase in heart rate between the T4 and T5 transition points is caused by the additive effects of the declining C- and D-systems during the period. The C-system is depleted at T5 and therefore the linear heart rate increase has a decreased slope between T5 and T6, only reflecting the final decline of the D-system. An increase in intensity (speed) will cause the T6 point to drift closer to the T5 point, until they merge into one point at the lactate threshold speed (VL). This is caused by the progressively faster depletion of the D-system, compared to the depletion of the C-system. At lactic speeds (above VL speed) the D-system will be depleted before the C-system is depleted.

The energy cost of sub-lactic activity is reflected in the maximum heart rate predicted at exhaustion (heart rate T6 at time t6). Based on a maximum heart rate of 200 bpm, the oxidative system thus contributes about 50% of the energy after 1 minute and about 83% of the energy after 12 minutes, in the example in FIGS. 4 and 5. Adding another 9% from the D-system (slow aerobic glycolysis) brings the momentary aerobic contribution up to 92% after 12 minutes.

Speed Thresholds and Heart Rate Thresholds

Running speed thresholds are speed levels at which the runner up-regulates to the next energy system and sports physiology studies have primarily focused on 2-3 thresholds (e.g. lactic threshold). Analysis of these thresholds has historically been generally based on exhaustive laboratory tests and, moreover, the interpretation is poorly defined and inaccurate. The present invention, on the other hand, defines five speed thresholds that are evenly spaced on a personalized grid. The method described herein allows these thresholds to be determined accurately through easy, submaximal tests or leisurely running.

According to the theory underlying the invention (HRK theory), the heart rate curve is positioned in a flexible grid of heart rate thresholds and energy thresholds (speed thresholds), or a so-called cardio-metabolic framework. These thresholds represent shifts between the aerobic- and anaerobic energy systems and are all positioned in an even vertical alignment as shown in FIG. 6, a schematic illustration explaining the cardio-metabolic framework. The heart rate levels in the middle (P0-P3) are fixed and non-flexible on a central axis in quarterly alignment, irrespective of endurance. Endurance (E) is a central concept of the HRK theory, as will be explained in a later section.

The heart rate thresholds (p1-p3) and the speed thresholds (V1-V5), are connected to the main axis through p3 and V3, but the other thresholds move up and down and are directly affected by the endurance. At E=0%, the p1 and V1 thresholds are minimized and aligned with the P0 heart rate level. At E=100%, the p1 and V1 thresholds are maximized and aligned with the P2 heart rate level.

The illustration in FIG. 6 shows that the heart rate levels (P) are fixed in quarterly alignment, irrespective of endurance (E). The maximum heart rate (HRmax) equals the P3 level and the resting heart rate (HRrest) equals the P0 level. However, as explained in Example 8 (FIG. 33), HRmax can only be reached when exercising (e.g., running) to exhaustion at the lactate threshold speed (VL), since slower or faster speeds will only elicit submaximal heart rates. The heart rate thresholds (p) and the speed thresholds (V), on the other hand, are directly influenced by the aerobic endurance (E).

The three heart rate thresholds (p1-3) and the three lowest speed thresholds (V1-3) are perfectly aligned, with the p3 and V3 thresholds always staying aligned with the maximum heart rate level (P3), irrespective of endurance. In the case of zero endurance (E=0%), the p1 and V1 thresholds are minimized and aligned with the P0 heart rate level. At E=100%, threshold compression is maximized, and the p1 and V1 thresholds are maximized and aligned with the P2 heart rate level. All thresholds maintain an even vertical difference at all levels of endurance. The two highest anaerobic speed thresholds (V4 and V5) are in perfect alignment with the lower speed thresholds and can be extrapolated beyond the maximum heart rate threshold.

Threshold Alignment

FIG. 7 shows how the heart rate thresholds (p) and the speed thresholds (V) are vertically aligned with an even vertical difference. The heart rate curve travels through this framework of axes but the transition points do not match the thresholds. The endpoint (T6) equals the maximum heart rate of the individual at this specific constant exercise intensity. The maximum heart rate varies with intensity (speed) and the actual maximal heart rate (HRmax) is only reached after running to exhaustion at the lactic threshold speed (VL), as explained in FIG. 33.

FIG. 8 presents an illustrative example showing speed thresholds and heart rate thresholds for an individual with a max running speed of 30 kph and a HRmax of 200 bpm. The heart rate thresholds are termed p1, p2 and p3 to provide analogy with the speed thresholds. The figurative p4 and p5 heart rate thresholds are extrapolated for reference with corresponding speed thresholds.

The speed thresholds in ascending order are termed V1 (aerobic threshold), V2 (anaerobic threshold), V3 (aerobic max threshold), V4 (anaerobic max threshold) and V5 (max speed threshold). The method defines two additional speed thresholds, namely VL (lactate threshold) which equals V2.333 (see also FIG. 29) and VSL (super-lactic threshold) which equals V3.333. V2 corresponds to the classical definition of the LT1 threshold and VL to the classical definition of LT2, or alternatively OBLA or MLSS (see Introduction). V3 corresponds to vVO2max, or the speed at which VO2max is attained. V4 is assumed to correspond to the speed where the glycolytic systems are maximized. V5 represents the maximum speed, fueled mainly by the powerful phosphagen system (A- and B-systems). The two highest speed thresholds (V4 and V5) and the super-lactic threshold (V3.333) have previously not been recognized as specific thresholds within exercise physiology. The HRK theory assumes a fixed interval ($V_i$) between evenly spaced speed thresholds. The theory assumes a direct relationship between the three lowest speed thresholds (V1-3) and the three highest heart rate thresholds (p1-3).

For any given individual, actual speeds (e.g. running speed, cycling speed, skiing speed, etc.) are normalized to V units for analysis purposes. Threshold speed, a novelty of the present invention, is the key to relating the actual speed to the heart rate curve. Threshold speed is a measure of speed, relative to the individual speed thresholds (in V units). The threshold speed range is different from the actual speed range, since it starts at the aerobic threshold speed (V1) which, for running, is around 6-10 kph for most people (see FIG. 9). The maximum threshold speed (V5), on the other hand, equals the actual maximum running speed.

Aerobic Endurance (E)

According to the inventor's HRK theory, an individual's endurance is reflected in the alignment of the speed thresholds. The five thresholds are evenly spaced but with increasing endurance they lie closer together (see FIG. 9). The three stacked columns in FIG. 9 show three different alignments of speed thresholds, reflecting 0, 25 and 100% endurance, respectively. The figure shows how the speed thresholds are elevated with increasing endurance, reaching an upper limit and maximal compression when V1 equals half of V5. The aerobic endurance is thus reflected in the relative alignment of the V1 and V5 thresholds. The aerobic endurance (E) of an individual can be calculated from the alignment of speed thresholds (V1-V5) through the following equations, where $V_i$ represents the threshold interval and V1% the aerobic threshold percentage (V1%=V1/V5):

$$E = V1/(V5-V1) = V1/(4V_i) = 1/(1-V1\%) - 1$$

These equations produce a value ranging between 0 and 100%, reflecting the aerobic endurance of an individual and provide the first physiologically sound measure of aerobic endurance. In exercise physiology there still exists no specific direct measure of aerobic endurance. Through indirect analysis of race performance, well-trained marathon runners typically possess an aerobic endurance in the range of 80-100% but not even the world's best runners exceed 100% endurance (as calculated from threshold alignment), thereby supporting the HRK theory's definition of endurance. In fact, the only physiological parameter separating the world's best marathon runners is their maximum speed, as they all possess 100% maximized endurance. Middle distance runners typically possess around 40-60% endurance, while elite sprinters typically possess around 5-15% endurance. It is likely that the endurance level reflects the runner's ratio of slow to fast muscle fibres.

The effect of endurance on the heart rate thresholds, like the effect on the speed thresholds, is illustrated in FIG. 10. To explain this effect, it is necessary to distinguish between heart rate levels and heart rate thresholds. The heart rate levels are simply fixed in quarterly alignment with the maximum heart rate (i.e. at ¼, 2/4, ¾ and 4/4 of HRmax), while the alignment of the heart rate thresholds is controlled by the individual endurance level. Both these systems are, however, directly connected and the heart rate levels provide the framework for the heart rate thresholds. FIG. 10 shows that p3 always equals P3 (same as HRmax) but the p1 threshold can range between P0 (2/4 of HRmax) and P2 (¾ of HRmax), depending on the endurance of the individual. The p2 threshold always lies midway between the p1 and p3 thresholds. The thresholds are separated by the threshold interval (p). The heart rate thresholds therefore become gradually more compressed and elevated with increased endurance.

Since speed thresholds and heart rate thresholds are aligned, the following equation holds true for the aerobic HR-threshold (p1): p1%=V1%=E/(E+1), where p1 is expressed relative to HRmax (=P3). This means that if V1 equals 25% of V5, then p1 also equals 25% of HRmax. The following equations can thus be used to calculate the aerobic heart rate threshold (p1):

$$p1 = P + p1\% \cdot (4P) = P + p1\% \cdot (HRmax)$$

where P is the heart rate level interval, HRmax is the maximum heart rate and p1% is p1 divided by HRmax (P3). The other heart rate thresholds (p0 and p2) can then be calculated by way of extrapolation, once the p1 and p3 thresholds have been identified.

The Base of Endurance

The linear tracing of transition points on the heart rate curve represents another novel feature of the invention. Having first identified the individual cardiometabolic framework, the heart rate curve can be traced by drawing lines between any two consecutive transition points and forecasting backwards into negative time, as explained in FIG. 11.

The graph in FIG. 11 shows how the base of all the energy systems can be identified through the linear tracing of the exercise-induced heart rate curve. The A, B, C and D systems are all based from the P0 heart rate level (=P), which equals 47 bpm in the example shown in FIG. 11. The tracing lines forecasted from the transition points, intersect at their respective base positions (on the heart rate thresholds) as $X_A$, $X_B$, $X_C$ and $X_D$, respectively, as shown in FIG. 11. The intercepts $X_B$, $X_C$ and $X_D$ are obtained by extrapolating lines through transition points T1 and T2, T2 and T3, T3 and T4, respectively. The E and F systems, on the other hand, are based from the p1 and p2 thresholds and intersect at their respective base positions (i.e., at heart rate=p1 and heart rate=p2, respectively) as $X_E$ and $X_F$. The E and F lines share the same horizontal base position (i.e., position on time axis in negative time) and are collectively referred to as X. According to the HRK theory, the C-system (fast glycolysis) is activated at the p1 threshold and the D-system (slow glycolysis) at the p2 threshold. The base position of these two systems reflects the base of aerobic endurance.

The base of aerobic endurance (X) can be identified directly from the heart rate curve in the grid of heart rate thresholds, as shown in FIG. 11. The figure shows how the base of aerobic endurance can be traced directly from the heart rate curve, if the transition points and heart rate thresholds have been recognized. If a line (the E-line) is drawn through transition points T4 and T5 and then forecast backwards until it crosses the aerobic threshold (p1), the intersect ($X_E$=X) represents the base of aerobic endurance. Through experimentation this intersect has a range of 36-360 minutes in negative time, reflecting the range of 0-100% endurance. The HRK theory defines the endurance base (e) as e=X/36, ranging between 1-10. The aerobic endurance (E) can be calculated from the endurance base with the following equation:

$$E = \log(e) \text{ or alternatively } e = 10^E$$

Similarly, the F-line can be drawn through transition points T5 and T6 and then forecast backwards until it crosses the anaerobic threshold (p2). This intersect ($X_F$) represents the base of the F-system and equals the base position of the E-system.

Since the timing of T4 is fixed but the endpoint (T6) depends on endurance, the ratio between T4 and T6 (t6/t4) reflects the aerobic capacity. At sub-lactic intensities, this ratio equals the individual X-factor (Xf=X/12) and thus can potentially range between 3 and 30, for the extreme values of X. Therefore, a runner with 100% endurance (X=360 minutes) running at lactate threshold speed (t4=6 minutes), could potentially run for 180 minutes at this speed (t6=t4

Xf=6 min 30=180 min). A person with 40% endurance (X=90 min) could potentially run for 45 minutes at the same relative speed (t6=6 min 7.5=45 minutes).

According to the method, the timing of T5 is not universally fixed but dependent on the individual endurance level. In general, the individual with greater endurance has a much flatter curve and can exercise longer before exhaustion ensues. A person with 100% endurance will have a t5 of 180 minutes at the lactate threshold intensity (e.g., running speed), while an individual with 0% endurance will have a t5 of only 18 minutes. As can be seen from FIG. 13, the timing of T5 is fixed as t5=X/2 at running speeds below the lactate threshold (see FIG. 11 and FIG. 13).

FIG. 12 shows the heart rate curves generated at the same exercise intensity by five individuals with different endurance levels but sharing the same HRmax and maximum speed. The graph shows that the endurance level has a profound effect on the shape of the heart rate curve, with the curve getting sharper and ultimately flatter as the endurance level gets greater. This agrees with the commonly observed fast cardio-dynamic phase of endurance athletes.

The Kinetics of the Heart Rate Curve

The heart rate curve can only be simulated correctly if the coordinates (heart rate and time) are known for all the curve points (T0–T6) at all possible intensity (speed) levels. As explained previously, the coordinates of T0–T4 have a fixed relationship with the threshold speed and are thus easy to simulate. The coordinates of T5 and T6, on the other hand, depend directly on endurance and their coordinates are decided by the interplay between the E- and F-lines of the heart rate curve. The HRK theory behind the present invention offers a complete understanding of the heart rate kinetics, as shown in FIG. 13.

The speed-related kinetics of the heart rate curve are summarized visually in FIG. 13, which shows the linear tracing of heart rate curves for 13 different threshold speed levels, from the start of the exercise to predicted voluntary exhaustion (Runtime). The lowest threshold speed level is the aerobic threshold speed (V1), while the highest level is the super-lactic threshold speed (VSL=V3.333). The graph illustrates the speed-related response of the heart rate curve, with the associated drift of transition points and aerobic base, within the cardio-metabolic framework.

The key to the kinetics of the heart rate curve lies in understanding the nature of the two linear components of the heart rate curve, the E- and F-lines (see FIG. 2). As explained in FIG. 11, the lines can be traced back to their respective bases at the p1 and p2 heart rate thresholds. The complete picture is, however, much more complicated as it includes both base drift and complex interplay between the two lines. According to the HRK theory, the E- and F-lines are connected in such a way that their trace line intercepts with the HR(y)-axis ($E_a$ and $F_a$, see dashed lines in FIG. 13) are always exactly ⅓ threshold speed intervals (=p/3) apart on the y-axis. The F-line begins to rise once the E-line crosses p1.667 and is maximized at p2.667 when the E-line peaks at p2.333.

Referring to FIG. 13, at the aerobic speed (V1), the heart rate curve and all the transition points are parallel to the p1 axis. At higher speeds, the curve and all the transition points get elevated, until the optimal speed (Vopt=V1.667) is reached, where the F-line is parallel to the time axis and T2 reaches its peak height. This speed is designated as being optimal, since the possible non-stop running distance can theoretically be maximized at this speed. At higher speeds, T2 is fixed (in height), while the F-line goes from flat to a positive incline.

At the VL speed (VL=V2.333=lactate threshold speed), T3 and T4 reach their peak height, while T5 hits its peak at the p3 heart rate threshold (p3=HRmax) and the F-line disappears. At lactic speeds (>VL) T1–T4 remain peaked, while T5 starts declining and the F-line re-appears. The E-line now has an elevated slope and points towards a supra-maximal heart rate (PS), depending on the threshold speed (explained in Example 5 and FIG. 30). The F-line always ends in T6 at the same time as the extended E-line crosses the p3 threshold and determines the Runtime (maximum exercise time) for that specific speed level. T6 is the highest heart rate at each specific threshold speed level but only equals HRmax when running at the VL speed. At higher or lower speeds, T6 only equals HRsubmax, as shown in FIG. 13 and FIG. 33.

At lactic speeds (>VL) the aerobic base time (X) starts drifting towards the Y-axis (X-drift). This causes the opposite left drift of all the transition points and reduces the Runtime to exhaustion (time at the p3 intercept) at an accelerated pace, compared to sub-lactic speeds (<VL). The transition points T1–T5 are evenly spaced at sub-lactic speeds, but at lactic speeds T5 is replaced by T6, since T5 starts to decline. The transition point interval (T0 increases with increased speed until it peaks and remains fixed at lactic speeds equal to or higher than VL.

Referring to FIG. 11, at lactic speeds (>VL) the C and D lines begin to drift relatively closer to the A and B lines, causing the heart rate curve to become gradually steeper during the initial phase up to T4. At the super-lactic threshold speed (V3.333) the A-D lines have all overlapped with a base position close to zero, resulting in a very steep and straight curve up to the T4 point. At super-lactic speed, above V3.333, the t1–t4 points remain fixed and minimized, as shown in Table 1.

The bases of the E- and F-lines are unaffected at sub-lactic intensities but at lactic intensities (>VL) they start drifting closer to the y-axis, until they are minimized at the maximum speed. This causes the relative aerobic energy contribution to decay exponentially with increasing intensity and approach zero at the maximum speed. The marvelous kinetics of the heart rate curve are further explained in the next section.

A feature of the invention is the fixed and known timing of transition points with respect to the threshold speed level (V). The timing of T1–T4 decays exponentially with increasing speed but the timing of T5 is fixed as t5=X/2 at speeds between Vopt and VL. At super-lactic speeds (>VL) t5 is reduced and T5 starts to decline as the F-line cuts off the E-line sooner and sooner. The height (heart rate) of the point is maximized at the VL speed but begins to decline again at the V3.333 super-lactic threshold.

The Timing and Ratios of Transition Points

As explained previously, the timing of the first four transition points is not affected by endurance or max speed, and thus universal with respect to exercise intensity (threshold speed). This means that all healthy individuals share the same universal time pattern for these four initial transition points (T1–T4). The remaining transition point (T5) and the endpoint (T6), on the other hand, are not universal, since they are directly affected by the endurance. The alignment of the transition points changes with increased threshold speed, as shown in Table 1.

TABLE 1

The relationship between threshold speed (V) and transition point times (t1-6) on the heart rate curve, according to the HRK theory (t5 is excluded). The table also shows the time ratios and the time multiples between indicated points. The values given for t1-t4 are universal but the values given for t6 are based on an endurance (E) of 34% (see text for details).

| | T point times (minutes) | | | | | t ratios | | | | t multiples | | | |
|---|---|---|---|---|---|---|---|---|---|---|---|---|---|
| v | t1 | t2 | t3 | t4 | t6 | t1 | t2 | t3 | t4 | t2/t1 | t3/t2 | t4/t3 | t6/t4 |
| 1.667 | 0.75 | 1.5 | 4.5 | 24 | 156 | 1 | 2 | 6 | 32 | 2 | 3 | 5.333 | 6.50 |
| 2 | 0.375 | 0.75 | 2.25 | 12 | 78 | 1 | 2 | 6 | 32 | 2 | 3 | 5.333 | 6.50 |
| 2.333 | 0.1875 | 0.375 | 1.125 | 6 | 39 | 1 | 2 | 6 | 32 | 2 | 3 | 5.333 | 6.50 |
| 2.667 | 0.1875 | 0.375 | 0.9375 | 3 | 15.4 | 1 | 2 | 5 | 16 | 2 | 2.5 | 3.2 | 5.14 |
| 3 | 0.1875 | 0.375 | 0.75 | 1.5 | 6.11 | 1 | 2 | 4 | 8 | 2 | 2 | 2.0 | 4.07 |
| 3.333 | 0.1875 | 0.375 | 0.5625 | 0.75 | 2.42 | 1 | 2 | 3 | 4 | 2 | 1.5 | 1.333 | 3.22 |
| 3.667 | 0.1875 | 0.375 | 0.5625 | 0.75 | 1.91 | 1 | 2 | 3 | 4 | 2 | 1.5 | 1.333 | 2.55 |
| 4 | 0.1875 | 0.375 | 0.5625 | 0.75 | 1.51 | 1 | 2 | 3 | 4 | 2 | 1.5 | 1.333 | 2.02 |
| 4.333 | 0.1875 | 0.375 | 0.5625 | 0.75 | 0.90 | 1 | 2 | 3 | 4 | 2 | 1.5 | 1.333 | 1.60 |
| 4.667 | 0.1875 | 0.375 | 0.5625 | 0.75 | 0.47 | 1 | 2 | 3 | 4 | 2 | 1.5 | 1.333 | 1.26 |
| 5 | 0.1875 | 0.375 | 0.5625 | 0.75 | 0.19 | 1 | 2 | 3 | 4 | 2 | 1.5 | 1.333 | 1.00 |

Table 1 shows T point times (t1-6, t5 excluded), ratios and multiples for threshold speed levels ranging from V1.667 to V5 (maximum speed). The values for t6 are based on an endurance (E) of 34%. The t6 time equals the maximum time at that specific threshold speed (Runtime). The table shows that although the T point times have different relationships with the threshold speed (V), they all decay exponentially over a range of speeds. t1 and t2 decay exponentially up to a fixed minimum at V2.333 (lactate threshold). t3 also decays exponentially up to V2.333, preceding a linear decrease up to a fixed minimum at V3.333 (super-lactic threshold). t4, on the other hand, decays exponentially at all speeds, up to a fixed minimum at V3.333 (super-lactic threshold). t6 decays exponentially in four separate phases, i.e. <V2.333, V2.333–V3.333, V3.333–V4 and V4–V5. During the first phase of decline, the T point times decay according to an exponential function of the form f(x)=abx. The equations are shown below, where V stands for threshold speed and y equals 24:

$$t1 = 24 \cdot 8^{-V} = 1y \cdot 8^{-V} \quad (<V2.333)$$

$$t2 = 48 \cdot 8^{-V} = 2y \cdot 8^{-V} \quad (<V2.333)$$

$$t3 = 144 \cdot 8^{-V} = 6y \cdot 8^{-V} \quad (<V2.333)$$

$$t4 = 768 \cdot 8^{-V} = 32y \cdot 8^{-V} \quad (<V3.333)$$

$$t6 = 4992 \cdot 8^{-V} = 208y \cdot 8^{-V} \quad (<V2.333)$$

The ratios (multiples) between the consecutive constants are 2, 3, 5.333 and 6.50, and the product of the first three constants is 32, such as shown in Table 1. The t6/t4 ratio (=6.50) equals the X-factor in this example. An endurance (E) of 34% gives an X of 78 minutes and thus an X factor (Xf=X/12) of 6.50.

The table shows how the t ratios change with increasing threshold speed, as the transition points drift closer together. T1–T4 have a fixed ratio of 1:2:6:32 up to the lactate threshold speed (VL=V2.333). At higher, lactic speeds, the points start drifting and the ratio changes until a stable 1:2:3:4 ratio is reached at the super-lactic threshold speed (VSL=V3.333). Beyond the VSL threshold there are no further changes in the t ratios.

It is interesting to look at the minimum times of the transition points, as well as the calculation of the Runtime (t6). The t1 minimum equals 0.1875 minutes or 11.25 seconds and the t2, t3 and t4 minimums, equal 22.5, 33.75 and 45 seconds, respectively. The HRK theory assumes that the highest threshold speeds eliciting T4, T3, T2 and T1, are V4, V4.333, V4.667 and V5, respectively. The Runtime to exhaustion (t6) at speeds below the V4 threshold speed, is calculated by multiplying t4 with the time factor (time factor=tf, see equation below). The time factor equals the X-factor at lactic speeds (>VL) but starts to decay exponentially and approaches unity at the maximum speed (V5). At speeds above V4, Runtime is calculated by multiplying the next subordinate t time with the time factor. In the example shown in Table 1, the Runtime equals 39 minutes at the VL threshold, 2.42 minutes at the VSL threshold and 11.25 sec at the maximum speed.

The Time-Distance Relationship

Based on the theory behind the present invention, it is now for the first time possible to formulate the time-distance relationship over all distances, with one universal mathematical equation. The key to the solution is the discovery of the heart rate curve components and the underlying kinetics of the energy systems. Due to the sequential recruitment and depletion of the five energy systems, the power-duration relationship is divided into five sequential phases as shown in FIG. 14.

FIG. 14 illustrates the relationship between running speed and maximum distance for that speed. The relationship can be divided into five separate phases, i.e. 1) sub-optimal, 2) sub-lactic, 3) lactic, 4) super-lactic and 5) sprinting phases, separated at key thresholds as indicated on the graph. During the sub-optimal phase (nr. 1) the distance is predicted to decrease again at lower speeds (not shown). During each of the next three phases (phases 3-4) the relationship is linear. During the fastest phase (nr. 5) the relationship is polynomial, reflecting the recruitment and depletion of all the energy systems at once. The threshold distances can be read from the graph, from a minimum of approximately 100 m at the maximum speed (Vmax) up to a maximum (Dmax) of approximately 100 km at the optimal speed (Vopt).

According to the HRK theory, the maximum running time at all possible running speeds can be predicted from the kinetics of the heart rate curve. The graph in FIG. 27 illustrates how the E-line of the heart rate curve ultimately dictates the potential maximum running time to voluntary exhaustion (Runtime). Having first identified the heart rate thresholds (p1–p3), and the aerobic endurance base (X), the Runtime can be predicted from the E-line intercept with the HRmax threshold (p3). The time at the endpoint of the heart rate curve (T6) is always equal to the time at the p3 intercept (HRmax).

The Runtime at all intensities (speed), except sprinting intensity, can be calculated as a direct product of the T4 transition time (t4). At sprinting intensities, the Runtime is the product of the highest sub-ordinate transition time (t1, t2 or t3), as shown in Table 1. Runtime is calculated with the following equation:

$$\text{Runtime} = \text{Time factor} \cdot T\text{-time} = tf \cdot tT$$

where tf is the unitless time-factor (see equation below) and tT is the transition point time (T-time). The calculation of transition times is explained in the previous section. The time-factor (tf) is fixed as Xf=X/12 at sub-lactic speeds (<VL) but decreases exponentially above VL and approaches unity at the maximum speed (V5), as shown in Table 1. At lactic speeds or higher, the time-factor can be calculated with the following equation:

$$tf = X/12 \cdot e^{(0.9318 - 0.375 \cdot Ln(X)) \cdot (V - 7/3)}$$

where X is the endurance base time and V the threshold speed. A runner with 100% endurance (E) or X=360 minutes, has an X-factor (=time factor above VL) of 30 (Xf=X/12). The calculated Runtime at the VL speed is 180 minutes (=3 hours). If the runner has a VL speed of 14 kph, he or she should be able to run a marathon in three hours. However, when running at the V3 threshold speed of 15.8 kph, the time factor is reduced to 12.82 and t4 reduced to 1.5 minutes, which gives a Runtime of 19:23 minutes for a 5 km race.

Due to the complex power-duration relationship (see FIG. 14), the time-distance relationship cannot be described with one general equation over all distances but must be divided into four separate phases. The reason for this division is the overlapping and sequential depletion of energy systems, as previously described. FIG. 15 shows the time-distance relationship during each phase, as defined in FIG. 14. Please note that the lines and equations on the four graphs only apply to one specific set of input variables and vary with changes in max speed and endurance. FIG. 15 shows that the time-distance relationship is polynomial during the sprinting phase but exponential in the other distance phases. Knowing the time-distance relationship, over all distances it is now possible to make a realistic race time predictor that accommodates all levels of maximum speed and endurance (see Example 2).

The Controlling Forces on the Heart Rate Curve

It should be apparent from the foregoing description that after adjusting for individual differences in endurance and maximum heart rate, all healthy humans share a universal heart rate response to exercise of constant intensity. The shape and height of the heart rate curve is controlled by the three key cardiometabolic parameters, E (endurance), P (heart rate level) and V (threshold intensity (e.g. speed)). To explain how these parameters control the heart rate curve it is useful to start with a normalized heart rate curve, based on medium values of E (50%), P (50) and V (2.0), as shown in FIG. 16.

In this figure it is illustrated how the heart rate curve is controlled by the three parameters E, V and P. The first graph shows a normalized curve (E 50%, P 50 bpm, V 2.0) and the controlling forces of the key parameters are indicated by arrows. E is the horizontal parameter and either stretches or compresses the curve horizontally. P is the vertical parameter and either elevates or lowers the curve vertically. V is the diagonal parameter and shifts the curve diagonally.

After normalization, all healthy individuals (men and women of all ages) share the same exact response to exercise. The adjustment of the heart rate curve for different individuals and different intensities can be split into three separate steps. The first step (second graph) involves vertical P-adjustment, in the example shown, this is done by lowering P down to 45 bpm and therefore HRmax down to 180 bpm (=4P). The second step (third graph) involves diagonal V-adjustment, in this case increasing V up to 2.3 threshold speed units or just under lactate threshold speed (V2.333). The third step (fourth graph) involves horizontal E-adjustment, in this case increasing E up to 100% endurance. The final curve is an example showing a curve that might typically be produced by a long-distance runner during a marathon race. Together these three parameters thus adjust the shape of the curve and place it correctly inside the cardiometabolic framework.

The Collapse and Compression of the Heart Rate Framework

The individual cardio-metabolic framework is fixed and stable at speeds above the optimal speed (Vopt). However, at speeds below Vopt, the heart rate framework begins to collapse and is fully collapsed at the aerobic speed threshold (V1), as shown in FIG. 17. At this low level of intensity, all the transition points are equal in heart rate, which equals p1.

Due to the collapse, the F-line of the heart rate curve will be flat towards exhaustion at all sub-optimal running speeds. Without the collapse, the transition points could not possibly be aligned at the V1 threshold. The optimal speed level (Vopt) is not affected by endurance but is rather fixed at the threshold speed V1.667. By way of example, for an elite marathon runner this might be a speed of about 16 kph, producing a flat long-term heart rate response.

As explained in the above, the individual cardio-metabolic framework is fixed and stable at speeds above the optimal speed (Vopt). However, the framework is highly dependent on endurance and can therefore differ widely between individuals with different endurance levels. This is illustrated schematically in FIG. 18, where heart rate curves for five different endurance levels are shown. The five graphs in FIG. 18 show the effect of endurance on the cardio-metabolic framework. The same effect is shown in FIG. 12 with five superimposed heart rate curves. The graphs in FIG. 18 show illustrative heart rate curves for five different individuals, sharing the same HRmax but differing in endurance levels. The five graphs show how the absolute value of the aerobic base (X) increases from 36 minutes at 0% endurance to 360 minutes at 100% endurance, and the resulting increase in Runtime to exhaustion at T6. Meanwhile, the heart rate thresholds get more and more compressed as the curve gets sharper with increased endurance.

The Heart Rate Recovery Curve

The exercise-induced heart rate response is divided into two major phases, i.e. 1) the active exercise phase and 2) the passive recovery phase. Following exertion, a recovery process begins to replenish supplies of PC, ATP, glycogen, glucose and myoglobin (protein that stores oxygen in the muscles) as well as to break down lactic acid and waste products. Increased post-exercise oxygen consumption (EPOC) is a key factor in the recovery process. This process takes a short time after brief, low-intensity exercise but can take days after an endurance race.

During exercise, the body's energy sources become partly depleted and create an energy deficit that must be repaid by the oxidative system during post-exercise recovery. During the recovery phase the heart rate remains elevated above the baseline heart rate until complete homeostasis has been attained. Scientific studies have shown that endurance athletes have a faster recovery after exercise than sprinters or recreational athletes. There are, however, no existing models that can accurately calculate the oxygen deficit incurred nor the kinetics of the recovery curve.

The present invention not only explains the kinetics of the active exercise heart rate curve, as explained previously, but also the kinetics of the passive recovery curve. The HRK theory, underlying the present invention, postulates that the two phases share the same kinetic system. Just like the activity curve, the recovery curve is also assumed to be divided into multiple (up to six) components, separated by evenly spaced transition points, referred to as recovery transition points, but in the reverse order compared to the activity curve. The two phases of the heart rate response are assumed to complement each other within the boundaries of the cardiometabolic framework. FIG. 19 explains the kinetics of heart rate recovery.

FIG. 19 shows how the recovery curve is divided into six additive heart rate components, that together add up to the momentary recovery heart rate. These components are directly comparable to the ones described previously for the activity curve. As soon as each successive component deficit is fully repaid, there is a corresponding break or transition in the declining recovery curve. There are five such recovery transition points (R1–R5) on the recovery curve, corresponding to the transition points of the activity curve, as well as a start point (R0) and an endpoint (R6). The start-point and the first four recovery transition points (R0-R4) are assumed to be evenly spaced in heart rate. The recovery point interval ($R_i$), ranging between R0 and R4, equals the transition point interval (T0 of the previous activity curve, i.e. the activity curve during the activity immediately preceding the recovery phase, thus confirming the direct relationship between the two connected curves. The time ratios of the first four recovery transition points (R1-R4) reflect the time ratios of the corresponding recovery transition points. On the other hand, the time ratio between the lowest recovery transition points (R4-R6) is variable and depends on the intensity and duration of the activity. The recovery curve can also be divided into two major segments, i.e. the Component recovery (R0–R4, or $R_C$) and the Recovery window (R4-R6). The $R_C$ range is much narrower if the endurance level is high and subsequently, the recovery window will be much wider. A wide recovery window greatly increases the speed of recovery and decreases the time to re-attain pre-exercise homeostasis.

Heart Rate Recovery Kinetics

As explained previously in FIG. 19, the transition points on the activity curve are directly reflected in the corresponding recovery transition points on the recovery curve. According to the HRK theory, the transition points reflect the recruitment and partial depletion of the energy systems and similarly, the recovery transition points are assumed to reflect the replenishment of those same systems. Just like the T4, T5 and T6 points are assumed to reflect the partial depletion or a lower steady-state of the B, C and D-systems, the R4, R5 and R6 points are assumed to reflect the complete replenishment of these respective energy systems.

The HRK bioenergetic model, developed by the inventors, is based on a novel five-tank hydraulic model that can correctly simulate the kinetics of exercise and recovery. The model assumes that the five tanks, representing the five energy systems, are partially or completely drained during the activity phase, and subsequently refilled again during passive recovery. The model also assumes that all the energy derived from the A-D systems during the activity phase, must be repaid by the oxidative system during recovery. It is assumed that the oxygen deficit incurred is directly reflected in a corresponding heart rate deficit, in relation to the maximum heart rate for the activity. The relative contribution of the five energy systems during activity can be seen directly from the heart rate curve, with the momentary heart rate always reflecting the relative contribution of the oxidative E-system. The graph in FIG. 20 explains the concept of heart rate recovery kinetics, according to the HRK theory.

The heart rate deficit incurred within each system can also be seen directly from the heart rate graph. The T6 point represents the maximum heart rate for the activity and the heart rate deficit within the D-system can be seen directly as the triangular area between the T6 heart rate and the F-line (see FIG. 2). Similarly, the heart rate deficit within the C-system can be seen directly as the triangular area between the F-line and the E-line. The triangular shapes of the C- and D-areas, reflect the linear decline in the contribution from these systems. The A- and B-systems are both activated at the beginning of the activity, and therefore the heart rate deficit within those systems reflects the narrow area between the T0 start point and the T3 and T4 points, respectively. The different shapes of these systems are explained by exponentially declining rates of depletion of those systems (see FIGS. 4, 5 and 11). As shown in FIG. 20, the C- and D-systems account for almost all the heart rate deficit after prolonged exercise.

The HRK theory assumes that the accumulated heart rate deficit after sub-lactic exercise, is repaid in due course during recovery, with a 1:1 repayment ratio. After sub-lactic exercise, the system deficits (A-D) are directly reflected as vertically flipped areas under the recovery curve. This does, however, not mean that there is a perfect symmetry between deficit and repayment on the activity and recovery graph. The speed of recovery is directly dependent upon the endurance level and a wide recovery window will cause the recovery duration to be much shorter than the activity duration. Conversely, a narrow recovery window (low endurance level) will slow down the speed of recovery and make the recovery duration much longer than the activity duration. The heart rate typically declines in distinct linear phases during passive recovery. As soon as each successive component deficit is fully repaid, there is a corresponding break in the declining recovery curve at the respective recovery points (see FIGS. 4 and 5).

The recovery kinetics explained in FIG. 20 apply to sub-lactic activity, i.e. with an intensity below the lactate threshold. All lactic activity (intensity above the lactate threshold) will, on the other hand, have a higher repayment time ratio, depending on the intensity of the activity. For an intense activity, like long sprints or middle-distance running, the repayment time ratio can be extremely high, and the repayment time can easily be more than 30 times longer than the duration of the activity (not shown here).

Tests and Analysis

Based on the physiological hypothesis described herein, a series of exercise tests has been developed to produce heart rate data, suitable for analysis. The sections below cover and explain the various types of tests, and the analytical process involved in their analysis.

Tests

It is assumed that the method can be applied to the exercise-induced heart rate response from any kind of activity involving an increase in muscle contraction. The method can therefore be adapted to the testing and analysis of performance in various sports and activities, such as walking, cycling, swimming, rowing, cross-country skiing etc. In each case, the result will be specific to the type of activity tested. Cycling, for example, is not a whole-body exercise and therefore elicits a lower heart rate response than running. The table below shows a summary of the different tests.

TABLE 2

A summary of the various types of tests for different activities and intensities.

| Activity | Type | Intensity | Duration | Warm-up | Recovery |
|---|---|---|---|---|---|
| Walking | Walking test | Medium | 30-60 min | No | Optional |
| Running | Slow test | Low | 30-60 min | No | Optional |
| Running | Medium test | Medium | 25-45 min | No | Optional |
| Running | Racing test | High | 10-20 min | 5 min + R | Optional |
| Running | Power test | Very high | 5-10 min | 5 min + R | Optional |
| Running | Sprinting test | Near maximal | 1-2 min | 5 min + R | Optional |
| Cycling | Cycling test | High | 10-20 min | 5 min + R | Optional |
| Skiing | Skiing test | High | 10-20 min | 5 min + R | Optional |
| Rowing | Rowing test | High | 10-20 min | 5 min + R | Optional |
| Other | Undefined | Undefined | Undefined | Undefined | Undefined |

Walking Test

Although the method has been described here for running, it can just as well be applied to the testing and analysis of walking performance. A walking test is ideal for either non-athletic or elderly people but is less suitable for athletic people, since the effort may be too low to produce a testable heart rate response. The test can be performed either outdoors or indoors on a treadmill. To maximize the heart rate response and enhance the accuracy of the analysis, the walking test should be performed at near maximal walking speed for a duration of at least 30 minutes. A session of passive recovery, post-exercise is preferred at least after the first test. The recovery must be as passive as possible to produce a clean and undisturbed recovery curve, i.e. preferably in a sitting or lying position, minimizing all muscle activity as much as possible for at least 5-10 minutes post-exercise. The resulting heart rate response can be analysed by the heart rate model and even normalized for running, using user-specific conversion factors. An easy walking test may therefore produce an estimate of potential running performance, such as maximum running speed, maximum heart rate and potential running times.

Running Tests

There are five different types of running tests, as described in Table 2. The tests differ in the relative level of intensity and a shorter duration is required for the more intensive tests. The most suitable test for a specific athlete depends on the endurance level. Endurance athletes will typically require a higher level of running intensity to produce a testable heart rate response.

All the test-types are sub-maximal, meaning that the individual is not required to perform towards maximum effort or exhaustion. In the more intensive tests for advanced athletes, a relatively high effort-ratio may, however, be preferred to enhance the validity of the test. All running tests can be performed either outdoors, or indoors on a treadmill.

A constant or near-constant, running pace is preferred during a non-stop running test. For outdoor tests, a relatively flat running route and low-wind conditions are optimal for best results. The athlete should also be well rested to produce optimal results. A short warm-up and recovery are recommended prior to the more intensive tests. A passive sitting or lying recovery for at least 10 minutes post-exercise is required as a part of the first test of a new user, to accurately identify the user's heart rate profile. The recovery part is optional in later tests but preferred to enhance the accuracy of the analysis. Passive recovery is especially important for low intensity tests, to fine-tune the analysis of a typically flat and noisy activity curve.

The three fastest running tests (racing-, power- and sprinting tests) are all performed at lactic speeds (above the lactate threshold speed) and preferred as the first test, since they can be used to identify the user's heart rate profile. At lactic speeds, the aerobic base time (X) starts drifting to the right and exhaustion thus occurs much quicker than at sub-lactic speeds. The sudden and disproportional increase in heart rate elevation (slope) at lactic speeds makes it possible to identify the P-value from a single lactic test. Performing the lower-intensity tests is ideal, once the user has activated his or her running profile. It is also possible to perform more than one test in the same testing session.

Data Analysis

The functionality of the application (App) involves the analysis of heart rate data from exercise activity, based on a combination of automatic assessment and user selection. The user records an exercise session with his or her own heart rate monitor and the App retrieves the data from the user's account, such as Polar, Garmin or Apple. First, the App automatically performs a basic assessment of the activity and the user is then prompted to use the activity as a profile test. After selecting an activity as a potential profile test, the user is again prompted for additional information to categorize the activity. Table 3 summarizes the whole process.

TABLE 3

The testing process of the application.

| Level 1 | Level 2 | Level 3 | Level 4 | Level 5 |
|---|---|---|---|---|
| Activity recorded Summary (automatic) Profile test (selection) Activity (selection) | Cycling Walking Running | Indoor Outdoor | Track Treadmill Race Training | Speed Warm-up Recovery Distance Slow pace Medium pace Race pace Power run Sprinting Warm-up Recovery |

TABLE 3-continued

The testing process of the application.

| Level 1 | Level 2 | Level 3 | Level 4 | Level 5 |
|---|---|---|---|---|
| Validation | | | | |
| | Rejection | | | |
| | Approval | | | |
| Smoothing | | | | |
| Calibration | | | | |
| P-detection | | | | |
| Analysis | | | | |
| | Cardiolysis | | | |
| | Recovery analysis | | | |
| | Driftline analysis | | | |
| Result | | | | |
| Profile | | | | |
| update | | | | |

The testing process is thus a selection-based process on five levels. The process includes seven major computational steps, as explained in the sub-sections below. In an optional configuration the testing process is not selection-based but rather fully automatic.

SUMMARY

The first major step of the Cardiolysis process is a primary summary of the activity. This action is automatic and based on the available information. The summary updates when the user has entered additional information about the activity. The information summarized, include the date, time, type and duration of the activity. The basic calculations summarized, include the average and max speed, average and max pace, and the average and max heart rate. Initial performance indicators include the K-score (beats/km) and the Beat-score (m/beat) for each km and for the whole activity. The performance is rated as class A, B and C (colour coded), based on a comparison of the K-score and the Beat-score to the current active profile values. A performance improvement based on the initial summary is used to update the user's profile, even if the activity is not selected as a profile test. However, if the activity is selected as a profile test, it will have a stronger effect on the profile.

Selection

Based on the activity summary, the user can select to use the recorded activity as a potential profile test, depending on approval by the App. The user also selects or confirms the type of activity, such as cycling, walking or running, and then selects sub-categories on three levels for the selected activity. For example, in the case of treadmill running (see Table 3), the user first selects Indoor and then Treadmill and finally Speed, Warm-up and Recovery. The user-based selection helps to categorize the profile tests to optimize the analysis and facilitate validation of the test.

Data Processing

The application can use several methods to analyse test heart rate data. A schematic drawing illustrating data processing (validation, smoothing/filtering and calibration) and subsequent data analysis is shown in FIG. 36.

Validation

Before starting the analysis, it is necessary to validate the data. The App must determine if the data fulfils several basic test criteria. For example, if the test is too short or if the dataset is flawed, irregular or deviant, it may be rejected by the App. The dataset is validated through testing of various criteria, such as described below.

The dataset is invalid if it contains no speed information (GPS or user selected).

The dataset is invalid if it is too high in variability, that is if the accumulated point-to-point slope divided by the number of points is too high compared to the overall slope.

The minimum activity duration of Sprinting tests, Power runs and other tests, is 30 seconds, 5 minutes and 15 minutes, respectively.

The dataset is invalid if calculated Beat-score deviates from profile Beat-score>15%.

The dataset is invalid if calculated Endurance deviates from profile Endurance by >10%.

The dataset is invalid if calculated Max speed deviates from profile Max speed by >5%.

The dataset is invalid if there is a gap of >60 seconds between two adjacent points.

The dataset is invalid if average heart rate is >200 bpm or <100 bpm.

The dataset is invalid if the overall slope is >0.4 bpm/s or <0 bpm/s.

Smoothing

The next step of the process is the filtering and smoothing of the data. The dataset is filtered through a sequence of filtering methods, as described below.

The start of the activity is detected, and data removed that do not belong to the activity.

The start point is estimated by locating the first prolonged and rapid heart rate increase.

All data measured after the run ended are removed from the dataset. The end point is estimated by locating the point at which the heart rate starts to decrease drastically.

To enhance the sensitivity of the analysis, it is also necessary to detect and remove outliers, and reduce the noise in the dataset. A best fit to the dataset is calculated using a simplified Solver method. All defined outliers are removed. This process is repeated 4 times and the filtering range decreased for each repetition.

Finally, the data is smoothed using a moving average with a range of 60 seconds.

Speed Calibration

After adjusting the shape of the heart rate curve, it must be calibrated for the individual so the threshold speed can be translated into actual speed units. This can be done if the actual constant speed is known, such as from a treadmill run or from an outdoor run with GPS sampling.

To calibrate speed, the method uses the y-intercept of the E-line ($E_a$), the heart rate thresholds (p1 and p3), the endurance (E) and the known test speed (v) (see FIG. 20). The key in this context is the fact that the aerobic threshold (V1) has the following relationship with endurance (E), where V1 is calculated as a ratio (V1%) of V5 (maximum speed): V1%=E/(E+1). V1% further has the following relationship with V2, the anaerobic threshold: V2%=V1%+(1-V1%)/4. Once V1 and V2 have been analysed in this way, the test speed (v) can be calculated as a ratio of V5 and then all other speed thresholds as a result. This means that the maximum running speed can be identified from submaximal running at low speeds.

The following list shows the calculations involved in the calibration process, with example calculations based on P=47, E=40% and v=14 kph. These values give an $E_a$ of 148.7 bpm, heart rate thresholds of 100.7 bpm (p1) and 188 bpm (p3=HRmax), and a HR threshold interval (p) of 43.6 bpm:

$$V1\% = E/(E+1) = 0.4/(0.4+1) = 28.6\%$$

$$V_i\% = (1-V1\%)/4 = (1-0.286)/4 = 17.9\%$$

$$v\% = V1\% + ((E_a - p1)/(p))(V_i\%) = 0.286 + ((148.7 - 100.7)/(43.6))(0.179) = 48.2\%$$

$$V2\% = V1\% + (1-V1\%)/4 = 46.4\%$$

$$V1 = v/v\%(V1\%) = 14/0.482(0.286) = 8.3 \text{ kph}$$

$$V2 = v/v\%(V2\%) = 14/0.482(0.464) = 13.5 \text{ kph}$$

Through this unique and innovative process of speed calibration, any calculated threshold speed can be translated into actual speed. This includes all five speed thresholds, the optimal speed and the lactate threshold speed.

P-Detection

The heart rate model identifies P from lactic tests (>VL speed) through a process of iteration, based on the three input parameters; E, P and V. The model first selects an initial P value, which is clearly below the range of possible values for all users, such as for example 38 bpm. The model then starts the iterative process by adjusting the E and V values and minimizing the deviation (sum of squared error) between the data and the model fit. This process is continuously repeated by raising the P value in steps of 0.5-1.0 bpm and solving for E and V each time. The summed deviations decrease towards a minimum as the input P value approaches the actual user value. For higher input P values, above the user value, the total deviation remains low and stable. The heart rate model selects the lowest of these minimum P values as the actual user value.

Analysis

The main method is named Cardiolysis and is based on solving for best fit between the heart rate model and the heart rate data. The App can also use Recovery analysis to analyse recovery tests without solving for best fit. The third approach is the Driftline multiple test analysis, which involves the partial analysis and syncing of multiple tests. These three main methods are summarized below.

Cardiolysis

Having identified the P value, the analysis can be completed with the iterative process of Cardiolysis. FIG. 22 explains the Cardiolysis process step by step with an illustrative example of iterations to a set of exercise-induced heart rate data. This dataset was of good quality and did not require any filtering or smoothing. The heart rate model finds the best fit to the data by adjusting the E and V variables and the last graph (D) shows the fit producing the smallest error. The spreadsheet in Table 4 shows some of the calculations for the four different graphs (see List of calculations for complete details). This runner was found to possess 62% endurance, an HRmax of 220 bpm and a max speed of 19.3 kph. The lactate threshold speed was calculated as 10.9 kph, maximum distance as 40.5 km and a potential race time of 54:30 minutes was predicted for the 10 km race. This is of course only an illustrative example as the actual iterative process includes hundreds or thousands of iterations from start to finish.

TABLE 4

Step by step Cardiolysis according to the four graphs in FIG. 22.

| Nr. | Parameter | Symbol | A | B | C | D | Unit |
|---|---|---|---|---|---|---|---|
| 1 | Endurance | E | 25% | 25% | 40% | 53% | % |
| 2 | Heart rate level | P | 50 | 55 | 55 | 55 | bpm |
| 3 | Metabolic speed | V | 2.00 | 2.00 | 2.05 | 2.05 | V |
| 4 | Running speed | v | 10.0 | 10.0 | 10.0 | 10.0 | kph |
| 7 | Aerobic base time | X | −64.0 | −64.0 | −90.4 | −122.0 | min |
| 23 | Maximum HR threshold | p3 | 200 | 220 | 220 | 220 | bpm |
| 24 | Aerobic HR threshold | p2 | 145 | 160 | 169 | 176 | bpm |
| 25 | Anaerobic HR threshold | p1 | 90 | 99 | 118 | 131 | bpm |
| 29 | Lactic heart rate | pL | 163 | 180 | 186 | 190 | bpm |
| 31 | Max speed threshold | V5 | 25.0 | 25.0 | 21.2 | 19.3 | kph |
| 32 | Anaerobic max speed threshold | V4 | 20.0 | 20.0 | 17.4 | 16.2 | kph |
| 33 | Aerobic max speed threshold | V3 | 15.0 | 15.0 | 13.6 | 13.0 | kph |
| 34 | Anaerobic speed threshold | V2 | 10.0 | 10.0 | 9.8 | 9.9 | kph |
| 35 | Aerobic speed threshold | V1 | 5.0 | 5.0 | 6.0 | 6.7 | kph |
| 37 | Lactate speed threshold | VL | 11.7 | 11.7 | 11.1 | 10.9 | kph |
| 50 | Optimal speed | vOpt | 7.56 | 7.56 | 8.18 | 8.57 | kph |
| 66 | Maximum running time | tMax | 186 | 186 | 230 | 289 | min |
| 67 | Maximum running distance | Dmax | 23.4 | 23.4 | 31.4 | 41.3 | km |
| 69 | Lactic distance | DL | 6.2 | 6.2 | 8.4 | 11.1 | km |
| 93 | Predicted 10 km race time | t10km | 58.21 | 58.21 | 56.58 | 56.01 | m:s |
| 94 | Predicted half-marathon race time | tHM | 2.29.16 | 2.29.16 | 2.15.39 | 2.08.52 | h:m:s |

Recovery Analysis

The Cardiolysis method is based on solving for best fit between the heart rate model and the heart rate data. The recovery analysis method, on the other hand, is based on the heart rate recovery kinetics. The method identifies the recovery interval from a passive recovery session and uses it to fine-tune the analysis of the connected activity curve. Through the detection of two or more recovery points, the recovery interval ($R_i$) can be calculated and thus also the transition interval (T0) of the activity curve. The baseline heart rate (P) and the maximum heart rate can also be calculated from the recovery points. The analysis can also be done by solving for best fit, without the isolated detection of the recovery points.

FIG. 23 shows the fitting and analysis of a sub-lactic recovery test. The figure shows an example heart rate response produced after running outdoors for 36 minutes at a sub-lactic pace (under the lactic threshold pace), followed by a passive recovery for another 24 minutes post-exercise. The activity curve is relatively noisy, but the smooth recovery curve enhances the accuracy of the analysis. The dataset is fitted with the heart rate model, producing a fine fit for the recovery phase.

The first step of the process involves the fitting of the exercise curve and the identification of the E-line parameters. The second step involves the fitting of the recovery curve and the identification of the recovery interval ($R_i$). As previously explained in FIG. 19, the R3 and R4 points can often be identified from clear breaks in the recovery curve. For runners with very high levels of endurance it is often easiest to identify the R5 recovery point. The third step involves calculating the aerobic base time (X) from the following equation: $X=2(R_i/E_b+6)$, where X equals the aerobic base time, $R_i$ the recovery interval and $E_b$ the E-line slope. The fourth step involves the calculation of endurance (E) from the X-value. The calculation process is shown also below:

$$X=2(R_i/E_b+6)=78.8 \text{ min}, E=\log(X/36)=34.0\%$$

$$p1=E_a-X(E_b)=94.7 \text{ bpm}, p1\%=E/(E+1)=25.4\%,$$
$$pp=p1/p3=(0.25+p1\%)=50.4\%$$

$$p3=P3=p1(1/0.504)=188 \text{ bpm}, p=(p3-p1)/2=46.6 \text{ bpm}$$

$$P=P3/4=47 \text{ bpm}, V=1+(E_a-p1)/p=2.09$$

The model thus calculates 34% endurance (E) and a HRmax (P3) of 188 bpm from this test.

Exercise tests can be designed specifically to enhance the detection of specific recovery points. A high-intensity test (fast test) with a relatively high effort-ratio is ideal to determine the R3 point accurately and thus the $R_i$ interval. On the other hand, a medium-intensity test is ideal to determine the R4 and R5 points accurately. A combined exercise- and recovery test is preferred as the first test of an athlete, since it has a much greater analytical power, especially for endurance athletes that typically produce very flat activity curves. A recovery test will also enhance the analysis of tests with large variations in intensity and heart rate.

It should be underlined that recovery tests are only required for the first test of an individual. Once HRmax has been identified, the model can subsequently analyse any type of test by the individual, without analysing the recovery phase. The analysis can, however, be more accurate if a passive recovery phase is included in the test. All tests must be performed in accordance with the test directions, to be suitable for analysis.

Driftline Analysis

When P is not known, and two or more sub-lactic tests at different speeds are available from the same user, the method (for example as implemented in an App) can use the Driftline method to sync the tests and perform a complete analysis. This method is based on the kinetics of the activity heart rate curve, as shown in FIG. 24. It is assumed that the cardiovascular drift is reflected in the elevation (Drift) of the linear E-component (Driftline) during the test. Referring to the graph on FIG. 24*a*, the Driftline method is based on the negative relationship between Drift (=$R0-E_a$) and endurance (E). In the example shown in FIG. 24, the total E-line Drift during the test equals 13 bpm (i.e., the HR at end of test subtracted by the HR at $E_a$). The relative magnitude of the Drift at any given point in time is determined by the elevation of the E-line (=Drift) in relation to the Base response (Base). The base response is defined as the accumulated number of non-drift heart beats between the p1 threshold and the y-intersect of the E-line ($E_a$), i.e. Base= (($E_a$-p1)t)). In the example in FIG. 24*a*, the Base equals 924 beats (28 minutes 33 bpm).

The ratio between the Drift and the Base is defined as the Drift-ratio (Dx=Base/Drift). Dx is directly correlated with endurance (E) and the aerobic base time (X):

$$Dx=36 \cdot 10^E=X$$

This means that the relative magnitude of the Drift is always the same, up until the T5 transition point and is only dependent on endurance, regardless of the duration of the activity.

The Driftline method uses the relationship between Drift and Base to sync together two or more running tests performed at different speeds. If the regression constants ($E_a$ and $E_b$) are known for two tests, the Drift-ratio can be calculated for both tests, based on a range of p1 input values. The method is explained in FIG. 24*b*, for two different tests with known E-line parameters ($E_a$ and $E_b$). A range of test input p1-values (70, 80, 90, 100 and 110 bpm) is used to calculate a corresponding range of output E-values (endurance) for each of the two tests. This creates a set of test E-values for each test that have independent polynomial relationships with p1. The user's correct p1- and E-values can then be calculated from the intersect between those two polynomial curves as shown in FIG. 24*b*. In this example, p1 and E are identified as 94.7 bpm and 34.0% and all remaining calculations are straightforward, as shown below:

$$p1\%=E/(E+1)=25.4\%, p1/P=1+4 \cdot p1\%=2.01 \text{(relative aerobic threshold)}$$

$$P=p1/(p1/P)=94.7/2.01=47.0 \text{ bpm (the heart rate level interval)}$$

$$P3=4P=p3=HR\text{max}=188.0 \text{ bpm } (HR\text{max, only reached at } VL \text{ to exhaustion})$$

$$p=(P3-p1)/2=(188-94.7)/2=46.7 \text{ bpm (the heart rate threshold interval)}$$

$$p2=p1+p=94.7+46.7=141.4 \text{ bpm (the anaerobic threshold)}$$

$$pL=p2+p/3=141.4+46.7/3=156.9 \text{ bpm (the lactic threshold heart rate)}$$

A clear distinction should be made between the heart rate level interval (P) and the heart rate threshold interval (p), see page 20. At a relatively low endurance level (such as E=34% in this example) both these intervals may be very similar in size, but at higher endurance levels p is much smaller than P because the thresholds are more closely spaced.

Specific Calculations

This section shows a summary of some of the main calculations (see the List of calculations).

Aerobic Endurance (E)

Aerobic endurance (E) reflects the alignment of speed thresholds and is calculated from the intercept (X) of the backwards forecast E-line with the aerobic heart rate threshold (p1).

$$X=36e \quad e=10^E$$

$$E=\log(e)=\text{aerobic endurance}$$

$$E=\log(X/36)$$

$$E=\log(X/36)=\log((E_a-p1)/(36E_b))$$

where e is the endurance base (scale 1-10) and X is the endurance base time (scale: −36 to −360 minutes). $E_a$ and $E_b$ are the oxidative E-line constants (in bpm units) and p1 is the aerobic heart rate threshold (in bpm units). E is presented on a scale of 0-100%. As stated previously, the E value, such as defined here, presents the first physiologically sound definition of aerobic endurance, reflecting the alignment of energy thresholds.

Speed Thresholds (V1-5, VL, VSL) and Maximum Speed (Vmax)

To calculate these parameters, one must first solve for E, P and V (see above) and then perform a speed calibration, based on the test speed (v). This leads to the identification of the two lowest speed thresholds, V1 and V2 and the threshold interval, $V_i$:

$V1\% = E/(E+1) V_i\% = (1-V1\%)/4$ $v\% = V1\% + ((E_a - p1)/(p))(V_i\%)$ $V2\% = V1\% + (1-V1\%)/4$ $V1 = v/v\%(V1\%) = $ aerobic speed threshold $V2 = v/v\%(V2\%) = $ anaerobic speed threshold $V_i = V2 - V1$ where E is the aerobic endurance (scale 0-100%), Vi % the threshold interval percentage and v % the relative test speed. V1% is the V1 percentage (=V1/V5) and V2% is the V2 percentage (=V2/V5). $E_a$ and $E_b$ are the oxidative E-line constants (in bpm units), p1 is the aerobic heart rate threshold (in bpm units) and p is the heart rate threshold interval. $V_i$ is the speed threshold interval and v the test speed. Knowing the V2 threshold and the threshold interval ($V_1$), other speed thresholds can be calculated by way of direct extrapolation:

$VL = V2.333 = V2 + V_i/3 = $ lactate speed threshold $V3 = V2 + V_i/3 = $ max aerobic speed threshold $VSL = V3.333 = V3 + V_i/3 = $ super-lactic speed threshold $V5 = V2 + 3V_i = V$max = maximum speed threshold = maximum running speed Heart Rate Thresholds (p1-3), HRmax and LT Heart Rate (pL)

To calculate these parameters, one must first solve for E, P and V (see above) and then perform a speed calibration, as explained above. Then, the heart rate levels can be calculated by way of extrapolation from the known P (heart rate level interval).

$P3 = 4P = $ maximum heart rate (HRmax)

$P2 = 3P = $ anaerobic heart rate level $P1 = 2P = $ aerobic heart rate level $P0 = P = $ resting heart rate (HRrest)

The key to finding the heart rate thresholds is the relationship between the V1 percentage (V1%) and the p1 percentage (p1%). Based on p1%, the heart rate threshold interval (p) can be calculated and all the heart rate thresholds by way of extrapolation:

$p1\% = px/P3 = V1\%$  $px = p1 - P0 = p1$ elevation $p2 = p3 - p = $ anaerobic heart rate threshold $p1 = P + p1\%(4P) = $ aerobic heart rate threshold $p = (p3 - p1)/2 = $ heart rate threshold interval $pL = p2 + p/3 = $ lactic heart rate threshold $p3 = P3 = p1 + 3(pL)/2 = $ maximum heart rate (HRmax)

Time and Distance Thresholds

As will be explained later (Example 2), the race time predictor associated with the invention, can be used to calculate the lowest possible running time (Runtime) over any distance and the greatest distance (Rundistance) that an individual could run at any speed in a non-stop race. Example calculations are presented in Table 7. The predictor can also be used to predict a theoretical maximum running distance (Dmax) and the theoretical maximum running time (tMax). It is assumed that the maximum non-stop running distance is only reachable when running at the individual optimal speed (Vopt), as explained in FIG. 13. Below is the list of calculations, with example calculations for the specific case of E=40% and Vmax=28.0 kph.

$e = 10^E = 2.51$  $X = 36e = 90.4$ minutes $V1\% = E/(E+1) = 28.6\%$

Base speed = $v1 = V1\% \cdot V$max = 8.0 kph

Speed threshold interval = $V_i = V$max$/(4 \cdot (E+1)) = 5.0$ kph

Optimal speed = vOpt = $v1 + (5/3) \cdot Vi = 11.33$ kph

Maximum non-stop running time = tMax = $24 \cdot Xf = 2X = 181$ minute

Maximum non-stop running distance = Dmax = vOpt·tMax/60 = 34.2 km

The Heart Rate Model

In an application of the present invention, the method calculates and predicts exercise-induced heart rate as a function of time. This is done by dividing the heart rate curve into six components, A, B, C, D, E and F, and producing a specific function for each component. In an optional configuration, the algorithm can also be configured to divide the heart rate curve in to five components, A, B, C, D and E. The heart rate model first calculates the coordinates of all the curve points (T0–T6, i.e. starting point T0, endpoint T6 and transition points T1–T5), based on the cardiometabolic parameters, E, P and V. The calculations of the curve points are based on the kinetics of the heart rate curve and summarized in lines 62-67 in the List of calculations. The model then simulates the heart rate curve by connecting the points with the respective component functions.

The heart rate vs time relationship during the first component (A) and the last two components (E and F) can be described with linear regression functions of the type: Y=a+bX, where Y is the heart rate (the dependent variable), X is time (the independent variable), a is the y-intercept and b is the slope of the line. The heart rate vs time relationship during the three remaining, intermediate components (B, C and D) can be described with logarithmic functions of the type Y=a+b(Ln(X)), where Y is the heart rate (the dependent variable), X is time (the independent variable), a is the y-intercept and b is the exponent. FIG. 25 shows an illustrative heart rate curve from the heart rate model with transition- and endpoints (T1–T6) and the respective equations indicated.

The start point, T0 (not shown in FIG. 25), is determined as the initial valid heart rate point of the exercise. To summarize, the heart rate curve is initiated at the starting point (T0 at time t0) and completed at the endpoint (T6 at the time t6). The six components are separated by the five transition points, T1–T5, at the respective times of t1-t5.

As shown in FIG. 25, the heart rate during the linear A, E and F components is simulated through linear regression functions. The function used for the E component depends on whether the threshold speed is below or above the lactate threshold speed (VL), as indicated. For speeds >VL speed, the heart rate during the E component is calculated with the following function:

$$HR(E_t) = T4 - (PS - T4)(t - t4)/(t6 - t4),$$

where T4 stands for T4 heart rate, PS stands for the supramaximal heart rate, and t, t4 and t6 stand for times at t, T4 and T6, respectively. PS is calculated with the following equation:

$$PS = P3 + (V - 7/3)p,$$

where P3 stands for HRmax, V for threshold speed and p for heart rate threshold interval. Table 5 shows the list of equations for the six components of the heart rate curve.

The calculations of the heart rate and timing of the curve points (T0–T6, t0–t6) are summarized in the List of calculations. The line parameters (a and b) for the linear A component are calculated as: $A_a = T_n - t_n(b)$ and $A_b = (T_n - T_{n-1})/(t_n - t_{n-1})$.

TABLE 5

A list of equations for the six components of the heart rate curve (A-E). The transition point interval during each component is indicated.

| Component | Interval | Heart rate vs time functions |
|---|---|---|
| A | T0-T1 | $HR(A_t) = A_a + A_b(t)$ |
| B | T1-T2 | $HR(B_t) = B_a + B_b(Ln(t))$ |
| C | T2-T3 | $HR(C_t) = C_a + C_b(Ln(t))$ |
| D | T3-T4 | $HR(D_t) = D_a + D_b(Ln(t))$ |
| E | T4-T5 | $HR(E_t) = IF(V < VL, E_a + E_b(t),$ $T4 + (PS - T4)(t - t4)/(t6 - t4)$ |
| F | T5-T6 | $HR(F_t) = F_a + F_b(t)$ |

The curve parameters (a and b) for the logarithmic functions (B, C and D) are calculated as:

$$BCD_a = T_n - Ln(t_n)b \text{ and } BCD_b = (T_n - T_{n-1})/((Ln(t_n) - Ln(t_{n-1}))).$$

The line parameters for the linear E component are different for the three intensity phases and calculated as:

$$E_a(V < 7/3) = p0 + V(p) \text{ and } E_aL(V >= 7/3) = T4 - t4(E_bL)$$

$$E_aSL(V > 10/3) = (pL - ((pL - p2)(3(V - 10/3)/2)))$$

$$E_b = (E_a - p1)/X_E$$

where $E_aL$ stands for $E_a$-lactic (V>VL), $E_aSL$ stands for $E_a$-superlactic (V>VSL), pL stands for lactic heart rate, p for the heart rate threshold interval, and p0, p1 and p2 stand for the respective heart rate thresholds. $E_bL$ stands for the lactic E-slope and is calculated as:

$$E_bL = (PS - T4)/(t6 - t4)$$

$X_E$ stands for the E-line base point (in negative time) and is calculated as:

$$X_E = IF(V > 7/3; ((E_a - p1)/L_b); X))$$

where $L_b$ stands for lactic slope (see List of calculations). The line parameters for the linear F component are calculated as:

$$F_a = p0 + F_aV(p)$$

$$F_b = IF(V > 5/3; ((F_a - p2)/X_F; 0))$$

where $F_aV$ stands for F line V intercept, p for the heart rate threshold interval, and p0 and p2 stand for the respective heart rate thresholds. $X_F$ stands for the F-line base point (in negative time) and always equals $X_E$. The E- and F-line intercepts with the y-axis are calculated as:

$$E_aV = 2 + (E_a - p2)/p$$

$$F_aV = IF(V > 7/3, (E_aV + \frac{1}{3}), (V + \frac{1}{3}))$$

List of Equations $$\text{Endurance} = E = \frac{V1}{V5 - 1} = \frac{V1}{4Vi} = \frac{1}{1 - V1\%} - 1 = \log(e) = \log\left(\frac{X}{36}\right)$$

$$\text{Endurance base} = e = \frac{X}{36} = 10^E \quad p1\% = V1\% = \frac{E}{E + 1}$$

$$\text{Aerobic base time} = X = 36e \quad X \text{ factor} = Xf = \frac{X}{12}$$

$$\text{Maximum speed} = Vmax = VL\left(\frac{E + 1}{E + 1/3}\right)$$

$$\text{Lactic threshold} = VL = Vmax\left(\frac{E + 1/3}{E + 1}\right)$$

$$E = \left(\frac{VL + \frac{Vmax}{3}}{Vmax - VL}\right)$$

$$\text{Maximum heart rate} = HRmax = \frac{Vmax * Vz}{Pz\%} = 4P$$

$$\text{Submaximal heart rate} = HRsubmax = p1 + \frac{3p}{2}$$

$$\text{Supramaximal heart rate} = PS = p3 + p*\left(V - \frac{7}{3}\right)$$

$$\text{Time factor} = tf = \frac{X}{12}*\left(V - \frac{7}{3}\right)*e^{(0.9318 - 0.375*\ln(X))}$$

Maximum distance = Dmax = Tmax * vOpt

Maxtime = tMax = 24 * Xf = 2X

Runtime = tf * tT

Aerobic threshold = p1 = P + p1% * 4P = P + p1 * HRmax $$\text{Drift ratio} = Dx = 10^E = X = 2\left(\frac{Ri}{Eb} + 6\right)$$

$$\text{Heart rate} = HR = Vz(x) + Pz \quad Pz\% = 1 - \frac{(2E - 2E^2)}{E + 1}$$

F-line intercept = Fa = Ea + p/3

T-times:

$t1 = 24 \times 8^{-V}(< V2.333) \quad t2 = 48 \times 8^{-V}(< V2.333)$ $t3 = 144 \times 8^{-V}(< V2.333) \quad t4 = 768 \times 8^{-V}(< V3.333)$ $t5 = (Fa - Ea)/(Eb - Fb) \quad t6 = tf * t4$ The invention is further described by the following non-limiting examples.

Example 1

Simulation of the Heart Rate Curve

Using the component equations, the heart rate model can simulate the exercise-induced heart rate curve. FIG. 26 shows an illustrative example of a heart rate curve simulation for a runner with a 188 bpm HRmax and 38% endurance (E), running at V1.81 threshold speed. The table below shows the results of Cardiolysis for this runner.

TABLE 6

The simulation of an exercise-induced heart rate curve. The table shows the calculated framework heart rates, heart rates and times, as well as time ratios between consecutive curve points (start point, transition points and endpoint). The right part of the table shows the parameters for the respective curve components.

| Points | pV (V units) | p (bpm) | t (min) | Ratio (time) | Curve components | a | b |
|---|---|---|---|---|---|---|---|
| T0 | p0.26 | 65.8 | 0 | | | | |
| T1 | p0.93 | 95.7 | 0.56 | 1 | A | 65.8 | 53.16 |
| T2 | p1.28 | 111.2 | 1.125 | 2 | B | 108.5 | 22.31 |
| T3 | p1.62 | 126.6 | 3.38 | 3 | C | 109.5 | 14.07 |
| T4 | P1.97 | 142.1 | 18.0 | 5.33 | D | 115.4 | 9.238 |
| T5 | p2.21 | 152.6 | 43.2 | 2.40 | E | 134.7 | 0.416 |
| T6 | p2.35 | 158.8 | 129.5 | 3.00 | F | 149.6 | 0.071 |

The table shows the calculated framework heart rates (p-values), and the heart rate vs time (p vs t) coordinates of the curve points, as well as the time-ratios between points. The right part of the table shows the calculated line- or curve parameters for each of the curve components. FIG. 26a shows the heart rate data from a 90-minute run from this runner. To simulate the heart rate curve, the heart rate model uses the parameters and the point coordinates as input into the component equations to connect the curve points (start-, transition- and endpoints) and create a whole curve (see FIG. 26b). Please note that the heart rate reaches a sub-max of 159 bpm at this threshold speed, 29 bpm lower than the HRmax threshold.

Example 2

Race Time Predictor

Having formulated the time-distance relationship over all distances, it is now possible to create a race time predictor to calculate the lowest possible Runtime over any racing distance. The race time predictor translates threshold speed (V) into actual speed and only requires the input of two other variables, namely Vmax (max speed) and E (endurance). Runtime can be predicted accurately over all distances from sprinting distances to ultra-long distances. Table 7 shows the list of calculations involved in the race time prediction.

TABLE 7

Calculations involved in race time prediction, based on input variables E, V and Vmax.

| | | |
|---|---|---|
| Vmax | 30.0 | Input (maximum speed, kph) |
| E | 33% | Input (endurance, %) |
| V | 2.333 | Input (threshold speed) |

TABLE 7-continued

Calculations involved in race time prediction, based on input variables E, V and Vmax.

| | | |
|---|---|---|
| e | 2.14 | $=10^{\wedge}E$ |
| X (min) | 77.0 | $=36e$ |
| V1% | 24.8% | $=E/(E + 1)$ |
| 1 − V1% | 75.2% | $=1 - V1\%$ |
| V1 (kph) | 7.44 | $=Vmax \cdot V1\%$ |
| Vi (kph) | 5.64 | $=(Vmax - V1)/4$ |
| Vopt | V1.667 | $=V \cdot (5/3)$ |
| v (kph) | 15.0 | $=V1 + (V - 1) \cdot Vi$ |
| t4 (min) | 6.00 | $=768 \cdot 8^{-V}$ |
| Time factor (tf) | 6.41 | $=X/12 \cdot \exp(0.9318 - 0.375 \cdot Ln(X)) \cdot (V - 7/3)$ |
| Runtime (min:s) | 38:30 | $=tf \cdot t4$ |
| Distance (m) | 9602 | $=v \cdot 1000 \cdot RT/60$ |

Table 7 shows example calculations for a runner with a Vmax of 30 kph and an 33% endurance (E) at a threshold speed (V) of 2.333 (VL=lactate threshold speed). The predictor predicts a Runtime of 38 minutes and 30 seconds for a distance of 9602 metres at this threshold speed. The predictor can easily be transformed to predict the Runtime over specific fixed distances, such as the racing distances in athletics and street races. The fixed predictor only requires the input of two variables (E and Vmax) to calculate the Runtime for the fixed distance. Table 8 shows a few examples of such predictions, based on widely different inputs for E and Vmax.

TABLE 8

The predicted Runtimes over specific race distances, given different combinations of maximum speed (Vmax) and endurance (E). HM stands for half-marathon and M for marathon. Time units are indicated in the last column.

| | E | | | | | | | | | |
|---|---|---|---|---|---|---|---|---|---|---|
| | 100% | | | 75% | | | 50% | | | |
| Vmax | 30 | 25 | 20 | 30 | 25 | 20 | 30 | 25 | 20 | kph |
| 60 m | 8.00 | 9.36 | 11.40 | 8.34 | 10.12 | 12.84 | 8.24 | 10.04 | 12.79 | sec |
| 100 m | 12.85 | 15.18 | 18.67 | 12.60 | 15.30 | 19.41 | 12.81 | 15.60 | 19.88 | sec |
| 200 m | 24.79 | 30.03 | 37.96 | 25.22 | 30.62 | 38.85 | 25.69 | 31.30 | 39.88 | sec |
| 400 m | 51.42 | 62.27 | 78.72 | 52.56 | 63.82 | 80.96 | 54.06 | 65.86 | 83.91 | sec |
| 800 m | 1:48 | 2:12 | 2:50 | 1:50 | 2:15 | 2:55 | 1:53 | 2:19 | 3:04 | min |
| 1500 m | 3:40 | 4:33 | 5:45 | 3:49 | 4:44 | 6:00 | 4:03 | 5:01 | 6:24 | min |
| 3 km | 7:47 | 9:27 | 11:57 | 8:09 | 9:55 | 12:36 | 8:44 | 10:38 | 13:32 | min |
| 5 km | 13:21 | 16:11 | 20:29 | 14:04 | 17:05 | 21:42 | 15:11 | 18:31 | 23:36 | min |
| 10 km | 27:46 | 33:40 | 42:39 | 29:30 | 35:53 | 45:34 | 32:18 | 39:25 | 50:21 | min |
| HM | 1:01:14 | 1:14:18 | 1:34:10 | 1:05:46 | 1:20:02 | 1:41:46 | 1:13:15 | 1:29:33 | 1:54:58 | hrs |
| M | 2:08:36 | 2:37:14 | 3:21:08 | 2:20:25 | 2:52:34 | 3:42:18 | 2:41:13 | 3:20:06 | 4:21:06 | hrs |

By adjusting the two input variables, Vmax and E, an infinite number of individual performance profiles can be created. Table 8 shows just a few examples covering a very wide range in performance, from a recreational runner running 10 km in 50 minutes to a world class endurance runner, running the marathon in 2 hours and 8 minutes. This race time predictor can predict the race performance of any runner, regardless of running ability and gives realistic predictions based on science. Available race time predictors are all based on empirical correlations to the performances of homogenous groups of advanced endurance runners. They require the input of recent racing times over one or more distances but still produce unrealistic predictions for most runners. This new race time predictor, on the other hand, requires no special user input and accommodates runners of all levels of ability.

Example 3

Maximum Distance

The maximum potential non-stop running time to voluntary exhaustion (Runtime) can be calculated as a simple product of the transition times (i.e. the time at each transition point, see Table 1). The transition times are maximized at the optimal speed (Vopt), where the last segment of the heart rate curve (the F-line) becomes parallel to the anaerobic heart rate threshold (see FIG. 13). The Runtime and the running distance should therefore also be maximized at this speed. According to the HRK theory, the C- and D-systems would both be depleted at this point and the runner would become exhausted.

FIG. 28 shows how the maximum distance can be calculated for a runner with E=40%, Vmax=30 kph and HRmax=188 bpm. The maximum distance (Dmax) can be calculated from the following equation:

$$Dmax = tMax \cdot vOpt$$

where tMax is the maximum Runtime (in hours) and vOpt is the optimal running speed (see Specific calculations for the whole process).

The calculated Dmax in this example is 36.5 km, which means that the runner would not be predicted to be physically able to run a whole marathon (42.2 km) without stopping. A world-class ultra-marathon runner with E=100% and Vmax=24.0 kph, would be able to run a non-stop distance of 168 km in 12 hours, when running at an optimal speed of 14.0 kph. Theoretically, the maximum distance could be extended considerably through regular, short recovery sessions during ultra-marathon races, but then the race would no longer qualify as a non-stop race.

Example 4

Lactate Threshold, Endurance and Maximum Speed

As explained previously, the alignment of speed thresholds reflects the level of aerobic endurance. The speed thresholds and the endurance are therefore interrelated through simple equations, as outlined below. The HRK theory suggests that the lactate threshold speed (VL) represents an upper limit to the sustainable powering of exercise through aerobic glycolysis. FIG. 29 shows that when running towards exhaustion at VL speed, the heart rate peaks as T5 at the p3 heart rate threshold. At the VL speed, the T6 point has drifted to the left to match the T5 point exactly (see also FIG. 13). This means that the D-system (aerobic glycolysis) now becomes depleted at the same time as the C-system (anaerobic glycolysis), as explained previously in FIGS. 4 and 5. At higher speeds (lactic speeds), due to a reduced availability of oxygen, the D-system is no longer able to shuttle all the pyruvate into the mitochondria for aerobic metabolism and an increasing part of the pyruvate gets reduced to lactate in the cytosol, leading to an exponential increase in blood lactate.

As indicated in FIG. 29, the lactate threshold speed equals the threshold speed V2.333 and accordingly also the threshold heart rate p2.333. This means that the E-line crosses the y-axis ($E_a$) at exactly ⅓ of the distance between the p2 and the p3 heart rate thresholds, at 159 bpm in this example. The Runtime to exhaustion at the VL speed equals exactly X/2 or 45.5 minutes in this example (since X=91 minutes). After speed calibration, the threshold speed can then be translated into actual speed, as explained on FIG. 21, and in detail on page 34.

Due to the fixed heart rate kinetics, the lactate threshold speed (VL) can also be calculated directly, if the max speed (Vmax) and the endurance (E) are known:

$$VL = Vmax\left(\frac{E + 1/3}{E + 1}\right)$$

where VL is lactate threshold speed (kph), Vmax maximum speed (V5) and E endurance (%). For example, if Vmax is 30 kph and E is 50%, the VL speed will be calculated as 16.67 kph, or alternatively VL pace as 3:36 min per km. A marathoner with a Vmax of 22.5 kph and an E of 90%, will have a VL speed of 14.6 kph, or alternatively VL pace as 4:07 min per km.

This means that the maximum speed (Vmax) and endurance (E) can also be calculated through simple equations:

$$Vmax = VL\left(\frac{E+1}{E+1/3}\right)$$

and:

$$E = \left(\frac{VL + Vmax/3}{Vmax - VL}\right)$$

Example 5

The Lactic Heart Rate Curve

As explained previously and shown in FIG. 13, a clear shift happens in the heart rate curve at the lactate threshold speed (VL=V2.333). At lactic speeds (>VL) the E-line has an elevated slope and points towards a supra-maximal heart rate (PS). The supra-maximal heart rate is based on the threshold speed level according to the following equation:

$$PS = p3 + p \cdot (V - 7/3)$$

where p3 equals HRmax, p the heart rate threshold interval and V the threshold speed. For example, if p and p3 equal 30 bpm and 200 bpm, respectively, PS equals 220 bpm at V3 threshold speed (PS=200+30⅔)=220 bpm). The supra-maximal heart rate reflects the increased energy demand at lactic speeds, after the oxidative system (the E-system) is maximized at exhaustion (at the VL speed). At lactic speeds the T5 transition point starts to decline (i.e. move to lower heart rate values), so the interval between T4 and T5 becomes smaller than $T_i$. The interval between T4 and T6, however, always equals $T_i$ at lactic speeds. FIG. 30 shows the fitting of a heart rate curve produced by an endurance runner, running on a treadmill at a constant lactic speed (16.5 kph) for 6 minutes.

The heart rate curve in FIG. 30 was produced at a V2.93 threshold speed and is therefore a lactic heart rate curve (>VL). At this high relative speed, the T1–T3 points have become directly aligned (in direct linear alignment) and their timing minimized (see Table 1). The linear E-line starts at T4 after only about 90 seconds and then drifts towards the extrapolated supra-maximal E-line endpoint (about 215 bpm). However, after about 5 minutes the E-line is cut short and overtaken by the F-line. At lactic speeds, the F-line always ends in a HRsubmax at T6 (the endpoint), which determines the Runtime for that specific speed level. This means that the runner could potentially have run to exhaustion in little less than 15 minutes at this speed. A fitting of the heart rate curve (Cardiolysis) returns an endurance (E) of 76% and a maximum speed (Vmax) of 24.1 kph for this runner. The race time predictor (Example 2) predicts potential race times of 37:19 minutes in the 10 km and 3:00 hours in the marathon, for this runner.

Lactic speed tests, like the one in FIG. 30, are ideal as the first test of a new user, especially for endurance runners. FIG. 37 shows the results from four other lactic running tests, performed by marathon runners.

Example 6

Heart Rate Recovery

The heart rate recovery kinetics of the HRK theory have been applied successfully to actual heart rate data. FIG. 31 shows an example heart rate response produced after running for 36 minutes at a sub-lactic pace (under the lactic threshold pace), followed by a passive recovery for another 74 minutes post-exercise. The activity curve is fitted with the heart rate model and the heart rate curve is subsequently placed inside the cardiometabolic framework.

After the termination of the activity there is an initial lag of about 10 seconds, but after that the heart rate components start declining from fixed repayment points (r-points) on the y-axis (r0-5 in FIG. 31). The r-points represent the origin (heart rate at start of recovery) of each respective recovery component curve, while the R-points represent the transitions in the recovery curve. The r0 point is equal to the maximum heart rate for the activity. Each component is repaid in succession over three repayment intervals, such as the A-component between r0 and r3. The r-points between r0 and r4 are evenly spaced and separated by the $R_i$ interval, just like the recovery points (R-points). The $R_i$-interval equals the $T_i$-interval ($R_i=T0$ between the transition points on the associated activity heart rate curve. The size of the remaining intervals between r4 and r6 is not equal to but rather directly related to the endurance of the individual. Endurance athletes typically have a large gap between the r4 and r6 points, which allows for a much faster repayment of the D-debt (slow, aerobic glycolysis) after strenuous exercise. The gap between the r4 and r6 points can thus be called a "recovery window", as it is crucial for the speed of recovery.

Example 7

The Heart Rate Vs Speed Relationship

Figure 1:
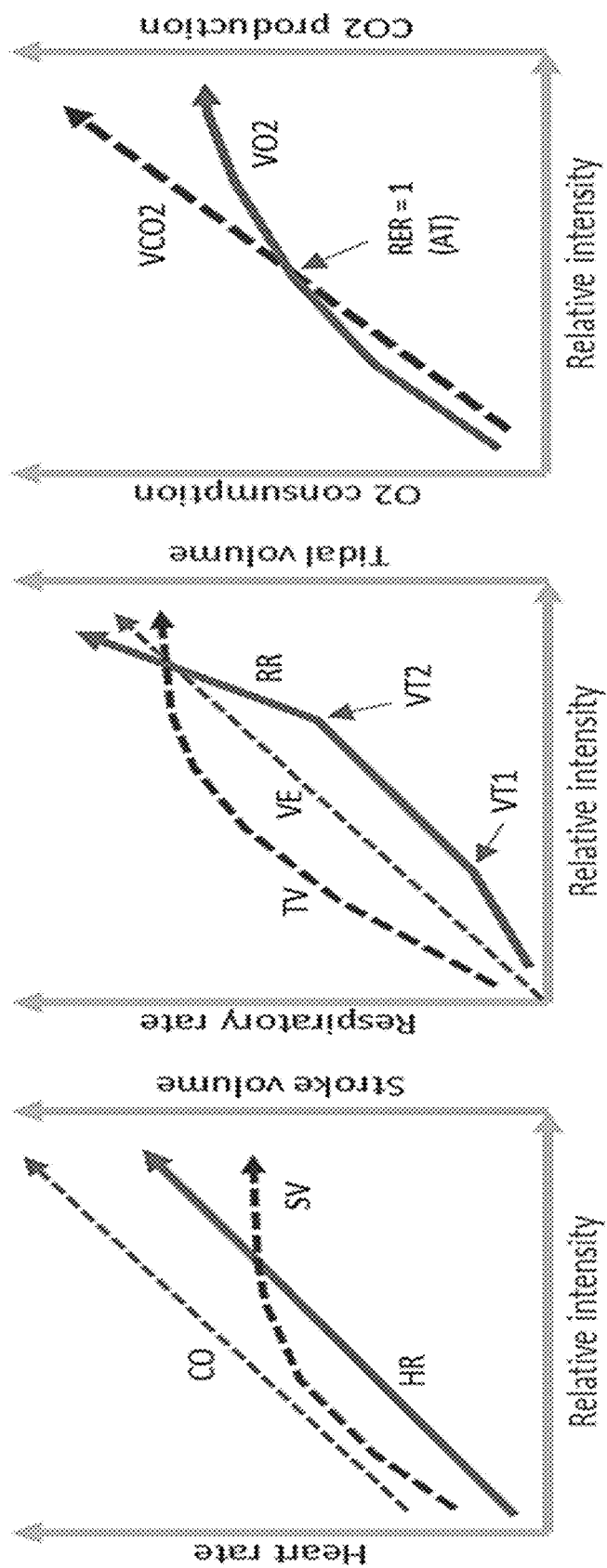
FIG. 1 shows an illustration of the cardiorespiratory response to exercise. The first graph shows the cardiovascular response, involving heart rate (HR), stroke volume (SV) and cardiac output (CO). The second graph shows the respiratory response, involving respiratory rate (RR), tidal volume (TV) and ventilation (VE). The ventilatory thresholds (VT1 and VT2) are indicated with arrows. The third graph shows the respiratory exchange, involving oxygen consumption (VO2) and CO2 output (VCO2). The anaerobic threshold (AT) is indicated where the lines intersect, reflecting a respiratory exchange ratio (RER) of 1.

The linear relationship between heart rate and submaximal running speed (HR-speed relationship) has been documented in many scientific studies (see FIG. 1) and is the physiological basis for many fitness features offered in popular fitness trackers. The HRK theory is, however, the first to fully explain the HR-speed relationship in the full context of energy thresholds and maximum speed. FIG. 32 shows the HR-speed relationship for two runners with widely different endurance capabilities.

The lower dotted line in FIG. 32 connects the five speed thresholds (V1–V5) of a runner with an endurance (E) of 40% and a max speed of 29 kph. The speed thresholds have a linear relationship with both heart rate and speed, and the three lowest thresholds (V1-3) fall on their respective heart rate thresholds (p1-3). The figure shows that the line can in fact be extrapolated all the way up to the maximum speed (V5). The upper dotted line in FIG. 32 similarly connects the five speed thresholds of a marathon runner with an endurance (E) of 100% and a max speed of 22.4 kph (heart rate thresholds not shown). Interestingly, the two lines are practically parallel and mainly separated at the y-intersect. The threshold points of the marathon runner lie more closely together, and the maximum speed is much lower. The lactate threshold speed (VL=V2.333) is similar for both runners (about 16 kph), so judging only from the LT-speed (like in traditional fitness tests), the runners would be wrongly assumed to have the same endurance level.

The line equations, shown above the lines, are of the form HR=Vz(x)+Pz, where Vz is the slope and Pz the y-intercept. Both runners have similar slopes of 8.4-8.5 bpm for each 1 kph change in submaximal speed below the lactate threshold. The slope of the line reflects the ratio between threshold intervals, i.e. $Vz=p/V_i$. The lines cross the y-axis at a specific point (Pz) determined by the HRmax and endurance (E) of the runner. The graph-insert shows that for runners at the low and high extremes of endurance (E=0% and 100%), the line will cross the y-axis in Pz at exactly the P0 heart rate level (P0=P). Runners with intermediate endurance will, however, have lines that cross at a specific lower ratio of P. This ratio is called Pz % and falls from 100% at the extremes of endurance, down to a minimum value of 66.7% (⅔) at an endurance (E) of about 41%. The Pz % ratio has the following relationship with endurance (E):

$Pz\% = 1 - (2E - 2E^2)/(E+1)$

HRmax can be calculated from Vmax (max speed) with the following equation:

$HRmax = Vmax(Vz)/Pz\%$

The slope of the HR-speed relationship (Vz) can be widely different for runners with different characteristics, ranging from less than 6.5 for world-class runners over all distances, to over 15 for some lower-level runners.

Example 8

HRmax

As explained in the Introduction, the HRmax concept is very well established in the scientific community. The concept is based on the notion that the heart rate of an individual reaches a fixed maximum at the completion of exhaustive exercise, regardless of the intensity of the exercise. Maximum heart rates are typically measured in incremental laboratory tests, where the subject runs or pedals towards exhaustion at intensities close to or exceeding the speed at VO2max. The maximum heart rate attained in such a laboratory test is then assumed to represent the maximum heart rate, or alternatively, the HRmax of the individual.

The HRK theory, however, reveals that this testing method is inherently flawed, leading to a serious underestimation of HRmax, especially for people with low endurance levels, such as sprinter types and sedentary people. The kinetics of the heart rate curve and the underlying energy systems cause the maximum heart rate at exhaustion to vary greatly, depending on the intensity of the exercise. FIG. 33 shows the calculated maximum heart rate at 8 different intensity levels, for 4 runners with different endurance levels and a fixed P of 50 bpm. The graph clearly shows that the true HRmax (=188 bpm) is only reached at the VL speed for all the different runners, regardless of the endurance level. On the other hand, the graph shows that the maximum heart rate gets progressively lower at both lower and higher intensities, especially for runners with low endurance levels. The HRK theory thus defines those non-VL max heart rates as HRsubmax, since they are lower than the true HRmax.

At high-intensity speeds (close to V3), such as those commonly reached during the final phase of incremental tests, the true HRmax can be seriously underestimated. For a person with low endurance (such as a sprinter type athlete or sedentary person) the HRmax can easily be underestimated by more than 20 bpm, due to this factor alone. In addition, non-athletic people are more likely to terminate the laboratory tests prematurely, at a lower relative effort, thus leading to an even larger underestimation of the true HRmax.

Example 9

Runmaker Solar

Runmaker Solar is a predictive model of heart rate dynamics during exercise of constant intensity. The model uses astronomy analogy for illustrative purposes and uses the input variables E (endurance), V (threshold speed) and P (heart rate level interval) to produce an estimated time-series of heart rate data. An optional variable can also be used by the model by defining a specific starting heart rate. An advanced least-squares method is then applied to minimize the difference between the model output and measured heart rate data to find the underlying values of variables E, V and P that reflect the runner's running profile. FIG. 34 shows a screenshot from the Runmaker Solar heart rate model.

The screenshot from the Runmaker Solar model in FIG. 34 shows five different heart rate curves generated in treadmill test runs by the same user. The box on the right side shows a list of downloaded test runs by the user (or multiple users), with the selected runs highlighted. The box on the left side shows the input variables (E, P and V), the graph dimensions and the selected test speed. Norm speed can be selected to normalize the data to a selected normalized running speed. If the Solve button is selected, the model calculates the least-squares best fit to the selected data. The boxes beneath the graph show a summary of some of the main results, such as Endurance (E), Lactate threshold (VL), Max speed (Vmax) and Max distance (Dmax) at the test speed (v).

Example 10

Case Examples

The eight graphs in FIG. 35 and FIG. 36 show case examples from the Runmaker Solar model, for four different runners, with every two adjacent graphs (A-B, C-D, E-F and G-H) produced by the same runner. The data for the three first users were collected in treadmill running tests at constant speeds (indicated) with a Polar heart rate monitor. The fourth runner (curves G and H) used a Garmin Forerunner to collect data from two track runs at nearly constant speeds. These data sets were not smoothed, for illustrative purposes. The whole line shows the best fit to the data set. The main results obtained by the method are shown underneath each graph. The model found a very good fit to the data in all cases and the repeatability was high, i.e. the results for different users were very relatively consistent in the two different test runs. Those four users show a wide range of endurance (E), i.e. ranging from 33% to almost 100%.

The four graphs in FIG. 37 show the fitting of heart rate curves produced by four different marathon runners in lactic treadmill running tests. The heart rate model produced a very good fit for all the curves, like the one previously shown in FIG. 30. The A and D tests were performed at relatively high threshold speeds (V2.9-3.0), so the runners hit T5 after only about 6 minutes. The B and C tests were run at lower threshold speeds (V2.7-2.8), so T5 was reached later. The Cardiolysis model calculated an endurance (E) of 70-78% for all four runners and marathon times ranging from 2:54 hours to 3:12 minutes.

List of Calculations

In the following list, the actual equations used to calculate each parameter are shown, together with illustrative numerical values based on the indicated input values for E, P, V and v.

| Nr. | Parameters | | Unit | Name | Equations |
|---|---|---|---|---|---|
| | E | 60.0% | % | Endurance | Input value |
| | P | 47.0 | bpm | Heart rate level | Input value |
| | V | 2.0 | V | Threshold speed | Input value |
| | v | 14.0 | kph | Actual speed | Input value |
| 1 | e | 4.0 | | Endurance base | $=10^{\wedge}E$ |
| 2 | X | 143.3 | min | Aerobic base time (neg.) | $=36e$ |
| 3 | Xf | 11.94 | | X factor | $=X/12$ |
| 4 | V1% | 37.5% | % | V1 percentage | $=E/(E+1)$ |
| 5 | V2% | 53.1% | % | V2 percentage | $=V1\% + (1 - V1\%)/4$ |
| 6 | $V_i$% | 15.6% | % | Vi percentage | $=(1 - V1\%)/4$ |
| 7 | V % | 50% | % | V percentage | $=(V - 1)/2$ |
| 8 | P3 | 188 | bpm | Maximum HR level | $=4P$ |
| 9 | P2 | 141 | bpm | Aerobic HR level | $=3P$ |
| 10 | P1 | 94 | bpm | Anaerobic HR level | $=2P$ |
| 11 | P0 | 47.0 | bpm | Resting HR level | $=P$ |
| 12 | px | 70.5 | bpm | p1 elevation | $=p1 - P0$ |
| 13 | p1% | 37.5% | % | p1 percentage | $=V1\% = px/P3$ |
| 14 | P | 35.3 | bpm | HR threshold interval | $=(p3 - p1)/2$ |
| 15 | p3 | 188.0 | bpm | Maximum HR threshold | $=P3$ |
| 16 | p2 | 152.8 | bpm | Aerobic HR threshold | $=p3 - p$ |
| 17 | p1 | 117.5 | bpm | Anaerobic HR threshold | $=P + p1\%(4P)$ |
| 18 | p0 | 82.3 | bpm | Base HR threshold | $=p1 - p$ |
| 19 | pL | 164.5 | bpm | Lactic heart rate | $=p2 + p/3$ |
| 20 | pV | 152.8 | bpm | V heart rate | $=(p1 + V\%(2p))$ |
| 21 | HRsub | 181.2 | bpm | HRsubmax | $=p1 + 3p/2$ |
| 22 | PS | 176.25 | bpm | Supramaximal heart rate | $=4P + (V - 7/3)p$ |
| 23 | $E_aL$ | 152.8 | bpm | $E_a$ lactic (>VL) | $=IF((V>=7/3), T4 - t4 \cdot (E_bL), p0 + V(p))$ |
| 24 | $E_aSL$ | 152.8 | bpm | $E_a$ superlactic (>VSL) | $=IF((V>=10/3), (pL - ((pL - p2) \cdot (3(V - 10/3)/2))))$ |
| 25 | $E_bL$ | 0.246 | | E slope lactic (>VL) | $=(PS - T4)/(t6 - t4)$ |
| 26 | v % | 53.1% | % | Relative test speed | $=V1\% + ((pV - p1)/(p)) \cdot ((Vi\%))$ |
| 27 | V5 | 26.4 | kph | Max speed threshold | $=V4 + V_i$ |
| 28 | V4 | 22.2 | kph | Anaerobic max threshold | $=V3 + V_i$ |
| 29 | V3 | 18.1 | kph | Aerobic max threshold | $=V2 + V_i$ |
| 30 | V2 | 14.0 | kph | Anaerobic threshold | $=v/v\%(V2\%)$ |
| 31 | V1 | 9.9 | kph | Aerobic threshold | $=v/v\%(V1\%)$ |
| 32 | $V_i$ | 4.12 | kph | V interval | $=V2 - V1$ |
| 33 | VSL | 23.6 | kph | Super-lactic threshold | $=V3 + Vi/3$ |
| 34 | VL | 15.4 | kph | Lactic threshold | $=V2 + Vi/3$ |
| 35 | Vopt | 1.667 | V | Optimal V speed | $=V1.667$ |
| 36 | vOpt | 12.63 | kph | Optimal speed | $=V1 + (Vopt - 1) \cdot V_i$ |
| 37 | T1opt | 88.2 | bpm | T1 optimal HR | $=T5opt - 4(Ti)$ |
| 38 | T2opt | 104.3 | bpm | T2 optimal HR | $=T5opt - 3(Ti)$ |
| 39 | T3opt | 120.5 | bpm | T3 optimal HR | $=T5opt - 2(Ti)$ |
| 40 | T4opt | 136.6 | bpm | T4 optimal HR | $=T5opt - Ti$ |
| 41 | T5opt | 152.8 | bpm | T5 optimal HR | $=IF((V<=Vopt), (p1 + (V - 1)/(Vopt - 1) \cdot p), p2)$ |
| 42 | Vmax4 | 2.39 | V | T4 max V | $=4/3 \cdot (1 - e/3) + (2/3e) + 1$ |
| 43 | HRmax4 | 166.5 | bpm | T4 max HR | $=(Vmax4 - 1) \cdot p + p1$ |
| 44 | TiMax | 21.5 | bpm | Max point interval | $=p3 - HRmax4$ |
| 45 | Ti | 16.1 | bpm | Transition point interval | $=TiMax(VL\%)$ |
| 46 | T2max | 123.4 | bpm | T2 max HR | $=IF((V>=Vopt), (p1 + 2/(3e) \cdot p), T2opt)$ |
| 47 | T5max | 188.0 | bpm | T5 max HR | $=p3$ |
| 48 | t4max | 24.0 | min | T4 max time | $=(12/(3 - Vopt))/(Vopt - 1)$ |
| 49 | $V^+$ | 1.00 | | V plus | $=V - 1$ |
| 50 | VL % | 75% | % | Lactic percentage | $=IF(((0.75V^+) > 1); 1; (0.75V^+))$ |
| 51 | t1 | 0.375 | min | T1 time | $=IF((V>=VL), 24(8^{-V}), 0.1875)$ |
| 52 | t2 | 0.75 | min | T2 time | $=IF((V>=VL), 48(8^{-V}), 0.375)$ |
| 53 | t3 | 2.25 | min | T3 time | $=IF((V>=VL), 144(8^{-V}), IF((V>=VSL), 2.4375 - 0.5625(V), 0.5625)$ |
| 54 | t4 | 12.0 | min | T4 time | $=IF((V<=VSL), 768(8^{-V}), 0.75)$ |
| 55 | t5 | 77.7 | min | T5 time | $=IF(V > 7/3, ((F_a - PS_a)/(PS_b - F_b), (F_a - E_a)/(E_b - F_b))$ |
| 56 | t6 | 143.4 | min | T6 time | $=t4(tf)$ |
| 57 | tf | 11.94 | | Time factor | $=IF(V > 7/3, Xf \cdot (V - 7/3) \cdot e^{\wedge}((0.932 - 0.375 \cdot \ln(X) \cdot (V - 7/3), Xf)$ |
| 58 | RT | 143.4 | min | Runtime (RT) | $=t6$ |
| 59 | RD | 33.4 | km | Rundistance (RD) | $=v(RT/60)$ |
| 60 | $PS_a$ | 153.8 | bpm | E line intercept (>VL) | $=PS - t6 \cdot PS_b$ |

-continued

| Nr. | Parameters | | Unit | Name | Equations |
|---|---|---|---|---|---|
| 61 | $PS_b$ | 0.156 | | E line slope (>VL) | =(PS − T4)/(t6 − 14) |
| 62 | T1 | 107.3 | bpm | Transition point 1 | =IF((V >= Vopt); T2 − Ti; T1opt) |
| 63 | T2 | 123.4 | bpm | Transition point 2 | =IF((V >= 2.333); p1 + p(3 − V)/e, IF((V <= Vopt), T2opt, T2max)) |
| 64 | T3 | 139.6 | bpm | Transition point 3 | =IF((V >= Vopt); T2 + Ti; T3opt) |
| 65 | T4 | 155.7 | bpm | Transition point 4 | =IF((V >= Vopt); T3 + Ti; T4opt) |
| 66 | T5 | 170.4 | bpm | Transition point 5 | =IF(V > 7/3, $PS_a$ + $PS_b$ · t5, $E_a$ + $E_b$ · t5) |
| 67 | T6 | 176.3 | bpm | Endpoint | =$F_a$ + t6 − ($F_b$) |
| 68 | tMax | 286.4 | min | Max running time | =2X |
| 69 | Dmax | 60.3 | km | Max running distance | =tMax · (Vopt/60) |
| 70 | tL | 71.7 | min | Lactic time | =X/2 |
| 71 | DL | 18.4 | km | Lactic distance | =VL · (tL/60) |
| 72 | CMF % | 100% | % | Framework percentage | =IF(((V − 1)/(Vopt − 1)) >= 1; 1;(V − 1)/(Vopt − 1)) |
| 73 | $L_b$ | 0.246 | km | Lactic slope | =(p1 + 2p · (CMF %) − $E_a$)/t6 |
| 74 | $X_E$ | 143.3 | min | E base point (neg. time) | =IF(V > 7/3,(($E_a$ − p1)/$L_b$), X) |
| 75 | $X_F$ | 143.3 | min | F base point (neg. time) | =$X_E$ |
| 76 | p3low | 188.0 | bpm | p3 suboptimal | =(p1 + 2p · (CMF %)) |
| 77 | p2low | 152.8 | bpm | p2 suboptimal | =(p1 + p · (CMF %)) |
| 78 | p3r | 4.00 | | p3 ratio | =(4p)/($E_a$ − p1) |
| 79 | EaV | 2.000 | V | E line V intercept | =2 + ($E_a$ − p2)/p |
| 80 | FaV | 2.333 | V | F line V intercept | =IF(V > 7/3, ($E_a$V + 1/3), (V + 1/3)) |
| 81 | $F_a$ | 161.9 | bpm | F line intercept | =p0 + $F_a$V · p |
| 82 | $F_b$ | 0.128 | | F line slope | =IF(V > 5/3, ($F_a$ − p2)/(−$X_F$), 0) |

The invention claimed is:

1. A computer-implemented method of determining exercise parameters for a human individual, comprising steps of:
providing, to a processing unit, data describing heart rate as a function of time during sub-maximal exercise of at least one human individual;
fitting, with the processing unit, a continuous curve to the heart rate data, the curve comprising a combination of a plurality of consecutive heart rate range components that follow each other in order over time, wherein each range component represents a combination of biophysical energy systems used to provide and replenish adenosine triphosphate (ATP) to muscle cells of the individual, wherein the energy systems include at least an anaerobic glycolytic system (C-energy system), an aerobic glycolytic system (D-energy system) and an oxidative system (E-energy system), wherein the range components include at least an E-range component indicative of a dominant E-energy system with declining C and D energy systems, and an F-range component indicative of a dominant E-energy system with a depleted C-energy system and with a declining D-energy system, wherein the range components meet at transition points that together with a starting point of the exercise and an end point of the exercise constitute curve points, positions of the transition points on the heart rate curve being a measure of performance parameters of the said human individual, and wherein the fitting comprises estimating the position of said transition points such that the difference in heart rate between consecutive transition points has a pre-determined relationship, and determining said range components between adjacent curve points thus providing a continuous curve; and
determining, based on the curve, exercise performance parameter values with the processing unit, including at least an aerobic heart rate threshold (p1), an aerobic endurance level (E), and a maximal heart rate (HRmax) that are characteristic for said individual, wherein the endurance level (E) is determined from the aerobic heart rate threshold (p1) and a slope of the E-range component, and wherein the maximal heart rate (HRmax) is determined from the aerobic heart rate threshold (p1), the slope of the E-range component and a slope of the F-range component.

2. The method of claim 1, wherein the fitting comprises a stepwise process that comprises steps of:
a. estimating a position of curve points on the heart rate curve;
b. fitting a continuous curve to the heart rate data between the curve points;
c. determine the deviation of the continuous curve from the heart rate data;
d. repeating the process in steps a-c until the deviation has been minimized.

3. The method of claim 1, wherein the plurality of consecutive heart rate range components comprises consecutively an A-range component, a B-range component, a C-range component, a D-range component, the E-range component and the F-range components, wherein at least the C and D-range components are non-linear, and at least the E and F-range components are linear over time.

4. The method of claim 1, wherein the plurality of consecutive heart rate range components comprises consecutively an A-range component, a B-range component, a C-range component, a D-range component, the E-range component and the F-range component, wherein the A and the B-range component meet at a first transition point (T1), the B and the C-range component meet at a second transition point (T2), the C and the D-range component meet at a third transition point (T3), the D and the E-range component meet at a fourth transition point (T4), and the E and the F-range component meet at a fifth transition point (T5), and the F-range component is completed at the endpoint (T6), wherein
when the exercise is performed to exhaustion at an intensity that is equal to a lactate threshold for the individual, a heart rate difference between successive transition points T1 to T5 is equal, such that Ti=HR(T5)−HR(T4)=HR(T4)−HR(T3)=HR(T3)−HR(T2)=HR(T2)−HR(T1), when the exercise is performed at an intensity that is above the lactate threshold for the individual, the heart rate difference between successive transition points T1 to T4 is equal, i.e. Ti =HR (T4)−HR(T3)=HR(T3)−HR(T2)=HR(T2)−HR(T1), while the heart rate difference between transition points T4 and T5 (HR(T5)−HR(T4)), and between transition points T5 and T6(HR(T6)−HR(T5)), are both smaller than Ti, and when the exercise is performed at an intensity that is below the lactate threshold for the individual, the heart rate difference between successive transition points T1 to T5 is equal, i.e., Ti=HR(T5)−HR(T4)=HR(T4)−HR(T3)=HR(T3)−HR(T2)=HR(T2)−HR(T1), while the heart rate difference between transition points T5 and T6(HR(T6)−HR(T5)), is smaller than Ti.

5. The method of claim 4, wherein a difference in time between adjacent transition points from T1 to T4 is independent of endurance level of an individual, while a time difference between T5–T4 and T6–T5 are affected by the endurance level of the individual.

6. The method of claim 4, wherein a difference in time between adjacent transition points T1-T4 has a fixed relationship which is independent of the endurance level of the individual, while a difference in times between the transition point T5 and the endpoint T6 is a measure of the endurance of the individual.

7. The method of claim 6, wherein the time of the first four transition points T1-T4 is in a fixed relationship with a relative intensity of the exercise being presented as a range of five evenly spaced speed thresholds (V1-V5).

8. The method of claim 1, wherein the plurality of consecutive heart rate range components comprises a first linear A-range component that meets a first non-linear B-range component at a transition point T1, three consecutive non-linear range components, i.e., the B-range component, a C-range component and a D-range component, that follow the first A-range component and meet at transition points T2 and T3, and the fifth linear E-range component that follows the three non-linear range components, i.e., the B, the C and the D-range components, and meets the D-range component at transition point T4, and the sixth linear F-range component that follows and meets the linear E-range component at a transition point T5, wherein the non-linear range components are described by the equations:

$$B_t = B_a + B_b(Ln(t))$$

$$C_t = C_a + C_b(Ln(t))$$

$$D_t = D_a + D_b(Ln(t))$$

wherein $B_t$, $C_t$ and $D_t$ equal the heart rate at any given time t during the respective range components (B, C and D), Ba, Ca and Da equal the y-axis intercepts, $B_b$, $C_b$ and $D_b$ equal the exponents of the range component logarithmic equations, and t equals time;

and wherein the linear A and F-range components are described by the equations:

$$At = Aa + Ab(t)$$

$$Ft = Fa + Fb(t)$$

where At and Ft equal heart rate at any given time t, Aa and Fa equal the y-axis intercepts, Ab and Fb equal the slopes of the lines and t equals time.

9. The method of claim 8, wherein the linear E-range component is, at sub-lactic speeds (<VL) and lactic speeds (>VL), respectively, wherein VL equals a lactate threshold speed (V2.333 in V units), described by the following equations:

$$E_t(\text{sub-lactic}) = E_a + E_b(t)$$

$$Et(\text{lactic}) = T4 + (PS - T4)(t - t4)/(t6 - t4)$$

where Et equals heart rate at any given time t, Ea equals the y-axis intercept, Eb equals a slope of the line, t equals time, T4 equals heart rate at the T4 transition point, PS equals an extrapolated supramaximal heart rate, and t4 and t6 equal times at T4 and T6 transition points, respectively.

10. The method of claim 1, wherein the data describing heart rate of the human individual further includes recovery rate heart rate data following an end of the exercise, wherein the heart rate of the individual approaches a resting heart rate following the end of the exercise, and wherein the heart rate data following the end of the exercise is fitted, via the processing unit, to a heart rate recovery curve comprising at least two recovery range components that are separated by recovery transition points, and wherein at least one exercise performance parameter value is obtained by analysis of the heart rate curve during the exercise and the heart rate recovery curve following the end of the exercise.

11. The method of claim 10, wherein the heart rate recovery curve comprises at least four recovery range components that meet at recovery transition points (R1, R2, R3 and R4), which correspond respectively to the transition points (T1, T2, T3 and T4) of the heart rate curve during the exercise, wherein a difference in heart rate between adjacent recovery transition points (Ri) is equal to the difference in heart rate between the corresponding transition points (Ti) on the curve describing heart rate during the exercise such that the transition points and the recovery points are in reverse vertical symmetry with each other.

12. A system for determining at least one exercise parameter for a human individual, the system comprising
 a. at least one computer-readable memory
 b. at least on processing unit, the processing unit being adapted to:
 receive data describing heart rate as a function of time during sub-maximal exercise of at least one human individual;
 storing the heart rate data to computer-readable memory;
 fitting a continuous curve to the heart rate data, wherein the continuous curve comprises a combination of a plurality of consecutive hear rate range components that follow each other in order over time, wherein each range component represents a combination of biophysical energy systems used to provide and replenish adenosine triphosphate (ATP) to muscle cells of the individual, wherein the energy systems include at least an anaerobic glycolytic system (C-energy system), an aerobic glycolytic system (D-energy system) and an oxidative system (E-energy system), wherein the range components include at least an E-range component indicative of a dominant E-energy system with declining C and D energy systems, and an F-range component indicative of a dominant E-energy system with a depleted C-energy system and with a declining D-energy system, wherein the range components meet at transition points that together with a starting point of the exercise and an end point of the exercise constitute curve points, the positions of the transition points on the heart rate curve being a measure of performance parameters of the said human individual, and wherein the fitting comprises estimating the position of said transition points such that the difference in hear rate between consecutive transition points has a predetermined relationship, and determining said range components between adjacent curve points thus providing a continuous curve;

determining exercise performance parameter values from the curve fitting or its individual range components including at least an aerobic heart rate threshold (p1), an aerobic endurance level (E), and a maximal heart rate (HRmax) that are characteristic for said individual, wherein the endurance level (E) is determined from the aerobic heart rate threshold (p1) and a slope of the E-range component, and wherein the maximal heart rate (HRmax) is determined from the aerobic heart rate threshold (p1), the slope of the E-range component and a slope of the F-range component.

13. The system of claim 12, wherein the system is adapted to fit a first continuous curve of the heart rate during exercise, followed by a second continuous curve that describes the decay in heart rate for the individual following an end of the exercise.

* * * * *